(12) United States Patent
Abbitt

(10) Patent No.: US 9,725,731 B2
(45) Date of Patent: Aug. 8, 2017

(54) SB-UBI TERMINATOR SEQUENCE FOR GENE EXPRESSION IN PLANTS

(71) Applicant: PIONEER HI-BRED INTERNATIONAL, INC., Johnston, IA (US)

(72) Inventor: Shane E. Abbitt, Ankeny, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/768,057

(22) PCT Filed: Feb. 5, 2014

(86) PCT No.: PCT/US2014/014795
§ 371 (c)(1),
(2) Date: Aug. 14, 2015

(87) PCT Pub. No.: WO2014/126755
PCT Pub. Date: Aug. 21, 2014

(65) Prior Publication Data
US 2015/0376633 A1    Dec. 31, 2015

(51) Int. Cl.
*A01H 5/10* (2006.01)
*A01H 1/00* (2006.01)
*C12N 15/82* (2006.01)
*C12N 15/00* (2006.01)

(52) U.S. Cl.
CPC ................. *C12N 15/8216* (2013.01)

(58) Field of Classification Search
None
See application file for complete search history.

(56) References Cited

U.S. PATENT DOCUMENTS

2010/0011470 A1* 1/2010 Wan .................... C12N 9/1205
800/287

FOREIGN PATENT DOCUMENTS

| CN | 1753995 A | 3/2006 |
|---|---|---|
| CN | 102234646 A | 11/2011 |
| WO | 2009/150541 A2 | 12/2009 |

OTHER PUBLICATIONS

Shahjahan Ali et al., Quantitative regulation of the Flaveria Me1 gene is controlled by the 3'-untranslated region and sequences near the amino terminus, Plant Molecular Biology, 2001, pp. 251-261, vol. 46.
Gynheung An et al., Functional Analysis of the 3' Control Region of the Potato Wound-Inducible Proteinase Inhibitor II Gene, The Plant Cell, Jan. 1989, pp. 115-122, vol. 1.
Stephane Bieri et al., Geminivirus sequences as bidirectional transcription termination/polyadenylation signals for economic construction of stably expressed transgenes, Molecular Breeding, 2002, pp. 107-117, vol. 10.
David M. Goodstein et al., Phytozome: a comparative platform for green plant genomics, Nucleic Acids Research, 2012, D1178-D1186, vol. 40.
Ivan L.W. Ingelbrecht et al., Different 3' End Regions Strongly Influence the Level of Gene Expression in Plant Cells, The Plant Cell, Jul. 1989, pp. 671-680, vol. 1.
Michael Keil et al., Primary structure of a proteinase inhibitor II gene from potato (*Solanum tuberosum*), Nucleic Acids Research, 1986, pp. 5641-5650, vol. 14, No. 14.
International Search Report—PCT/US2014/014795—mailed May 9, 2014.
Zhensheng Gao et al, Efficient genetic transformation of Sorghum using a visual screening marker, *Genome*, Dec. 31, 2005, pp. 321-333, vol. 48.

* cited by examiner

*Primary Examiner* — Phuong Bui

(57) ABSTRACT

The present invention discloses polynucleotide sequences that can be used to regulate gene expression in plants. Terminator sequences from *Sorghum bicolor* that are functional in plants are disclosed. Nucleic acid molecules, recombinant expression constructs, plants and seed comprising these terminator sequences are further disclosed.

11 Claims, 8 Drawing Sheets

SEQUENCE LISTING

<160> NUMBER OF SEQ ID NOS: 19

<210> SEQ ID NO 1
<211> LENGTH: 584
<212> TYPE: DNA
<213> ORGANISM: Sorghum bicolor

<400> SEQUENCE: 1

| gccgtgggtc | gtttaagctg | ccgctgtacc | tgtgtcgtct | ggtgccttct | ggtgtacctg | 60 |
| ggaggttgtc | gtctatcaag | tatctgtggt | tggtgtcatg | agtcagtgag | tcccaatact | 120 |
| gttcgtgtcc | tgtgtgcatt | atacccaaaa | ctgttatggg | caaatcatga | ataagcttga | 180 |
| tgttcgaact | taaaagtctc | tgctcaatat | ggtattatgg | ttgttttttgt | tcgtctccta | 240 |
| atatttgcct | gggatcaaat | tttattggct | ggtgttcatt | tgacctccat | gttcttgcta | 300 |
| ggctccattt | tttactctac | agccataata | tgtttgattg | tttggtttgt | tctttgttgt | 360 |
| acacctggtt | ctgtcgagct | tagttttcga | cactggctta | cagcttaaca | tgttgctatt | 420 |
| ttattgggtt | ctgattgcta | ttttattggg | ttctgattgc | tagttttttgc | tgaatccaaa | 480 |
| aaccatgtta | tttatttaag | cgatccaggt | tattattatg | atggtggcta | agttttttttt | 540 |
| tttccaaggg | taaattttct | ggattctcca | gtgtttctgt | ggcc | | 584 |

<210> SEQ ID NO 2
<211> LENGTH: 28
<212> TYPE: DNA
<213> ORGANISM: artificial sequence
<220> FEATURE:
<223> OTHER INFORMATION: forward primer TMS2118

<400> SEQUENCE: 2

| actagtgccg | tgggtcgttt | aagctgcc | | | | 28 |

<210> SEQ ID NO 3
<211> LENGTH: 26
<212> TYPE: DNA
<213> ORGANISM: artificial sequence
<220> FEATURE:
<223> OTHER INFORMATION: reverse primer TMS2119

<400> SEQUENCE: 3

| gaattcggcc | acagaaacac | tggaga | | | | 26 |

<210> SEQ ID NO 4
<211> LENGTH: 3612
<212> TYPE: DNA
<213> ORGANISM: artificial sequence
<220> FEATURE:
<223> OTHER INFORMATION: plasmid PHP32498

<400> SEQUENCE: 4

| gggcgaattg | ggcccgacgt | cgcatgctcc | cggccgccat | ggcggccgcg | ggaattcgat | 60 |
| actagtgccg | tgggtcgttt | aagctgccgc | tgtacctgtg | tcgtctggtg | ccttctggtg | 120 |
| tacctgggag | gttgtcgtct | atcaagtatc | tgtggttggt | gtcatgagtc | agtgagtccc | 180 |
| aatactgttc | gtgtcctgtg | tgcattatac | ccaaaactgt | tatgggcaaa | tcatgaataa | 240 |
| gcttgatgtt | cgaacttaaa | agtctctgct | caatatggta | ttatggttgt | ttttgttcgt | 300 |
| ctcctaatat | ttgcctggga | tcaaatttta | ttggctggtg | ttcatttgac | ctccatgttc | 360 |
| ttgctaggct | ccatttttta | ctctacagcc | ataatatgtt | tgattgtttg | gtttgttctt | 420 |
| tgttgtacac | ctggttctgt | cgagcttagt | tttcgacact | ggcttacagc | ttaacatgtt | 480 |

```
gctatttat   tgggttctga   ttgctatttt   attgggttct   gattgctagt   ttttgctgaa    540
tccaaaaacc  atgttattta   tttaagcgat   ccaggttatt   attatgatgg   tggctaagtt    600
tttttttttc  caagggtaaa   ttttctggat   tctccagtgt   ttctgtggcc   gaattcaatc    660
actagtgaat  tcgcggccgc   ctgcaggtcg   accatatggg   agagctccca   acgcgttgga    720
tgcatagctt  gagtattcta   tagtgtcacc   taaatagctt   ggcgtaatca   tggtcatagc    780
tgtttcctgt  gtgaaattgt   tatccgctca   caattccaca   aacatacga    gccggaagca    840 taaagtgtaa  agcctggggt   gcctaatgag   tgagctaact   cacattaatt   gcgttgcgct    900
cactgcccgc  tttccagtcg   ggaaacctgt   cgtgccagct   gcattaatga   atcggccaac    960
gcgcggggag  aggcggtttg   cgtattgggc   gctcttccgc   ttcctcgctc   actgactcgc   1020
tgcgctcggt  cgttcggctg   cggcgagcgg   tatcagctca   ctcaaaggcg   gtaatacggt   1080
tatccacaga  atcaggggat   aacgcaggaa   agaacatgtg   agcaaaaggc   cagcaaaagg   1140
ccaggaaccg  taaaaaggcc   gcgttgctgg   cgttttttcca  taggctccgc   cccccctgacg  1200 agcatcacaa  aaatcgacgc   tcaagtcaga   ggtggcgaaa   cccgacagga   ctataaagat   1260
accaggcgtt  tccccctgga   agctccctcg   tgcgctctcc   tgttccgacc   ctgccgctta   1320
ccggatacct  gtccgccttt   ctcccttcgg   gaagcgtggc   gctttctcat   agctcacgct   1380
gtaggtatct  cagttcggtg   taggtcgttc   gctccaagct   gggctgtgtg   cacgaacccc   1440
ccgttcagcc  cgaccgctgc   gccttatccg   gtaactatcg   tcttgagtcc   aacccggtaa   1500
gacacgactt  atcgccactg   gcagcagcca   ctggtaacag   gattagcaga   gcgaggtatg   1560
taggcggtgc  tacagagttc   ttgaagtggt   ggcctaacta   cggctacact   agaagaacag   1620
tatttggtat  ctgcgctctg   ctgaagccag   ttaccttcgg   aaaaagagtt   ggtagctctt   1680
gatccggcaa  acaaaccacc   gctggtagcg   gtggtttttt   tgtttgcaag   cagcagatta   1740
cgcgcagaaa  aaaaggatct   caagaagatc   ctttgatctt   ttctacgggg   tctgacgctc   1800
agtggaacga  aaactcacgt   taagggattt   tggtcatgag   attatcaaaa   aggatcttca   1860
cctagatcct  tttaaattaa   aaatgaagtt   ttaaatcaat   ctaaagtata   tatgagtaaa   1920
cttggtctga  cagttaccaa   tgcttaatca   gtgaggcacc   tatctcagcg   atctgtctat   1980
ttcgttcatc  catagttgcc   tgactccccg   tcgtgtagat   aactacgata   cgggagggct   2040
taccatctgg  ccccagtgct   gcaatgatac   cgcgagaccc   acgctcaccg   gctccagatt   2100
tatcagcaat  aaaccagcca   gccggaaggg   ccgagcgcag   aagtggtcct   gcaactttat   2160
ccgcctccat  ccagtctatt   aattgttgcc   gggaagctag   agtaagtagt   tcgccagtta   2220
atagtttgcg  caacgttgtt   gccattgcta   caggcatcgt   ggtgtcacgc   tcgtcgtttg   2280
gtatggcttc  attcagctcc   ggttcccaac   gatcaaggcg   agttacatga   tcccccatgt   2340
tgtgcaaaaa  agcggttagc   tccttcggtc   ctccgatcgt   tgtcagaagt   aagttggccg   2400
cagtgttatc  actcatggtt   atggcagcac   tgcataattc   tcttactgtc   atgccatccg   2460
taagatgctt  ttctgtgact   ggtgagtact   caaccaagtc   attctgagaa   tagtgtatgc   2520
ggcgaccgag  ttgctcttgc   ccggcgtcaa   tacgggataa   taccgcgcca   catagcagaa   2580
ctttaaaagt  gctcatcatt   ggaaaacgtt   cttcggggcg   aaaactctca   aggatcttac   2640
cgctgttgag  atccagttcg   atgtaaccca   ctcgtgcacc   caactgatct   tcagcatctt   2700
ttactttcac  cagcgtttct   gggtgagcaa   aacaggaag    gcaaaatgcc   gcaaaaaagg   2760
gaataagggc  gacacggaaa   tgttgaatac   tcatactctt   cctttttcaa   tattattgaa   2820
```

```
gcatttatca gggttattgt ctcatgagcg gatacatatt tgaatgtatt tagaaaaata    2880
aacaaatagg ggttccgcgc acatttcccc gaaaagtgcc acctgatgcg gtgtgaaata    2940
ccgcacagat gcgtaaggag aaaataccgc atcaggaaat tgtaagcgtt aatattttgt    3000
taaaattcgc gttaaatttt tgttaaatca gctcattttt taaccaatag gccgaaatcg    3060
gcaaaatccc ttataaatca aaagaataga ccgagatagg gttgagtgtt gttccagttt    3120
ggaacaagag tccactatta agaacgtgg actccaacgt caagggcga aaaccgtct    3180
atcagggcga tggcccacta cgtgaaccat caccctaatc aagtttttg gggtcgaggt    3240
gccgtaaagc actaaatcgg aaccctaaag ggagccccg atttagagct tgacggggaa    3300
agccggcgaa cgtggcgaga aaggaaggga agaaagcgaa aggagcgggc gctagggcgc    3360
tggcaagtgt agcggtcacg ctgcgcgtaa ccaccacacc cgccgcgctt aatgcgccgc    3420
tacagggcgc gtccattcgc cattcaggct gcgcaactgt tgggaagggc gatcggtgcg    3480
ggcctcttcg ctattacgcc agctggcgaa aggggatgt gctgcaaggc gattaagttg    3540
ggtaacgcca gggttttccc agtcacgacg ttgtaaaacg acggccagtg aattgtaata    3600
cgactcacta ta                                                       3612
```

<210> SEQ ID NO 5
<211> LENGTH: 50961
<212> TYPE: DNA
<213> ORGANISM: artificial sequence
<220> FEATURE:
<223> OTHER INFORMATION: plasmid PHP34006

<400> SEQUENCE: 5

```
acgtgaccct agtcacttag gttaccagag ctggtcacct ttgtccacca agatggaact      60
gcggccgctc attaattaag tcaggcgcgc ctctagttga agacacgttc atgtcttcat     120
cgtaagaaga cactcagtag tcttcggcca gaatggccat ctggattcag caggcctaga     180
aggccattta atcctgagg atctggtctt cctaaggacc cggatatcg ctatcaactt     240
tgtatagaaa agttgggccg aattcggcca cagaaacact ggagaatcca gaaaatttac     300
ccttggaaaa aaaaaaactt agccaccatc ataataataa cctggatcgc ttaaataaat     360
aacatggttt ttggattcag caaaaactag caatcagaac ccaataaaat agcaatcaga     420
acccaataaa atagcaacat gttaagctgt aagccagtgt cgaaaactaa gctcgacaga     480
accaggtgta caacaaagaa caaaccaaac aatcaaacat attatggctg tagagtaaaa     540
aatggagcct agcaagaaca tggaggtcaa atgaacacca gccaataaaa tttgatccca     600
ggcaaatatt aggagacgaa caaaacaac cataatacca tattgagcag agacttttaa     660
gttcgaacat caagcttatt catgatttgc ccataacagt tttgggtata atgcacacag     720
gacacgaaca gtattgggac tcactgactc atgacaccaa ccacagatac ttgatagacg     780
acaacctccc aggtacacca gaaggcacca gacgacacag gtacagcggc agcttaaacg     840
acccacggca ctagtaagct tagatcttca ttgtttgcct ccctgctgcg gttttttcacc    900
gaagttcatg ccagtccagc gttttttgcag cagaaaagcc gccgacttcg gtttgcggtc     960
gcgagtgaag atccctttct tgttaccgcc aacgcgcaat atgccttgcg aggtcgcaaa    1020
atcggcgaaa ttccataccct gttcaccgac gacggcgctg acgcgatcaa agacgcggtg    1080
atacatatcc agccatgcac actgatactc ttcactccac atgtcggtgt acattgagtg    1140
cagcccggct aacgtatcca cgccgtattc ggtgatgata tcggctgat gcagtttctc    1200
ctgccaggcc agaagttctt tttccagtac cttctctgcc gtttccaaat cgccgctttg    1260
```

```
gacataccat ccgtaataac ggttcaggca cagcacatca aagagatcgc taatggtatc    1320
ggtgtgagcg tcgcagaaca ttacattgac gcaggtgatc ggacgcgtcg ggtcgagttt    1380
acgcgttgct tccgccagtg gcgcgaaata ttcccgtgca ccttgcggac gggtatccgg    1440
ttcgttggca atactccaca tcaccacgct tgggtggttt tgtcacgcg ctatcagctc     1500 tttaatcgcc tgtaagtgcg cttgctgagt ttccccgttg actgcctctt cgctgtacag    1560
ttctttcggc ttgttgcccg cttcgaaacc aatccctaaa gagaggttaa agccgacagc    1620
agcagtttca tcaatcacca cgatgccatg ttcatctgcc cagtcgagca tctcttcagc    1680
gtaagggtaa tgcgaggtac ggtaggagtt ggccccaatc cagtccatta atgcgtggtc    1740
gtgcaccatc agcacgttat cgaatccttt gccacgcaag tccgcatctt catgacgacc    1800
aaagccagta aagtagaacg gtttgtggtt aatcaggaac tgttggccct tcactgccac    1860
tgaccggatg ccgacgcgaa gcgggtagat atcacactct gtctggcttt tggctgtgac    1920
gcacagttca tagagataac cttcacccgg ttgccagagg tgcggattca ccacttgcaa    1980
agtcccgcta gtgccttgtc cagttgcaac cacctgttga tccgcatcac gcagttcaac    2040
gctgacatca ccattggcca ccacctgcca gtcaacagac gcgtggttac agtcttgcgc    2100
gacatgcgtc accacggtga tatcgtccac ccaggtgttc ggcgtggtgt agagcattac    2160
gctgcgatgg attccggcat agttaaagaa atcatggaag taagactgct ttttcttgcc    2220
gttttcgtcg gtaatcacca ttcccggcgg gatagtctgc cagttcagtt cgttgttcac    2280
acaaacggtg atacctgcac atcaacaaat tttggtcata tattagaaaa gttataaatt    2340
aaaatataca cacttataaa ctacagaaaa gcaattgcta tatactacat tctttatt     2400 tgaaaaaaat atttgaaata ttatattact actaattaat gataattatt atatatatat    2460
caaaggtaga agcagaaact tacgtacact tttcccggca ataacatacg gcgtgacatc    2520
ggcttcaaat ggcgtatagc cgccctgatg ctccatcact tcctgattat tgacccacac    2580
tttgccgtaa tgagtgaccg catcgaaacg cagcacgata cgctggcctg cccaaccttt    2640
cggtataaag acttcgcgct gataccgac gttgcccgca taattacgaa tatctgcatc     2700
ggcgaactga tcgttaaaac tgcctggcac agcaattgcc cggcttttctt gtaacgcgct    2760 ttcccaccaa cgctgatcaa ttccacagtt ttcgcgatcc agactgaatg cccacaggcc    2820
gtcgagtttt ttgatttcac gggttggggt ttctacagga cggaccatgg tgtcgtgtgg    2880
atccaaattg tatgcaaggt gaatgacttt cttttcgtaa actagatagg agtactcctc    2940
caggatgctt aacccgtatt gacgtacaga ggtctatgat cctttgttt ataaaggagc     3000 ttgtagttca gtcagtctta tacttcacga tgcccatgtt tctatatagg atattatctt    3060
ggctttgtaa gtacttcacg caggttatgt tctgtttcta ggatattatc ctcatacatg    3120
cgaagaacca attttttcccc cattctcttc gggtacttt tcttgggtag gcatgctctc      3180
ttggaccaac tagcataaaa cataatcatt tttccctaca gccttgacca gctataatcg    3240
aaatcatgct catttttcta agaaagactg aatacagctc caatttaaac aatttaaatc    3300
ataaacttgt aactcaatta gagaaaagca gagcccttcg gctcctatct aaaggaatta    3360
ccccatgaaa gccataaaaa cgaaccttgc tctgatacca gacgggtcta cgctcgcgga    3420
actaggatct tgcgctctac tcgcacaaag tgaactcgca caaagtgtgt ttcaagcaca    3480
gaagttttta tttctcaaat caggagtaaa ctcgcgttgt ggtgcgtgtt tgcaacctga    3540
atacaaggct ccttatatag agagttgtgg agcttctctgg catcgttagg tggcatccac    3600
```

```
caataatgca gataagcatc atcacatgtc tctggcctaa caactttgcg taagaatcct    3660
gcaaagttac taaaggtcat cgtgcgtgac tagacaacgc acaccgacaa acttaaaata    3720
aagagacatt atactttgtc tcctctttac ataaagtgag tggtatccag ctcactccgc    3780
atcttatcag tcttcacacc ggttggtatc aacacgtggt aggggtccgc cacttccgct    3840
tcagtcatca ttactgatat ccagcagatc tagagcatct tcaataagat attcttgttc    3900
tgcacgcaga ttttcttgct ccctcagtaa ttcctcccac agtgagtctt ctgatatttc    3960
ttcaagtttc ttctcccatc tgatcttttc ctgcacaaac gagtcaattt ggtcttttca    4020
gacccaagta aaacaagtgt tagtttcaca ggagtaaaac tccctgtcag gatttctgga    4080
tgttctggag atcttcagtt ttgctggttt attgcatcca catttgaaaa ccggctcttc    4140
acttagtgtt agcacattga tttgatgcaa cctgtagcct ttgctcaacc agtcttcata    4200
tcttttttaca acatcattaa ctctctgttt tgcatcggtg tttcccttgt gaaatacctc    4260
ctccactgca ttgatcaaca caccttcaga ttgatgcttt tccggatgga gaataatctt    4320
taccagtctt gacagagtgt ctgctaaaac gttgtccttt ccgtcaatgt gttcaaactt    4380
aatctcaaga cctgtcccgg taatgtaatc tgtgaaggca agccatctga ctcttgatgg    4440
tttatgatca ctgcttttct tgtaaaagct cactattgct tgactgtcag ttctgattat    4500
gagctctttg taagcttggt cacccggtcc gggcctagaa ggccagcttc ggccgccccg    4560
ggcaacttta ttatacaaag ttgatagata tcggaccgat taaactttaa ttcggtccga    4620
agcttgcatg cctgcagtgc agcgtgaccc ggtcgtgccc ctctctagag ataatgagca    4680
ttgcatgtct aagttataaa aaattaccac atattttttt tgtcacactt gtttgaagtg    4740
cagtttatct atctttatac atatatttaa actttactct acgaataata taatctatag    4800
tactacaata atatcagtgt tttagagaat catataaatg aacagttaga catggtctaa    4860
aggacaattg agtatttga caacaggact ctacagtttt atctttttag tgtgcatgtg    4920
ttctcctttt ttttgcaaa tagcttcacc tatataatac ttcatccatt ttattagtac    4980
atccatttag ggtttagggt taatggtttt tatagactaa ttttttttagt acatctattt    5040
tattctattt tagcctctaa attaagaaaa ctaaaactct attttagttt ttttattttaa    5100
taatttagat ataaaataga ataaaataaa gtgactaaaa attaaacaaa tacccctttaa    5160
gaaattaaaa aaactaagga aacatttttc ttgtttcgag tagataatgc cagcctgtta    5220
aacgccgtcg acgagtctaa cggacaccaa ccagcgaacc agcagcgtcg cgtcgggcca    5280
agcgaagcag acggcacggc atctctgtcg ctgcctctgg accccctctcg agagttccgc    5340
tccaccgttg gacttgctcc gctgtcggca tccagaaatt gcgtggcgga gcggcagacg    5400
tgagccggca cggcaggcgg cctcctcctc ctctcacggc accggcagct acggggggatt    5460
cctttcccac cgctccttcg ctttcccttc ctcgcccgcc gtaataaata gacacccccct    5520
ccacaccctc tttccccaac ctcgtgttgt tcggagcgca cacacacaca accagatctc    5580
ccccaaatcc accccgtcggc acctccgctt caaggtacgc cgctcgtcct cccccccccc    5640
cctctctacc ttctctagat cggcgttccg gtccatgcat ggttagggcc cggtagttct    5700
acttctgttc atgtttgtgt tagatccgtg tttgtgttag atccgtgctg ctagcgttcg    5760
tacacggatg cgacctgtac gtcagacacg ttctgattgc taacttgcca gtgtttctct    5820
ttggggaatc ctgggatggc tctagccgtt ccgcagacgg gatcgatttc atgatttttt    5880
ttgtttcgtt gcatagggtt tggtttgccc ttttcctttta tttcaatata tgccgtgcac    5940
ttgtttgtcg ggtcatcttt tcatgctttt ttttgtcttg gttgtgatga tgtggtctgg    6000
```

```
ttgggcggtc gttctagatc ggagtagaat tctgtttcaa actacctggt ggatttatta    6060
attttggatc tgtatgtgtg tgccatacat attcatagtt acgaattgaa gatgatggat    6120
ggaaatatcg atctaggata ggtatacatg ttgatgcggg ttttactgat gcatatacag    6180
agatgctttt tgttcgcttg gttgtgatga tgtggtgtgg ttgggcggtc gttcattcgt    6240
tctagatcgg agtagaatac tgtttcaaac tacctggtgt atttattaat tttggaactg    6300
tatgtgtgtg tcatacatct tcatagttac gagtttaaga tggatggaaa tatcgatcta    6360
ggataggtat acatgttgat gtgggtttta ctgatgcata tacatgatgg catatgcagc    6420
atctattcat atgctctaac cttgagtacc tatctattat aataaacaag tatgttttat    6480
aattattttg atcttgatat acttggatga tggcatatgc agcagctata tgtggatttt    6540
tttagccctg ccttcatacg ctatttattt gcttggtact gtttcttttg tcgatgctca    6600
ccctgttgtt tggtgttact tctgcaggtc gactttaact tagcctagga tccacacgac    6660
accatgtccc ccgagcgccg ccccgtcgag atccgcccgg ccaccgccgc cgacatggcc    6720
gccgtgtgcg acatcgtgaa ccactacatc gagacctcca ccgtgaactt ccgcaccgag    6780
ccgcagaccc cgcaggagtg gatcgacgac ctggagcgcc tccaggaccg ctacccgtgg    6840
ctcgtggccg aggtggaggg cgtggtggcc ggcatcgcct acgccggccc gtggaaggcc    6900
cgcaacgcct acgactggac cgtggagtcc accgtgtacg tgtcccaccg ccaccagcgc    6960
ctcggcctcg gctccaccct ctacacccac ctcctcaaga gcatggaggc ccagggcttc    7020
aagtccgtgg tggccgtgat cggcctcccg aacgacccgt ccgtgcgcct ccacgaggcc    7080
ctcggctaca ccgcccgcgg caccctccgc gccgcggct acaagcacgg cggctggcac    7140
gacgtcggct tctggcagcg cgacttcgag ctgccggccc cgccgcgccc ggtgcgcccg    7200
gtgacgcaga tctgagtcga acctagact tgtccatctt ctggattggc caacttaatt    7260
aatgtatgaa ataaaaggat gcacacatag tgacatgcta atcactataa tgtgggcatc    7320
aaagttgtgt gttatgtgta attactagtt atctgaataa aagagaaaga gatcatccat    7380
atttcttatc ctaaatgaat gtcacgtgtc tttataattc tttgatgaac cagatgcatt    7440
tcattaacca aatccatata catataaata ttaatcatat ataattaata tcaattgggt    7500
tagcaaaaca aatctagtct aggtgtgttt tgcgaatgcg gccgataagt gactagggtc    7560
acgtgaccct agtcacttag gtaccgagct cgaattcatt ccgattaatc gtggcctctt    7620
gctcttcagg atgaagagct atgtttaaac gtgcaagcgc tactagacaa ttcagtacat    7680
taaaaacgtc gcaatgtgt tattaagttg tctaagcgtc aatttgttta caccacaata    7740
tatcctgcca ccagccagcc aacagctccc cgaccggcag ctcggcacaa aatcaccact    7800
cgatacaggc agcccatcag tccgggacgg cgtcagcggg agagccgttg taaggcggca    7860
gactttgctc atgttaccga tgctattcgg aagaacggca actaagctgc cgggtttgaa    7920
acacggatga tctcgcggag ggtagcatgt tgattgtaac gatgacagag cgttgctgcc    7980
tgtgatcaaa tatcatctcc ctcgcagaga tccgaattat cagccttctt attcatttct    8040
cgcttaaccg tgacaggctg tcgatcttga gaactatgcc gacataatag gaaatcgctg    8100
gataaagccg ctgaggaagc tgagtggcgc tatttcttta gaagtgaacg ttgacgatcg    8160
tcgaccgtac cccgatgaat taattcggac gtacgttctg aacacagctg gatacttact    8220
tgggcgattg tcatacatga catcaacaat gtacccgttt gtgtaaccgt ctcttggagg    8280
ttcgtatgac actagtggtt cccctcagct tgcgactaga tgttgaggcc taacatttta    8340
```

```
ttagagagca ggctagttgc ttagatacat gatcttcagg ccgttatctg tcagggcaag    8400
cgaaaattgg ccatttatga cgaccaatgc cccgcagaag ctccatctt tgccgccata     8460 gacgccgcgc ccccctttg gggtgtagaa catccttttg ccagatgtgg aaaagaagtt    8520
cgttgtccca ttgttggcaa tgacgtagta gccggcgaaa gtgcgagacc catttgcgct    8580
atatataagc ctacgatttc cgttgcgact attgtcgtaa ttggatgaac tattatcgta    8640
gttgctctca gagttgtcgt aatttgatgg actattgtcg taattgctta tggagttgtc    8700
gtagttgctt ggagaaatgt cgtagttgga tggggagtag tcatagggaa gacgagcttc    8760
atccactaaa acaattggca ggtcagcaag tgcctgcccc gatgccatcg caagtacgag    8820
gcttagaacc accttcaaca gatcgcgcat agtcttcccc agctctctaa cgcttgagtt    8880
aagccgcgcc gcgaagcggc gtcggcttga acgaattgtt agacattatt tgccgactac    8940
cttggtgatc tcgcctttca cgtagtgaac aaattcttcc aactgatctg cgcgcgaggc    9000
caagcgatct tcttgtccaa gataagcctg cctagcttca agtatgacgg gctgatactg    9060
ggccggcagg cgctccattg cccagtcggc agcgacatcc ttcggcgcga ttttgccggt    9120
tactgcgctg taccaaatgc gggacaacgt aagcactaca tttcgctcat cgccagccca    9180
gtcgggcggc gagttccata cgttaaggt ttcatttagc gcctcaaata gatcctgttc      9240
aggaaccgga tcaaagagtt cctccgccgc tggacctacc aaggcaacgc tatgttctct    9300
tgcttttgtc agcaagatag ccagatcaat gtcgatcgtg gctggctcga agatacctgc    9360
aagaatgtca ttgcgctgcc attctccaaa ttgcagttcg cgcttagctg ataacgcca     9420 cggaatgatg tcgtcgtgca caacaatggt gacttctaca gcgcggagaa tctcgctctc    9480 tccagggaa gccgaagttt ccaaaaggtc gttgatcaaa gctcgccgcg ttgtttcatc      9540
aagccttaca gtcaccgtaa ccagcaaatc aatatcactg tgtggcttca ggccgccatc    9600
cactgcggag ccgtacaaat gtacggccag caacgtcggt tcgagatggc gctcgatgac    9660
gccaactacc tctgatagtt gagtcgatac ttcggcgatc accgcttccc tcatgatgtt    9720
taactcctga attaagccgc gccgcgaagc ggtgtcggct tgaatgaatt gttaggcgtc    9780
atcctgtgct cccgagaacc agtaccagta catcgctgtt tcgttcgaga cttgaggtct    9840
agttttatac gtgaacaggt caatgccgcc gagagtaaag ccacattttg cgtacaaatt    9900
gcaggcaggt acattgttcg tttgtgtctc taatcgtatg ccaaggagct gtctgcttag    9960
tgcccacttt ttcgcaaatt cgatgagact gtgcgcgact cctttgcctc ggtgcgtgtg   10020
cgacacaaca atgtgttcga tagaggctag atcgttccat gttgagttga gttcaatctt   10080
cccgacaagc tcttggtcga tgaatgcgcc atagcaagca gagtcttcat cagagtcatc   10140
atccgagatg taatccttcc ggtaggggct cacacttctg gtagatagtt caaagccttg   10200
gtcggatagg tgcacatcga acacttcacg aacaatgaaa tggttctcag catccaatgt   10260
ttccgccacc tgctcaggga tcaccgaaat cttcatatga cgcctaacgc ctggcacagc   10320
ggatcgcaaa cctggcgcgg cttttggcac aaaaggcgtg acaggtttgc gaatccgttg   10380
ctgccacttg ttaacccttt tgccagattt ggtaactata atttatgtta gaggcgaagt   10440
cttgggtaaa aactgcccta aaattgctgg ggatttcagg aaagtaaaca tcaccttccg   10500
gctcgatgtc tattgtagat atatgtagtg tatctacttg atcgggggat ctgctgcctc   10560
gcgcgtttcg gtgatgacgg tgaaaacctc tgacacatgc agctcccgga gacggtcaca   10620
gcttgtctgt aagcggatgc cgggagcaga caagcccgtc agggcgcgtc agcgggtgtt   10680
ggcgggtgtc ggggcgcagc catgacccag tcacgtagcg atagcggagt gtatactggc   10740
```

```
ttaactatgc ggcatcagag cagattgtac tgagagtgca ccatatgcgg tgtgaaatac  10800
cgcacagatg cgtaaggaga aaataccgca tcaggcgctc ttccgcttcc tcgctcactg  10860
actcgctgcg ctcggtcgtt cggctgcggc gagcggtatc agctcactca aaggcggtaa  10920
tacggttatc cacagaatca ggggataacg caggaaagaa catgtgagca aaaggccagc  10980
aaaaggccag gaaccgtaaa aaggccgcgt tgctggcgtt tttccatagg ctccgccccc  11040
ctgacgagca tcacaaaaat cgacgctcaa gtcagaggtg gcgaaacccg acaggactat  11100
aaagatacca ggcgtttccc cctggaagct ccctcgtgcg ctctcctgtt ccgaccctgc  11160
cgcttaccgg atacctgtcc gcctttctcc cttcgggaag cgtggcgctt tctcatagct  11220
cacgctgtag gtatctcagt tcggtgtagg tcgttcgctc caagctgggc tgtgtgcacg  11280
aaccccccgt tcagcccgac cgctgcgcct tatccggtaa ctatcgtctt gagtccaacc  11340
cggtaagaca cgacttatcg ccactggcag cagccactgg taacaggatt agcagagcga  11400
ggtatgtagg cggtgctaca gagttcttga agtggtggcc taactacggc tacactagaa  11460
ggacagtatt tggtatctgc gctctgctga agccagttac cttcggaaaa agagttggta  11520
gctcttgatc cggcaaacaa accaccgctg gtagcggtgg tttttttgtt tgcaagcagc  11580
agattacgcg cagaaaaaaa ggatctcaag aagatccttt gatcttttct acggggtctg  11640
acgctcagtg gaacgaaaac tcacgttaag ggattttggt catgagatta tcaaaaagga  11700
tcttcaccta gatcctttta aattaaaaat gaagttttaa atcaatctaa agtatatatg  11760
agtaaacttg gtctgacagt taccaatgct taatcagtga ggcacctatc tcagcgatct  11820
gtctatttcg ttcatccata gttgcctgac tccccgtcgt gtagataact acgatacggg  11880
agggcttacc atctggcccc agtgctgcaa tgataccgcg agacccacgc tcaccggctc  11940
cagatttatc agcaataaac cagccagccg gaagggccga gcgcagaagt ggtcctgcaa  12000
ctttatccgc ctccatccag tctattaatt gttgccggga agctagagta agtagttcgc  12060
cagttaatag tttgcgcaac gttgttgcca ttgctgcagg gggggggggg gggggggttcc  12120 attgttcatt ccacggacaa aaacagagaa aggaaacgac agaggccaaa agctcgcctt  12180
tcagcacctg tcgtttcctt tcttttcaga gggtatttta aataaaaaca ttaagttatg  12240
acgaagaaga acggaaacgc cttaaaccgg aaaattttca taaatagcga aaacccgcga  12300
ggtcgccgcc ccgtaacctg tcggatcacc ggaaaggacc cgtaaagtga taatgattat  12360
catctacata tcacaacgtg cgtggaggcc atcaaaccac gtcaaataat caattatgac  12420
gcaggtatcg tattaattga tctgcatcaa cttaacgtaa aaacaacttc agacaataca  12480
aatcagcgac actgaatacg gggcaacctc atgtccccc cccccccccc cctgcaggca  12540
tcgtggtgtc acgctcgtcg tttggtatgg cttcattcag ctccggttcc caacgatcaa  12600
ggcgagttac atgatccccc atgttgtgca aaaaagcggt tagctccttc ggtcctccga  12660
tcgttgtcag aagtaagttg gccgcagtgt tatcactcat ggttatggca gcactgcata  12720
attctcttac tgtcatgcca tccgtaagat gcttttctgt gactggtgag tactcaacca  12780
agtcattctg agaatagtgt atgcggcgac cgagttgctc ttgcccggcg tcaacacggg  12840
ataataccgc gccacatagc agaactttaa aagtgctcat cattggaaaa cgttcttcgg  12900
ggcgaaaact ctcaaggatc ttaccgctgt tgagatccag ttcgatgtaa cccactcgtg  12960
cacccaactg atcttcagca tcttttactt tcaccagcgt ttctgggtga gcaaaaacag  13020
gaaggcaaaa tgccgcaaaa aagggaataa gggcgacacg gaaatgttga atactcatac  13080
```

```
tcttcctttt tcaatattat tgaagcattt atcagggtta ttgtctcatg agcggataca   13140
tatttgaatg tatttagaaa aataaacaaa taggggttcc gcgcacattt ccccgaaaag   13200
tgccacctga cgtctaagaa accattatta tcatgacatt aacctataaa aataggcgta   13260
tcacgaggcc ctttcgtctt caagaattcg gagcttttgc cattctcacc ggattcagtc   13320
gtcactcatg gtgatttctc acttgataac cttattttg acgagggaa attaataggt    13380
tgtattgatg ttggacgagt cggaatcgca gaccgatacc aggatcttgc catcctatgg   13440
aactgcctcg gtgagttttc tccttcatta cagaaacggc ttttcaaaa atatggtatt    13500
gataatcctg atatgaataa attgcagttt catttgatgc tcgatgagtt tttctaatca   13560
gaattggtta attggttgta acactggcag agcattacgc tgacttgacg ggacggcggc   13620
tttgttgaat aaatcgaact tttgctgagt tgaaggatca gatcacgcat cttcccgaca   13680
acgcagaccg ttccgtggca agcaaaagt tcaaaatcac caactggtcc acctacaaca    13740
aagctctcat caaccgtggc tccctcactt tctggctgga tgatggggcg attcaggcct   13800
ggtatgagtc agcaacacct tcttcacgag gcagacctca gcgccagaag gccgccagag   13860
aggccgagcg cggccgtgag gcttggacgc tagggcaggg catgaaaaag cccgtagcgg   13920
gctgctacgg gcgtctgacg cggtggaaag ggggagggga tgttgtctac atggctctgc   13980
tgtagtgagt gggttgcgct ccggcagcgg tcctgatcaa tcgtcaccct ttctcggtcc   14040
ttcaacgttc ctgacaacga gcctcctttt cgccaatcca tcgacaatca ccgcgagtcc   14100
ctgctcgaac gctgcgtccg gaccggcttc gtcgaaggcg tctatcgcgg cccgcaacag   14160
cggcgagagc ggagcctgtt caacggtgcc gccgcgctcg ccggcatcgc tgtcgccggc   14220
ctgctcctca agcacggccc caacagtgaa gtagctgatt gtcatcagcg cattgacggc   14280
gtccccggcc gaaaaacccg cctcgcagag gaagcgaagc tgcgcgtcgg ccgtttccat   14340
ctgcggtgcg cccggtcgcg tgccggcatg gatgcgcgcg ccatcgcggt aggcgagcag   14400
cgcctgcctg aagctgcggg cattcccgat cagaaatgag cgccagtcgt cgtcggctct   14460
cggcaccgaa tgcgtatgat tctccgccag catggcttcg gccagtgcgt cgagcagcgc   14520
ccgcttgttc ctgaagtgcc agtaaagcgc cggctgctga accccaacc gttccgccag    14580
tttgcgtgtc gtcagaccgt ctacgccgac ctcgttcaac aggtccaggg cggcacggat   14640
cactgtattc ggctgcaact ttgtcatgct tgacactta tcactgataa acataatatg    14700
tccaccaact tatcagtgat aaagaatccg cgcgttcaat cggaccagcg gaggctggtc   14760
cggaggccag acgtgaaacc caacataccc ctgatcgtaa ttctgagcac tgtcgcgctc   14820
gacgctgtcg gcatcggcct gattatgccg gtgctgccgg gcctcctgcg cgatctggtt   14880
cactcgaacg acgtcaccgc ccactatggc attctgctgg cgctgtatgc gttggtgcaa   14940
tttgcctgcg cacctgtgct gggcgcgctg tcggatcgtt tcgggcggcg gccaatcttg   15000
ctcgtctcgc tggccggcgc cactgtcgac tacgccatca tggcgacagc gccttttcctt  15060
tgggttctct atatcgggcg gatcgtgcc ggcatcaccg gggcgactgg ggcggtagcc    15120
ggcgcttata ttgccgatat cactgatggc gatgagcgcg cgcggcactt cggcttcatg   15180
agcgcctgtt tcgggttcgg gatggtgcgc ggacctgtgc tcgtgggct gatgggcggt    15240
ttctccccc acgctccgtt cttcgccgcg gcagccttga acggcctcaa tttcctgacg    15300
ggctgtttcc ttttgccgga gtcgcacaaa ggcgaacgcc ggccgttacg ccgggaggct   15360
ctcaacccgc tcgcttcgtt ccggtgggcc cggggcatga ccgtcgtcgc cgccctgatg   15420
gcggtcttct tcatcatgca acttgtcgga caggtgccgg ccgcgctttg ggtcatttc    15480
```

```
ggcgaggatc gctttcactg ggacgcgacc acgatcggca tttcgcttgc cgcatttggc   15540
attctgcatt cactcgccca ggcaatgatc accggccctg tagccgcccg gctcggcgaa   15600
aggcgggcac tcatgctcgg aatgattgcc gacggcacag gctacatcct gcttgccttc   15660
gcgacacggg gatggatggc gttcccgatc atggtcctgc ttgcttcggg tggcatcgga   15720
atgccggcgc tgcaagcaat gttgtccagg caggtggatg aggaacgtca ggggcagctg   15780
caaggctcac tggcggcgct caccagcctg acctcgatcg tcggacccct cctcttcacg   15840
gcgatctatg cggcttctat aacaacgtgg aacgggtggg catggattgc aggcgctgcc   15900
ctctacttgc tctgcctgcc ggcgctgcgt cgcgggcttt ggagcggcgc agggcaacga   15960
gccgatcgct gatcgtggaa acgataggcc tatgccatgc gggtcaaggc gacttccggc   16020
aagctatacg cgccctagga gtgcggttgg aacgttggcc cagccagata ctcccgatca   16080
cgagcaggac gccgatgatt tgaagcgcac tcagcgtctg atccaagaac aaccatccta   16140
gcaacacggc ggtccccggg ctgagaaagc ccagtaagga acaactgta ggttcgagtc   16200 gcgagatccc ccggaaccaa aggaagtagg ttaaacccgc tccgatcagg ccgagccacg   16260
ccaggccgag aacattggtt cctgtaggca tcgggattgg cggatcaaac actaaagcta   16320
ctggaacgag cagaagtcct ccggccgcca gttgccaggc ggtaaaggtg agcagaggca   16380
cgggaggttg ccacttgcgg gtcagcacgg ttccgaacgc catggaaacc gcccccgcca   16440
ggcccgctgc gacgccgaca ggatctagcg ctgcgtttgg tgtcaacacc aacagcgcca   16500
cgcccgcagt tccgcaaata gcccccagga ccgccatcaa tcgtatcggg ctacctagca   16560
gagcggcaga gatgaacacg accatcagcg gctgcacagc gcctaccgtc gccgcgaccc   16620 cgccggcag gcggtagacc gaaataaaca acaagctcca gaatagcgaa atattaagtg   16680
cgccgaggat gaagatgcgc atccaccaga ttcccgttgg aatctgtcgg acgatcatca   16740
cgagcaataa acccgccggc aacgcccgca gcagcatacc ggcgacccct cggcctcgct   16800
gttcgggctc cacgaaaacg ccggacagat gcgccttgtg agcgtccttg gggccgtcct   16860
cctgtttgaa gaccgacagc ccaatgatct cgccgtcgat gtaggcgccg aatgccacgg   16920
catctcgcaa ccgttcagcg aacgcctcca tgggcttttt ctcctcgtgc tcgtaaacgg   16980
acccgaacat ctctggagct ttcttcaggg ccgacaatcg gatctcgcgg aaatcctgca   17040
cgtcggccgc tccaagccgt cgaatctgag ccttaatcac aattgtcaat tttaatcctc   17100
tgtttatcgg cagttcgtag agcgcgccgt gcgtcccgag cgatactgag cgaagcaagt   17160
gcgtcgagca gtgcccgctt gttcctgaaa tgccagtaaa gcgctggctg ctgaaccccc   17220
agccggaact gaccccacaa ggccctagcg tttgcaatgc accaggtcat cattgaccca   17280
ggcgtgttcc accaggccgc tgcctcgcaa ctcttcgcag gcttcgccga cctgctcgcg   17340
ccacttcttc acgcgggtgg aatccgatcc gcacatgagg cggaaggttt ccagcttgag   17400
cgggtacggc tccggtgcg agctgaaata gtcgaacatc cgtcgggccg tcggcgacag   17460
cttgcggtac ttctcccata tgaatttcgt gtagtggtcg ccagcaaaca gcacgacgat   17520
ttcctcgtcg atcaggacct ggcaacggga cgttttcttg ccacggtcca ggacgcggaa   17580
gcggtgcagc agcgacaccg attccaggtg cccaacgcgg tcggacgtga agcccatcgc   17640
cgtcgcctgt aggcgcgaca ggcattcctc ggccttcgtg taataccggc cattgatcga   17700
ccagcccagg tcctggcaaa gctcgtagaa cgtgaaggtg atcggctcgc cgatagggct   17760
gcgcttcgcg tactccaaca cctgctgcca caccagttcg tcatcgtcgg cccgcagctc   17820
```

```
gacgccggtg taggtgatct tcacgtcctt gttgacgtgg aaaatgacct tgttttgcag    17880
cgcctcgcgc gggattttct tgttgcgcgt ggtgaacagg gcagagcggg ccgtgtcgtt    17940
tggcatcgct cgcatcgtgt ccggccacgg cgcaatatcg aacaaggaaa gctgcatttc    18000
cttgatctgc tgcttcgtgt gtttcagcaa cgcggcctgc ttggcctcgc tgacctgttt    18060
tgccaggtcc tcgccggcgg ttttcgctt cttggtcgtc atagttcctc gcgtgtcgat     18120
ggtcatcgac ttcgccaaac ctgccgcctc ctgttcgaga cgacgcgaac gctccacggc    18180
ggccgatggc gcgggcaggg caggggagc cagttgcacg ctgtcgcgct cgatcttggc     18240
cgtagcttgc tggaccatcg agccgacgga ctggaaggtt tcgcggggcg cacgcatgac    18300
ggtgcggctt gcgatggttt cggcatcctc ggcggaaaac cccgcgtcga tcagttcttg    18360
cctgtatgcc ttccggtcaa acgtccgatt cattcaccct ccttgcggga ttgccccgac    18420
tcacgccggg gcaatgtgcc cttattcctg atttgacccg cctggtgcct tggtgtccag    18480
ataatccacc ttatcggcaa tgaagtcggt cccgtagacc gtctggccgt ccttctcgta    18540
cttggtattc cgaatcttgc cctgcacgaa taccagcgac cccttgccca aatacttgcc    18600
gtgggcctcg gcctgagagc caaaacactt gatgcggaag aagtcggtgc gctcctgctt    18660
gtcgccggca tcgttgcgcc actcttcatt aaccgctata tcgaaaattg cttgcggctt    18720
gttagaattg ccatgacgta cctcggtgtc acgggtaaga ttaccgataa actggaactg    18780
attatggctc atatcgaaag tctccttgag aaggagact ctagtttagc taaacattgg     18840
ttccgctgtc aagaacttta gcggctaaaa ttttgcgggc cgcgaccaaa ggtgcgaggg    18900
gcggcttccg ctgtgtacaa ccagatattt ttcaccaaca tccttcgtct gctcgatgag    18960
cggggcatga cgaaacatga gctgtcggag agggcagggg tttcaatttc gtttttatca    19020
gacttaacca acgtaaggc caaccctcg ttgaaggtga tggaggccat tgccgacgcc      19080
ctggaaactc ccctacctct tctcctggag tccaccgacc ttgaccgcga ggcactcgcg    19140
gagattgcgg gtcatccttt caagagcagc gtgccgcccg gatacgaacg catcagtgtg    19200
gttttgccgt cacataaggc gtttatcgta aagaaatggg gcgacgacac ccgaaaaaag    19260
ctgcgtggaa ggctctgacg ccaagggtta gggcttgcac ttccttcttt agccgctaaa    19320
acggccccct tctctgcgggc cgtcggctcg cgcatcatat cgacatcctc aacggaagcc    19380
gtgccgcgaa tggcatcggg cgggtgcgct ttgacagttg ttttctatca gaacccctac    19440
gtcgtgcggt tcgattagct gtttgtcttg caggctaaac actttcggta tatcgtttgc    19500
ctgtgcgata atgttgctaa tgatttgttg cgtaggggtt actgaaaagt gagcgggaaa    19560
gaagagtttc agaccatcaa ggagcgggcc aagcgcaagc tggaacgcga catgggtgcg    19620
gacctgttgg ccgcgctcaa cgacccgaaa accgttgaag tcatgctcaa cgcggacggc    19680
aaggtgtggc acgaacgcct tggcgagccg atgcggtaca tctgcgacat gcggcccagc    19740
cagtcgcagg cgattataga aacggtggcc ggattccacg gcaaagaggt cacgcggcat    19800
tcgcccatcc tggaaggcga gttccccttg gatggcagcc gctttgccgg ccaattgccg    19860
ccggtcgtgg ccgcgccaac ctttgcgatc cgcaagcgcg cggtcgccat cttcacgctg    19920
gaacagtacg tcgaggcggg catcatgacc cgcgagcaat acgaggtcat taaaagcgcc    19980
gtcgcggcgc atcgaaacat cctcgtcatt ggcggtactg gctcgggcaa gaccacgctc    20040
gtcaacgcga tcatcaatga aatggtcgcc ttcaacccgt ctgagcgcgt cgtcatcatc    20100
gaggacaccg gcgaaatcca gtgcgccgca gagaacgccg tccaatacca caccagcatc    20160
gacgtctcga tgacgctgct gctcaagaca acgctgcgta tgcgccccga ccgcatcctg    20220
```

```
gtcggtgagg tacgtggccc cgaagccctt gatctgttga tggcctggaa caccgggcat    20280
gaaggaggtg ccgccaccct gcacgcaaac aaccccaaag cgggcctgag ccggctcgcc    20340
atgcttatca gcatgcaccc ggattcaccg aaacccattg agccgctgat tggcgaggcg    20400
gttcatgtgg tcgtccatat cgccaggacc cctagcggcc gtcgagtgca agaaattctc    20460
gaagttcttg gttacgagaa cggccagtac atcaccaaaa ccctgtaagg agtatttcca    20520 atgcaacgg ctgttccgtt ccgtctgacc atgaatcgcg gcattttgtt ctaccttgcc    20580
gtgttcttcg ttctcgctct cgcgttatcc gcgcatccgg cgatggcctc ggaaggcacc    20640
ggcggcagct tgccatatga gagctggctg acgaacctgc gcaactccgt aaccggcccg    20700
gtggccttcg cgctgtccat catcggcatc gtcgtcgccg gcggcgtgct gatcttcggc    20760
ggcgaactca acgccttctt ccgaaccctg atcttcctgg ttctggtgat ggcgctgctg    20820
gtcggcgcgc agaacgtgat gagcaccttc ttcggtcgtg gtgccgaaat cgcggccctc    20880
ggcaacgggg cgctgcacca ggtgcaagtc gcggcggcgg atgccgtgcg tgcggtagcg    20940
gctggacggc tcgcctaatc atggctctgc gcacgatccc catccgtcgc gcaggcaacc    21000
gagaaaacct gttcatgggt ggtgatcgtg aactggtgat gttctcgggc ctgatggcgt    21060
ttgcgctgat tttcagcgcc caagagctgc gggccaccgt ggtcggtctg atcctgtggt    21120
tcggggcgct ctatgcgttc cgaatcatgg cgaaggccga tccgaagatg cggttcgtgt    21180
acctgcgtca ccgccggtac aagccgtatt acccggcccg ctcgaccccg ttccgcgaga    21240
acaccaatag ccaagggaag caataccgat gatccaagca attgcgattg caatcgcggg    21300
cctcggcgcg cttctgttgt tcatcctctt tgcccgcatc cgcgcggtcg atgccgaact    21360
gaaactgaaa aagcatcgtt ccaaggacgc cggcctggcc gatctgctca actacgccgc    21420
tgtcgtcgat gacggcgtaa tcgtgggcaa gaacggcagc tttatggctg cctggctgta    21480
caagggcgat gacaacgcaa gcagcaccga ccagcagcgc gaagtagtgt ccgcccgcat    21540
caaccaggcc ctcgcgggcc tgggaagtgg gtggatgatc catgtggacg ccgtgcggcg    21600
tcctgctccg aactacgcgg agcggggcct gtcggcgttc cctgaccgtc tgacggcagc    21660
gattgaagaa gagcgctcgg tcttgccttg ctcgtcggtg atgtacttca ccagctccgc    21720
gaagtcgctc ttcttgatgg agcgcatggg gacgtgcttg gcaatcacgc gcaccccccg    21780
gccgttttag cggctaaaaa agtcatggct ctgccctcgg gcggaccacg cccatcatga    21840
ccttgccaag ctcgtcctgc ttctcttcga tcttcgccag cagggcgagg atcgtggcat    21900
caccgaaccg cgccgtgcgc gggtcgtcgg tgagccagag tttcagcagg ccgcccaggc    21960
ggcccaggtc gccattgatg cgggccagct cgcggacgtg ctcatagtcc acgacgcccg    22020
tgattttgta gccctggccg acggccagca ggtaggccga caggctcatg ccggccgccg    22080
ccgccttttc ctcaatcgct cttcgttcgt ctggaaggca gtacaccttg ataggtgggc    22140
tgcccttcct ggttggcttg gtttcatcag ccatccgctt gccctcatct gttacgccgg    22200
cggtagccgg ccagcctcgc agagcaggat tcccgttgag caccgccagg tgcgaataag    22260
ggacagtgaa gaaggaacac ccgctcgcgg gtgggcctac ttcacctatc ctgcccggct    22320
gacgccgttg gatacaccaa ggaaagtcta cacgaaccct ttggcaaaat cctgtatatc    22380
gtgcgaaaaa ggatggatat accgaaaaaa tcgctataat gaccccgaag cagggttatg    22440
cagcggaaaa gcgctgcttc cctgctgttt tgtggaatat ctaccgactg gaaacaggca    22500
aatgcaggaa attactgaac tgaggggaca ggcgagagac gatgccaaag agctacaccg    22560
```

```
acgagctggc cgagtgggtt gaatcccgcg cggccaagaa gcgccggcgt gatgaggctg   22620
cggttgcgtt cctggcggtg agggcggatg tcgaggcggc gttagcgtcc ggctatgcgc   22680
tcgtcaccat ttgggagcac atgcgggaaa cggggaaggt caagttctcc tacgagacgt   22740
tccgctcgca cgccaggcgg cacatcaagg ccaagcccgc cgatgtgccc gcaccgcagg   22800
ccaaggctgc ggaacccgcg ccggcaccca agacgccgga gccacggcgg ccgaagcagg   22860
ggggcaaggc tgaaaagccg gcccccgctg cggccccgac cggcttcacc ttcaacccaa   22920
caccggacaa aaaggatcta ctgtaatggc gaaaattcac atggttttgc agggcaaggg   22980
cggggtcggc aagtcggcca tcgccgcgat cattgcgcag tacaagatgg acaaggggca   23040
gacacccttg tgcatcgaca ccgacccggt gaacgcgacg ttcgagggct acaaggccct   23100
gaacgtccgc cggctgaaca tcatggccgg cgacgaaatt aactcgcgca acttcgacac   23160
cctggtcgag ctgattgcgc cgaccaagga tgacgtggtg atcgacaacg gtgccagctc   23220
gttcgtgcct ctgtcgcatt acctcatcag caaccaggtg ccggctctgc tgcaagaaat   23280
ggggcatgag ctggtcatcc ataccgtcgt caccggcggc caggctctcc tggacacggt   23340
gagcggcttc gcccagctcg ccagccagtt cccggccgaa gcgcttttcg tggtctggct   23400
gaacccgtat tgggggccta tcgagcatga gggcaagagc tttgagcaga tgaaggcgta   23460
cacggccaac aaggcccgcg tgtcgtccat catccagatt ccggccctca aggaagaaac   23520
ctacggccgc gatttcagcg acatgctgca agagcggctg acgttcgacc aggcgctggc   23580
cgatgaatcg ctcacgatca tgacgcggca acgcctcaag atcgtgcggc gcggcctgtt   23640
tgaacagctc gacgcggcgg ccgtgctatg agcgaccaga ttgaagagct gatccgggag   23700
attgcggcca agcacggcat cgccgtcggc cgcgacgacc cggtgctgat cctgcatacc   23760
atcaacgccc ggctcatggc cgacagtgcg gccaagcaag aggaaatcct tgccgcgttc   23820
aaggaagagc tggaagggat cgcccatcgt tggggcgagg acgccaaggc caaagcggag   23880
cggatgctga acgcggccct ggcggccagc aaggacgcaa tggcgaaggt aatgaaggac   23940
agcgccgcgc aggcggccga agcgatccgc agggaaatcg acgacggcct tggccgccag   24000
ctcgcggcca aggtcgcgga cgcgcggcgc gtggcgatga tgaacatgat cgccggcggc   24060
atggtgttgt tcgcggccgc cctggtggtg tgggcctcgt tatgaatcgc agaggcgcag   24120
atgaaaaagc ccggcgttgc cgggctttgt ttttgcgtta gctgggcttg tttgacaggc   24180
ccaagctctg actgcgcccg cgctcgcgct cctgggcctg tttcttctcc tgctcctgct   24240
tgcgcatcag ggcctggtgc cgtcgggctg cttcacgcat cgaatcccag tcgccggcca   24300
gctcgggatg ctccgcgcgc atcttgcgcg tcgccagttc ctcgatcttg ggcgcgtgaa   24360
tgcccatgcc ttccttgatt tcgcgcacca tgtccagccg cgtgtgcagg tctgcaagc    24420 gggcttgctg ttgggcctgc tgctgctgcc aggcggcctt tgtacgcggc agggacagca   24480
agccgggggc attggactgt agctgctgca aacgcgcctg ctgacggtct acgagctgtt   24540
ctaggcggtc ctcgatgcgc tccacctggt catgcttttgc ctgcacgtag agcgcaaggg   24600
tctgctggta ggtctgctcg atgggcgcgg attctaagag ggcctgctgt tccgtctcgg   24660
cctcctgggc cgcctgtagc aaatcctcgc cgctgttgcc gctggactgc tttactgccg   24720
gggactgctg ttgccctgct cgcgccgtcg tcgcagttcg gcttgccccc actcgattga   24780
ctgcttcatt tcgagccgca gcgatgcgat ctcggattgc gtcaacggac ggggcagcgc   24840
ggaggtgtcc ggcttctcct tgggtgagtc ggtcgatgcc atagccaaag gtttccttcc   24900
aaaatgcgtc cattgctgga ccgtgtttct cattgatgcc cgcaagcatc ttcggcttga   24960
```

```
ccgccaggtc aagcgcgcct tcatgggcgg tcatgacgga cgccgccatg accttgccgc   25020
cgttgttctc gatgtagccg cgtaatgagg caatggtgcc gcccatcgtc agcgtgtcat   25080
cgacaacgat gtacttctgg ccggggatca cctcccctc gaaagtcggg ttgaacgcca   25140
ggcgatgatc tgaaccggct ccggttcggg cgaccttctc ccgctgcaca atgtccgttt   25200
cgacctcaag gccaaggcgg tcggccagaa cgaccgccat catggccgga tcttgttgt    25260 tccccgccgc ctcgacggcg aggactgaa cgatgcgggg cttgtcgtcg ccgatcagcg    25320
tcttgagctg ggcaacagtg tcgtccgaaa tcaggcgctc gaccaaatta agcgccgctt   25380
ccgcgtcgcc ctgcttcgca gcctggtatt caggctcgtt ggtcaaagaa ccaaggtcgc   25440
cgttgcgaac caccttcggg aagtctcccc acggtgcgcg ctcggctctg ctgtagctgc   25500
tcaagacgcc tccttttta gccgctaaaa ctctaacgag tgcgcccgcg actcaacttg    25560
acgctttcgg cacttacctg tgccttgcca cttgcgtcat aggtgatgct tttcgcactc   25620
ccgatttcag gtactttatc gaaatctgac cgggcgtgca ttacaaagtt cttccccacc   25680
tgttggtaaa tgctgccgct atctgcgtgg acgatgctgc cgtcgtggcg ctgcgactta   25740
tcggcctttt gggccatata gatgttgtaa atgccaggtt tcagggcccc ggctttatct   25800
accttctggt tcgtccatgc gccttggttc tcggtctgga caattctttg cccattcatg   25860
accaggaggc ggtgtttcat tgggtgactc ctgacggttg cctctggtgt taaacgtgtc   25920
ctggtcgctt gccggctaaa aaaaagccga cctcggcagt tcgaggccgg ctttccctag   25980
agccgggcgc gtcaaggttg ttccatctat tttagtgaac tgcgttcgat ttatcagtta   26040 cttttcctccc gctttgtgtt tcctcccact cgtttccgcg tctagccgac ccctcaacat   26100
agcggcctct tcttgggctg cctttgcctc ttgccgcgct tcgtcacgct cggcttgcac   26160
cgtcgtaaag cgctcggcct gcctggccgc ctcttgcgcc gccaacttcc tttgctcctg   26220
gtgggcctcg gcgtcggcct gcgccttcgc tttcaccgct gccaactccg tgcgcaaact   26280
ctccgcttcg cgcctggtgg cgtcgcgctc gccgcgaagc gcctgcattt cctggttggc   26340
cgcgtccagg gtcttgcggc tctcttcttt gaatgcgcgg gcgtcctggt gagcgtagtc   26400
cagctcggcg cgcagctcct gcgctcgacg ctccacctcg tcggcccgct gcgtcgccag   26460
cgcggcccgc tgctcggctc ctgccagggc ggtgcgtgct tcggcagggg cttgccgctg   26520
gcgtgcggcc agctcggccg cctcggcggc ctgctgctct agcaatgtaa cgcgcgcctg   26580
ggcttcttcc agctcgcggg cctgcgcctc gaaggcgtcg gccagctccc gcgcacggc    26640 ttccaactcg ttgcgctcac gatcccagcc ggcttgcgct gcctgcaacg attcattggc   26700
aagggcctgg gcggcttgcc agagggcggc cacggcctgg ttgccggcct gctgcaccgc   26760
gtccggcacc tggactgcca gcggggcggc ctgcgccgtg cgctggcgtc gccattcgcg   26820
catgccggcg ctggcgtcgt tcatgttgac gcgggcggcc ttacgcactg catccacggt   26880
cgggaagttc tcccgtcgc cttgctcgaa cagctcgtcc gcagccgcaa aaatgcggtc    26940
gcgcgtctct ttgttcagtt ccatgttggc tccggtaatt ggtaagaata ataatactct   27000
tacctacctt atcagcgcaa gagtttagct gaacagttct cgacttaacg gcaggttttt   27060
tagcggctga agggcaggca aaaaaagccc cgcacggtcg gcggggcaa agggtcagcg    27120 ggaagggat tagcgggcgt cgggcttctt catgcgtcgg ggccgcgctt cttgggatgg    27180
agcacgacga agcgcgcacg cgcatcgtcc tcggccctat cggccgcgt cgcggtcagg    27240 aacttgtcgc gcgctaggtc ctccctggtg ggcaccaggg gcatgaactc ggcctgctcg   27300
```

```
atgtaggtcc actccatgac cgcatcgcag tcgaggccgc gttccttcac cgtctcttgc    27360
aggtcgcggt acgcccgctc gttgagcggc tggtaacggg ccaattggtc gtaaatggct    27420
gtcggccatg agcggccttt cctgttgagc cagcagccga cgacgaagcc ggcaatgcag    27480
gcccctggca caaccaggcc gacgccgggg cagggatg gcagcagctc gccaaccagg     27540
aaccccgccg cgatgatgcc gatgccggtc aaccagccct tgaaactatc cggccccgaa    27600
acacccctgc gcattgcctg gatgctgcgc cggatagctt gcaacatcag gagccgtttc    27660
ttttgttcgt cagtcatggt ccgccctcac cagttgttcg tatcggtgtc ggacgaactg    27720
aaatcgcaag agctgccggt atcggtccag ccgctgtccg tgtcgctgct gccgaagcac    27780 ggcgagggt ccgcgaacgc cgcagacggc gtatccggcc gcagcgcatc gcccagcatg     27840
gccccggtca gcgagccgcc ggccaggtag cccagcatgg tgctgttggt cgccccggcc    27900
accagggccg acgtgacgaa atcgccgtca ttccctctgg attgttcgct gctcggcggg    27960
gcagtgcgcc gcgccggcgg cgtcgtggat ggctcgggtt ggctggcctg cgacggccgg    28020
cgaaaggtgc gcagcagctc gttatcgacc ggctgcggcg tcgggccgc cgccttgcgc     28080 tgcggtcggt gttccttctt cggctcgcgc agcttgaaca gcatgatcgc ggaaaccagc    28140
agcaacgccg cgcctacgcc tcccgcgatg tagaacagca tcggattcat tcttcggtcc    28200
tccttgtagc ggaaccgttg tctgtgcggc gcgggtggcc cgcgccgctg tctttgggga    28260
tcagccctcg atgagcgcga ccagtttcac gtcggcaagg ttcgcctcga actcctggcc    28320
gtcgtcctcg tacttcaacc aggcatagcc ttccgccggc ggccgacggt tgaggataag    28380
gcgggcaggg cgctcgtcgt gctcgacctg gacgatggcc tttttcagct tgtccgggtc    28440
cggctccttc gcgccctttt ccttggcgtc cttaccgtcc tggtcgccgt cctcgccgtc    28500
ctggccgtcg ccgcctccg cgtcacgctc ggcatcagtc tggccgttga aggcatcgac      28560
ggtgttggga tcgcggccct tctcgtccag gaactcgcgc agcagcttga ccgtgccgcg    28620
cgtgatttcc tgggtgtcgt cgtcaagcca cgcctcgact tcctccgggc gcttcttgaa    28680
ggccgtcacc agctcgttca ccacggtcac gtcgcgcacg cggccggtgt tgaacgcatc    28740
ggcgatcttc tccggcaggt ccagcagcgt gacgtgctgg gtgatgaacg ccggcgactt    28800
gccgatttcc ttggcgatat cgcctttctt cttgcccttc gccagctcgc ggccaatgaa    28860
gtcggcaatt tcgcgcgggg tcagctcgtt gcgttgcagg ttctcgataa cctggtcggc    28920
ttcgttgtag tcgttgtcga tgaacgccgg gatggacttc ttgccggccc acttcgagcc    28980
acggtagcgg cgggcgccgt gattgatgat atagcggccc ggctgctcct ggttctcgcg    29040
caccgaaatg ggtgacttca ccccgcgctc tttgatcgtg gcaccgattt ccgcgatgct    29100
ctccggggaa aagccgggt tgtcggccgt ccgcggctga tgcggatctt cgtcgatcag     29160
gtccaggtcc agctcgatag ggccggaacc gccctgagac gccgcaggag cgtccaggag    29220
gctcgacagg tcgccgatgc tatccaaccc caggccggac ggctgcgccg cgcctgcggc    29280
ttcctgagcg gccgcagcgg tgttttttctt ggtggtcttg gcttgagccg cagtcattgg    29340
gaaatctcca tcttcgtgaa cacgtaatca gccagggcgc gaacctcttt cgatgccttg    29400
cgcgcggccg ttttcttgat cttccagacc ggcacaccgg atgcgagggc atcgcgatg    29460 ctgctgcgca ggccaacggt ggccggaatc atcatcttgg ggtacgcggc cagcagctcg    29520
gcttggtggc gcgcgtggcg cggattccgc gcatcgacct tgctgggcac catgccaagg    29580
aattgcagct ggcgttctt ctggcgcacg ttcgcaatgg tcgtgaccat cttcttgatg     29640
ccctggatgc tgtacgcctc aagctcgatg ggggacagca catagtcggc cgcgaagagg    29700
```

```
gcggccgcca ggccgacgcc aagggtcggg gccgtgtcga tcaggcacac gtcgaagcct   29760
tggttcgcca gggccttgat gttcgccccg aacagctcgc gggcgtcgtc cagcgacagc   29820
cgttcggcgt tcgccagtac cgggttggac tcgatgaggg cgaggcgcgc ggcctggccg   29880
tcgccggctg cgggtgcggt ttcggtccag ccgccggcag ggacagcgcc gaacagcttg   29940
cttgcatgca ggccggtagc aaagtccttg agcgtgtagg acgcattgcc ctggggtcc    30000 aggtcgatca cggcaacccg caagccgcgc tcgaaaaagt cgaaggcaag atgcacaagg   30060
gtcgaagtct tgccgacgcc gcctttctgg ttggccgtga ccaaagtttt catcgtttgg   30120
tttcctgttt tttcttggcg tccgcttccc acttccggac gatgtacgcc tgatgttccg   30180
gcagaaccgc cgttacccgc gcgtacccct cgggcaagtt cttgtcctcg aacgcggccc   30240
acacgcgatg caccgcttgc gacactgcgc ccctggtcag tcccagcgac gttgcgaacg   30300
tcgcctgtgg cttcccatcg actaagacgc cccgcgctat ctcgatggtc tgctgcccca   30360
cttccagccc ctggatcgcc tcctggaact ggctttcggt aagccgtttc ttcatggata   30420
acacccataa tttgctccgc gccttggttg aacatagcgg tgacagccgc cagcacatga   30480
gagaagttta gctaaacatt tctcgcacgt caacacctttt agccgctaaa actcgtcctt   30540
ggcgtaacaa aacaaaagcc cggaaaccgg gctttcgtct cttgccgctt atggctctgc   30600
acccggctcc atcaccaaca ggtcgcgcac gcgcttcact cggttgcgga tcgacactgc   30660
cagcccaaca aagccggttg ccgccgccgc caggatcgcg ccgatgatgc cggccacacc   30720
ggccatcgcc caccaggtcg ccgccttccg gttccattcc tgctggtact gcttcgcaat   30780
gctggacctc ggctcaccat aggctgaccg ctcgatggcg tatgccgctt ctccccttgg   30840
cgtaaaaccc agcgccgcag gcggcattgc catgctgccc gccgctttcc cgaccacgac   30900
gcgcgcacca ggcttgcggt ccagaccttc ggccacggca agctgcgcaa ggacataatc   30960
agccgccgac ttggctccac gcgcctcgat cagctcttgc actcgcgcga aatccttggc   31020
ctccacggcc gccatgaatc gcgcacgcgg cgaaggctcc gcagggccgg cgtcgtgatc   31080
gccgccgaga atgcccttca ccaagttcga cgacacgaaa atcatgctga cggctatcac   31140
catcatgcag acgatcgca cgaacccgct gaattgaaca cgagcacggc acccgcgacc   31200
actatgccaa gaatgcccaa ggtaaaaatt gccggccccg ccatgaagtc cgtgaatgcc   31260
ccgacggccg aagtgaaggg caggccgcca cccaggccgc cgccctcact gcccggcacc   31320
tggtcgctga atgtcgatgc cagcacctgc ggcacgtcaa tgcttccggg cgtcgcgctc   31380
gggctgatcg cccatcccgt tactgccccg atcccggcaa tggcaaggac tgccagcgct   31440 gccattttg gggtgaggcc gttcgcggcc gaggggcgca gccctgggg ggatgggagg    31500 cccgcgttag cgggccggga gggttcgaga aggggggca ccccccttcg gcgtgcgcgg    31560
tcacgcgcac agggcgcagc cctggttaaa aacaaggttt ataaatattg gtttaaaagc   31620
aggttaaaag acaggttagc ggtggccgaa aaacggcgg aaaccttgc aaatgctgga     31680 ttttctgcct gtggacagcc cctcaaatgt caataggtgc gcccctcatc tgtcagcact   31740
ctgcccctca agtgtcaagg atcgcgcccc tcatctgtca gtagtcgcgc ccctcaagtg   31800
tcaataccgc agggcactta tccccaggct tgtccacatc atctgtggga aactcgcgta   31860
aaatcaggcg ttttcgccga tttgcgaggc tggccagctc cacgtcgccg gccgaaatcg   31920 agcctgccc tcatctgtca acgccgcgcc gggtgagtcg gccctcaag tgtcaacgtc     31980 cgcccctcat ctgtcagtga gggccaagtt ttccgcgagg tatccacaac gccggcggcc   32040
```

```
gcggtgtctc gcacacggct tcgacggcgt ttctggcgcg tttgcagggc catagacggc    32100
cgccagccca gcggcgaggg caaccagccc ggtgagcgtc ggaaaggcgc tggaagcccc    32160
gtagcgacgc ggagaggggc gagacaagcc aagggcgcag gctcgatgcg cagcacgaca    32220
tagccggttc tcgcaaggac gagaatttcc ctgcggtgcc cctcaagtgt caatgaaagt    32280
ttccaacgcg agccattcgc gagagccttg agtccacgct agatgagagc tttgttgtag    32340
gtggaccagt tggtgatttt gaactttgc tttgccacgg aacggtctgc gttgtcggga    32400
agatgcgtga tctgatcctt caactcagca aaagttcgat ttattcaaca aagccacgtt    32460
gtgtctcaaa atctctgatg ttacattgca caagataaaa atatatcatc atgaacaata    32520
aaactgtctg cttacataaa cagtaataca aggggtgtta tgagccatat caacgggaa    32580 acgtcttgct cgactctaga gctcgttcct cgaggcctcg aggcctcgag gaacggtacc    32640 tgcgggaag cttacaataa tgtgtgttgt taagtcttgt tgcctgtcat cgtctgactg    32700
actttcgtca taaatcccgg cctccgtaac ccagctttgg gcaagctcac ggatttgatc    32760
cggcggaacg ggaatatcga gatgccgggc tgaacgctgc agttccagct ttccctttcg    32820
ggacaggtac tccagctgat tgattatctg ctgaagggtc ttggttccac ctcctggcac    32880
aatgcgaatt attacttgag cgcgatcggg catccaattt tctcccgtca ggtgcgtggt    32940
caagtgctac aaggcacctt tcagtaacga gcgaccgtcg atccgtcgcc gggatacgga    33000
caaaatggag cgcagtagtc catcgagggc ggcgaaagcc tcgccaaaag caatacgttc    33060
atctcgcaca gcctccagat ccgatcgagg gtcttcggcg taggcagata gaagcatgga    33120
tacattgctt gagagtattc cgatggactg aagtatggct tccatctttt ctcgtgtgtc    33180
tgcatctatt tcgagaaagc ccccgatgcg gcgcaccgca acgcgaattg ccatactatc    33240
cgaaagtccc agcaggcgcg cttgatagga aaaggtttca tactcggccg atcgcagacg    33300
ggcactcacg accttgaacc cttcaacttt cagggatcga tgctggttga tggtagtctc    33360
actcgacgtg gctctggtgt gttttgacat agcttcctcc aaagaaagcg gaaggtctgg    33420
atactccagc acgaaatgtg cccgggtaga cggatggaag tctagccctg ctcaatatga    33480
aatcaacagt acatttacag tcaatactga atatacttgc tacatttgca attgtcttat    33540
aacgaatgtg aaataaaaat agtgtaacaa cgcttttact catcgataat cacaaaaaca    33600
tttatacgaa caaaaataca aatgcactcc ggtttcacag gataggcggg atcagaatat    33660
gcaacttttg acgttttgtt ctttcaaagg gggtgctggc aaaaccaccg cactcatggg    33720
cctttgcgct gctttggcaa atgacggtaa acgagtggcc ctctttgatg ccgacgaaaa    33780
ccggcctctg acgcgatgga gagaaaacgc cttacaaagc agtactggga tcctcgctgt    33840
gaagtctatt ccgccgacga aatgcccctt cttgaagcag cctatgaaaa tgccgagctc    33900
gaaggatttg attatgcgtt ggccgatacg cgtggcggct cgagcgagct caacaacaca    33960
atcatcgcta gctcaaacct gcttctgatc cccaccatgc taacgccgct cgacatcgat    34020
gaggcactat ctacctaccg ctacgtcatc gagctgctgt tgagtgaaaa tttggcaatt    34080
cctacagctg ttttgcgcca acgcgtcccg gtcggccgat tgacaacatc gcaacgcagg    34140
atgtcagaga cgctagagag ccttccagtt gtaccgtctc ccatgcatga aagagatgca    34200
tttgccgcga tgaaagaacg cggcatgttg catcttacat tactaaacac gggaactgat    34260
ccgacgatgc gcctcataga gaggaatctt cggattgcga tggaggaagt cgtggtcatt    34320
tcgaaactga tcagcaaaat cttggaggct tgaagatggc aattcgcaag cccgcattgt    34380
cggtcggcga agcacggcgg cttgctggtg ctcgacccga gatccaccat cccaacccga    34440
```

```
cacttgttcc ccagaagctg gacctccagc acttgcctga aaagccgac gagaaagacc    34500 agcaacgtga gcctctcgtc gccgatcaca tttacagtcc cgatcgacaa cttaagctaa    34560
ctgtggatgc ccttagtcca cctccgtccc cgaaaaagct ccaggttttt ctttcagcgc    34620
gaccgcccgc gcctcaagtg tcgaaaacat atgacaacct cgttcggcaa tacagtccct    34680
cgaagtcgct acaaatgatt ttaaggcgcg cgttggacga tttcgaaagc atgctggcag    34740
atggatcatt tcgcgtggcc ccgaaaagtt atccgatccc ttcaactaca gaaaaatccg    34800
ttctcgttca gacctcacgc atgttcccgg ttgcgttgct cgaggtcgct cgaagtcatt    34860
ttgatccgtt ggggttggag accgctcgag ctttcggcca caagctggct accgccgcgc    34920
tcgcgtcatt ctttgctgga gagaagccat cgagcaattg gtgaagaggg acctatcgga    34980
acccctcacc aaatattgag tgtaggtttg aggccgctgg ccgcgtcctc agtcacctt    35040 tgagccagat aattaagagc caaatgcaat tggctcaggc tgccatcgtc ccccgtgcg    35100 aaacctgcac gtccgcgtca aagaaataac cggcacctct tgctgttttt atcagttgag    35160
ggcttgacgg atccgcctca gtttgcggc gcagccgcaa aatgagaaca tctatactcc    35220
tgtcgtaaac ctcctcgtcg cgtactcgac tggcaatgag aagttgctcg cgcgatagaa    35280
cgtcgcgggg tttctctaaa aacgcgagga gaagattgaa ctcacctgcc gtaagtttca    35340
cctcaccgcc agcttcggac atcaagcgac gttgcctgag attaagtgtc cagtcagtaa    35400
aacaaaaaga ccgtcggtct ttggagcgga caacgttggg gcgcacgcgc aaggcaaccc    35460
gaatgcgtgc aagaaactct ctcgtactaa acggcttagc gataaaatca cttgctccta    35520
gctcgagtgc aacaacttta tccgtctcct caaggcggtc gccactgata attatgattg    35580
gaatatcaga ctttgccgcc agatttcgaa cgatctcaag cccatcttca cgacctaaat    35640
ttagatcaac aaccacgaca tcgaccgtcg cggaagagag tactctagtg aactgggtgc    35700
tgtcggctac cgcggtcact ttgaaggcgt ggatcgtaag gtattcgata taagatgcc    35760 gcatagcgac atcgtcatcg ataagaagaa cgtgtttcaa cggctcacct ttcaatctaa    35820
aatctgaacc cttgttcaca gcgcttgaga aattttcacg tgaaggatgt acaatcatct    35880
ccagctaaat gggcagttcg tcagaattgc ggctgaccgc ggatgacgaa aatgcgaacc    35940
aagtatttca attttatgac aaaagttctc aatcgttgtt acaagtgaaa cgcttcgagg    36000
ttacagctac tattgattaa ggagatcgcc tatggtctcg ccccggcgtc gtgcgtccgc    36060
cgcgagccag atctcgccta cttcataaac gtcctcatag gcacggaatg gaatgatgac    36120
atcgatcgcc gtagagagca tgtcaatcag tgtgcgatct tccaagctag caccttgggc    36180 gctactttg acaagggaaa acagtttctt gaatccttgg attggattcg cgccgtgtat    36240
tgttgaaatc gatcccggat gtcccagac gacttcactc agataagccc atgctgcatc    36300
gtcgcgcatc tcgccaagca atatccggtc cggccgcata cgcagacttg cttggagcaa    36360
gtgctcggcg ctcacagcac ccagcccagc accgttcttg gagtagagta gtctaacatg    36420
attatcgtgt ggaatgacga gttcgagcgt atcttctatg gtgattagcc tttcctgggg    36480
ggggatggcg ctgatcaagg tcttgctcat tgttgtcttg ccgcttccgg tagggccaca    36540
tagcaacatc gtcagtcggc tgacgacgca tgcgtgcaga aacgcttcca aatcccgtt    36600 gtcaaaatgc tgaaggatag cttcatcatc ctgattttgg cgtttccttc gtgtctgcca    36660
ctggttccac ctcgaagcat cataacggga ggagacttct ttaagaccag aaacacgcga    36720
gcttggccgt cgaatggtca agctgacggt gcccgaggga acggtcggcg gcagacagat    36780
```

-continued

| | |
|---|---|
| ttgtagtcgt tcaccaccag gaagttcagt ggcgcagagg gggttacgtg gtccgacatc | 36840 |
| ctgctttctc agcgcgcccg ctaaaatagc gatatcttca agatcatcat aagagacggg | 36900 |
| caaaggcatc ttggtaaaaa tgccggcttg gcgcacaaat gcctctccag gtcgattgat | 36960 |
| cgcaatttct tcagtcttcg ggtcatcgag ccattccaaa atcggcttca gaagaaagcg | 37020 |
| tagttgcgga tccacttcca tttacaatgt atcctatctc taagcggaaa tttgaattca | 37080 |
| ttaagagcgg cggttcctcc cccgcgtggc gccgccagtc aggcggagct ggtaaacacc | 37140 |
| aaagaaatcg aggtcccgtg ctacgaaaat ggaaacggtg tcaccctgat tcttcttcag | 37200 |
| ggttggcggt atgttgatgg ttgccttaag ggctgtctca gttgtctgct caccgttatt | 37260 |
| ttgaaagctg ttgaagctca tcccgccacc cgagctgccg gcgtaggtgc tagctgcctg | 37320 |
| gaaggcgcct tgaacaacac tcaagagcat agctccgcta aaacgctgcc agaagtggct | 37380 |
| gtcgaccgag cccggcaatc ctgagcgacc gagttcgtcc gcgcttggcg atgttaacga | 37440 |
| gatcatcgca tggtcaggtg tctcggcgcg atcccacaac acaaaaacgc gcccatctcc | 37500 |
| ctgttgcaag ccacgctgta tttcgccaac aacggtggtg ccacgatcaa gaagcacgat | 37560 |
| attgttcgtt gttccacgaa tatcctgagg caagacacac tttacatagc ctgccaaatt | 37620 |
| tgtgtcgatt gcggtttgca agatgcacgg aattattgtc ccttgcgtta ccataaaatc | 37680 |
| ggggtgcggc aagagcgtgg cgctgctggg ctgcagctcg gtgggtttca tacgtatcga | 37740 |
| caaatcgttc tcgccggaca cttcgccatt cggcaaggag ttgtcgtcac gcttgccttc | 37800 |
| ttgtcttcgg cccgtgtcgc cctgaatggc gcgtttgctg accccttgat cgccgctgct | 37860 |
| atatgcaaaa atcggtgttt cttccggccg tggctcatgc cgctccggtt cgcccctcgg | 37920 |
| cggtagagga gcagcaggct gaacagcctc ttgaaccgct ggaggatccg gcggcacctc | 37980 |
| aatcggagct ggatgaaatg gcttggtgtt tgttgcgatc aaagttgacg gcgatgcgtt | 38040 |
| ctcattcacc ttcttttggc gcccacctag ccaaatgagg cttaatgata acgcgagaac | 38100 |
| gacacctccg acgatcaatt tctgagaccc gaaagacgc cggcgatgtt tgtcggagac | 38160 |
| cagggatcca gatgcatcaa cctcatgtgc cgcttgctga ctatcgttat tcatcccttc | 38220 |
| gccccttca ggacgcgttt cacatcgggc ctcaccgtgc ccgtttgcgg cctttggcca | 38280 |
| acgggatcgt aagcggtgtt ccagatacat agtactgtgt ggccatccct cagacgccaa | 38340 |
| cctcgggaaa ccgaagaaat ctcgacatcg ctcccttaa ctgaatagtt ggcaacagct | 38400 |
| tccttgccat caggattgat ggtgtagatg gagggtatgc gtacattgcc cggaaagtgg | 38460 |
| aataccgtcg taaatccatt gtcgaagact tcgagtggca acagcgaacg atcgccttgg | 38520 |
| gcgacgtagt gccaattact gtccgccgca ccaagggctg tgacaggctg atccaataaa | 38580 |
| ttctcagctt tccgttgata ttgtgcttcc gcgtgtagtc tgtccacaac agccttctgt | 38640 |
| tgtgcctccc ttcgccgagc cgccgcatcg tcggcggggt aggcgaattg gacgctgtaa | 38700 |
| tagagatcgg gctgctcttt atcgaggtgg gacagagtct tggaacttat actgaaaaca | 38760 |
| taacggcgca tcccggagtc gcttgcggtt agcacgatta ctggctgagg cgtgaggacc | 38820 |
| tggcttgcct tgaaaaatag ataatttccc cgcggtaggg ctgctagatc tttgctattt | 38880 |
| gaaacggcaa ccgctgtcac cgtttcgttc gtggcgaatg ttacgaccaa agtagctcca | 38940 |
| accgccgtcg agaggcgcac cacttgatcg ggattgtaag ccaaataacg catgcgcgga | 39000 |
| tctagcttgc ccgccattgg agtgtcttca gcctccgcac cagtcgcagc ggcaaataaa | 39060 |
| catgctaaaa tgaaaagtgc ttttctgatc atggttcgct gtggcctacg tttgaaacgg | 39120 |
| tatcttccga tgtctgatag gaggtgacaa ccagacctgc cgggttggtt agtctcaatc | 39180 |

```
tgccgggcaa gctggtcacc ttttcgtagc gaactgtcgc ggtccacgta ctcaccacag   39240
gcattttgcc gtcaacgacg agggtccttt tatagcgaat ttgctgcgtg cttggagtta   39300
catcatttga agcgatgtgc tcgacctcca ccctgccgcg tttgccaaga atgacttgag   39360
gcgaactggg attgggatag ttgaagaatt gctggtaatc ctggcgcact gttggggcac   39420
tgaagttcga taccaggtcg taggcgtact gagcggtgtc ggcatcataa ctctcgcgca   39480
ggcgaacgta ctcccacaat gaggcgttaa cgacggcctc ctcttgagtt gcaggcaatc   39540
gcgagacaga cacctcgctg tcaacggtgc cgtccggccg tatccataga tatacgggca   39600
caagcctgct caacggcacc attgtggcta tagcgaacgc ttgagcaaca tttcccaaaa   39660
tcgcgatagc tgcgacagct gcaatgagtt tggagagacg tcgcgccgat ttcgctcgcg   39720
cggtttgaaa ggcttctact tccttatagt gctcggcaag gctttcgcgc gccactagca   39780
tggcatattc aggccccgtc atagcgtcca cccgaattgc cgagctgaag atctgacgga   39840
gtaggctgcc atcgccccac attcagcggg aagatcgggc cttgcagct cgctaatgtg    39900 tcgtttgtct ggcagccgct caaagcgaca actaggcaca gcaggcaata cttcatagaa   39960
ttctccattg aggcgaattt ttgcgcgacc tagcctcgct caacctgagc gaagcgacgg   40020
tacaagctgc tggcagattg ggttgcgccg ctccagtaac tgcctccaat gttgccggcg   40080
atcgccggca aagcgacaat gagcgcatcc cctgtcagaa aaacatatc gagttcgtaa    40140 agaccaatga tcttggccgc ggtcgtaccg gcgaaggtga ttacaccaag cataagggtg   40200
agcgcagtcg cttcggttag gatgacgatc gttgccacga ggtttaagag gagaagcaag   40260
agaccgtagg tgataagttg cccgatccac ttagctgcga tgtcccgcgt gcgatcaaaa   40320
atatatccga cgaggatcag aggcccgatc gcgagaagca cttttcgtgag aattccaacg   40380 gcgtcgtaaa ctccgaaggc agaccagagc gtgccgtaaa ggacccactg tgcccccttgg  40440 aaagcaagga tgtcctggtc gttcatcgga ccgatttcgg atgcgatttt ctgaaaaacg   40500
gcctgggtca cggcgaacat tgtatccaac tgtgccggaa cagtctgcag aggcaagccg   40560
gttacactaa actgctgaac aaagtttggg accgtctttt cgaagatgga accacatag   40620 tcttggtagt tagcctgccc aacaattaga gcaacaacga tggtgaccgt gatcacccga   40680
gtgataccgc tacgggtatc gacttcgccg cgtatgacta aaataccctg aacaataatc   40740
caaagagtga cacaggcgat caatggcgca ctcaccgcct cctggatagt ctcaagcatc   40800
gagtccaagc ctgtcgtgaa ggctacatcg aagatcgtat gaatggccgt aaacggcgcc   40860
ggaatcgtga aattcatcga ttggacctga acttgactgg tttgtcgcat aatgttggat   40920
aaaatgagct cgcattcggc gaggatgcgg gcggatgaac aaatcgccca gccttagggg   40980
agggcaccaa agatgacagc ggtctttga tgctccttgc gttgagcggc cgcctcttcc    41040
gcctcgtgaa ggccggcctg cgcggtagtc atcgttaata ggcttgtcgc ctgtacattt   41100
tgaatcattg cgtcatggat ctgcttgaga agcaaaccat tggtcacggt tgcctgcatg   41160
atattgcgag atcgggaaag ctgagcagac gtatcagcat tcgccgtcaa gcgtttgtcc   41220 atcgttttcca gattgtcagc cgcaatgcca gcgctgtttg cggaaccggt gatctgcgat   41280
cgcaacaggt ccgcttcagc atcactaccc acgactgcac gatctgtatc gctggtgatc   41340
gcacgtgccg tggtcgacat tggcattcgc ggcgaaaaca tttcattgtc taggtccttc    41400
gtcgaaggat actgatttt ctggttgagc gaagtcagta gtccagtaac gccgtaggcc    41460
gacgtcaaca tcgtaaccat cgctatagtc tgagtgagat tctccgcagt cgcgagcgca   41520
```

```
gtcgcgagcg tctcagcctc cgttgccggg tcgctaacaa caaactgcgc ccgcgcgggc    41580
tgaatatata gaaagctgca ggtcaaaact gttgcaataa gttgcgtcgt cttcatcgtt    41640
tcctaccttg tcaatcttct gcctcgtggt gacgggccat gaattcgctg agccagccag    41700
atgagttgcc ttcttgtgcc tcgcgtagtc gagttgcaaa gcgcaccgtg ttggcacgcc    41760
ccgaaagcac ggcgacatat tcacgcatat cccgcagatc aaattcgcag atgacgcttc    41820
cactttctcg tttaagaaga aacttacggc tgccgaccgt catgtcttca cggatcgcct    41880
gaaattcctt ttcggtacat ttcagtccat cgacataagc cgatcgatct gcggttggtg    41940
atggatagaa aatcttcgtc atacattgcg caaccaagct ggctcctagc ggcgattcca    42000
gaacatgctc tggttgctgc gttgccagta ttagcatccc gttgttttt cgaacggtca    42060 ggaggaattt gtcgacgaca gtcgaaaatt tagggtttaa caaataggcg cgaaactcat    42120
cgcagctcat cacaaaacgg cggccgtcga tcatggctcc aatccgatgc aggagatatg    42180
ctgcagcggg agcgcatact tcctcgtatt cgagaagatg cgtcatgtcg aagccggtaa    42240
tcgacggatc taactttact tcgtcaactt cgccgtcaaa tgcccagcca agcgcatggc    42300
cccggcacca gcgttggagc gcgctcctg cgccttcggc gggcccatgc aacaaaaatt    42360
cacgtaaccc cgcgattgaa cgcatttgtg gatcaaacga gagctgacga tggataccac    42420
ggaccagacg gcggttctct tccggagaaa tcccacccg accatcactc tcgatgagag    42480
ccacgatcca ttcgcgcaga aaatcgtgtg aggctgctgt gttttctagg ccacgcaacg    42540
gcgccaaccc gctgggtgtg cctctgtgaa gtgccaaata tgttcctcct gtggcgcgaa    42600
ccagcaattc gccaccccgg tccttgtcaa agaacacgac cgtacctgca cggtcgacca    42660
tgctctgttc gagcatggct agaacaaaca tcatgagcgt cgtcttaccc ctcccgatag    42720
gcccgaatat tgccgtcatg ccaacatcgt gctcatgcgg gatatagtcg aaaggcgttc    42780
cgccattggt acgaaatcgg gcaatcgcgt tgccccagtg gcctgagctg gcgccctctg    42840
gaaagttttc gaaagagaca aaccctgcga aattgcgtga agtgattgcg ccagggcgtg    42900
tgcgccactt aaaattcccc ggcaattggg accaataggc cgcttccata ccaataccgtt    42960 cttggacaac cacggcacct gcatccgcca ttcgtgtccg agcccgcgcg ccctgtccc    43020 caagactatt gagatcgtct gcatagacgc aaaggctcaa atgatgtgag cccataacga    43080
attcgttgct cgcaagtgcg tcctcagcct cggataattt gccgatttga gtcacggctt    43140
tatcgccgga actcagcatc tggctcgatt tgaggctaag tttcgcgtgc gcttgcgggc    43200
gagtcaggaa cgaaaaactc tgccgtgagaa caagtggaaa atcgagggat agcagcgcgt    43260
tgagcatgcc cggccgtgtt tttgcagggt attcgcgaaa cgaatagatg gatccaacgt    43320
aactgtcttt tggcgttctg atctcgagtc ctcgcttgcc gcaaatgact ctgtcggtat    43380
aaatcgaagc gccgagtgag ccgctgacga ccggaaccgg tgtgaaccga ccagtcatga    43440
tcaaccgtag cgcttcgcca atttcggtga agagcacacc ctgcttctcg cggatgccaa    43500
gacgatgcag gccatacgct ttaagagagc cagcgacaac atgccaaaga tcttccatgt    43560
tcctgatctg gcccgtgaga tcgttttccc ttttcccgct tagcttggtg aacctcctct    43620
ttaccttccc taaagccgcc tgtgggtaga caatcaacgt aaggaagtgt tcattgcgga    43680
ggagttggcc ggagagcacg cgctgttcaa aagcttcgtt caggctagcg gcgaaaacac    43740
tacggaagtg tcgcggcgcc gatgatggca cgtcggcatg acgtacgagg tgagcatata    43800
ttgacacatg atcatcagcg atattgcgca acagcgtgtt gaacgcacga caacgcgcat    43860
tgcgcatttc agtttcctca agctcgaatg caacgccatc aattctcgca atggtcatga    43920
```

```
tcgatccgtc ttcaagaagg acgatatggt cgctgaggtg gccaatataa gggagataga   43980
tctcaccgga tctttcggtc gttccactcg cgccgagcat cacaccattc ctctccctcg   44040
tgggggaacc ctaattggat ttgggctaac agtagcgccc ccccaaactg cactatcaat   44100
gcttcttccc gcggtccgca aaaatagcag gacgacgctc gccgcattgt agtctcgctc   44160
cacgatgagc cgggctgcaa accataacgg cacgagaacg acttcgtaga gcgggttctg   44220
aacgataacg atgacaaagc cggcgaacat catgaataac cctgccaatg tcagtggcac   44280
cccaagaaac aatgcgggcc gtgtggctgc gaggtaaagg gtcgattctt ccaaacgatc   44340
agccatcaac taccgccagt gagcgtttgg ccgaggaagc tcgccccaaa catgataaca   44400
atgccgccga cgacgccggc aaccagccca agcgaagccc gcccgaacat ccaggagatc   44460
ccgatagcga caatgccgag aacagcgagt gactggccga acggaccaag gataaacgtg   44520
catatattgt taaccattgt ggcggggtca gtgccgccac ccgcagattg cgctgcggcg   44580
ggtccggatg aggaaatgct ccatgcaatt gcaccgcaca agcttggggc gcagctcgat   44640
atcacgcgca tcatcgcatt cgagagcgag aggcgattta gatgtaaacg gtatctctca   44700
aagcatcgca tcaatgcgca cctccttagt ataagtcgaa taagacttga ttgtcgtctg   44760
cggatttgcc gttgtcctgg tgtggcggtg gcggagcgat taaaccgcca gcgccatcct   44820
cctgcgagcg cgctgatat gaccccccaaa catcccacgt ctcttcggat tttagcgcct   44880
cgtgatcgtc ttttggaggc tcgattaacg cgggcaccag cgattgagca gctgtttcaa   44940
cttttcgcac gtagccgttt gcaaaaccgc cgatgaaatt accggtgttg taagcggaga   45000
tcgcccgacg aagcgcaaat tgcttctcgt caatcgtttc gccgcctgca taacgacttt   45060
tcagcatgtt tgcagcggca gataatgatg tgcacgcctg gagcgcaccg tcaggtgtca   45120
gaccgagcat agaaaaattt cgagagttta tttgcatgag gccaacatcc agcgaatgcc   45180
gtgcatcgag acggtgcctg acgacttggg ttgcttggct gtgatcttgc cagtgaagcg   45240
tttcgccggt cgtgttgtca tgaatcgcta aaggatcaaa gcgactctcc accttagcta   45300
tcgccgcaag cgtagatgtc gcaactgatg gggcacactt gcgagcaaca tggtcaaact   45360
cagcagatga gagtggcgtg gcaaggctcg acgaacagaa ggagaccatc aaggcaagag   45420
aaagcgaccc cgatctctta agcataccct atctccttag ctcgcaacta acaccgcctc   45480
tcccgttgga agaagtgcgt tgtttttatgt tgaagattat cggagggtc ggttactcga   45540
aaattttcaa ttgcttcttt atgatttcaa ttgaagcgag aaacctcgcc cggcgtcttg   45600
gaacgcaaca tggaccgaga accgcgcatc catgactaag caaccggatc gacctattca   45660
ggccgcagtt ggtcaggtca ggctcagaac gaaaatgctc ggcgaggtta cgctgtctgt   45720
aaacccattc gatgaacggg aagcttcctt ccgattgctc ttggcaggaa tattggccca   45780
tgcctgcttg cgcttttgcaa atgctcttat cgcgttggta tcatatgcct tgtccgccag   45840
cagaaacgca ctctaagcga ttatttgtaa aaatgtttcg gtcatgcggc ggtcatgggc   45900
ttgacccgct gtcagcgcaa gacggatcgg tcaaccgtcg gcatcgacaa cagcgtgaat   45960
cttggtggtc aaaccgccac gggaacgtcc catacagcca tcgtcttgat cccgctgttt   46020
cccgtcgccg catgttggtg gacgcggaca caggaactgt caatcatgac gacattctat   46080
cgaaagcctt ggaaatcaca ctcagaatat gatcccagac gtctgcctca cgccatcgta   46140
caaagcgatt gtagcaggtt gtacaggaac cgtatcgatc aggaacgtct gcccagggcg   46200
ggcccgtccg gaagcgccac aagatgacat tgatcacccg cgtcaacgcg cggcacgcga   46260
```

```
cgcggcttat ttgggaacaa aggactgaac aacagtccat tcgaaatcgg tgacatcaaa    46320
gcggggacgg gttatcagtg gcctccaagt caagcctcaa tgaatcaaaa tcagaccgat    46380
ttgcaaacct gatttatgag tgtgcggcct aaatgatgaa atcgtccttc tagatcgcct    46440
ccgtggtgta gcaacacctc gcagtatcgc cgtgctgacc ttggccaggg aattgactgg    46500
caagggtgct ttcacatgac cgctcttttg ccgcgatag atgatttcgt tgctgctttg    46560
ggcacgtaga aggagagaag tcatatcgga gaaattcctc ctggcgcgag agcctgctct    46620
atcgcgacgg catcccactg tcgggaacag accggatcat tcacgaggcg aaagtcgtca    46680
acacatgcgt tataggcatc ttcccttgaa ggatgatctt gttgctgcca atctggaggt    46740
gcggcagccg caggcagatg cgatctcagc gcaacttgcg gcaaaacatc tcactcacct    46800
gaaaaccact agcgagtctc gcgatcagac gaaggccttt tacttaacga cacaatatcc    46860
gatgtctgca tcacaggcgt cgctatccca gtcaatacta aagcggtgca ggaactaaag    46920
attactgatg acttaggcgt gccacgaggc ctgagacgac gcgcgtagac agttttttga    46980
aatcattatc aaagtgatgg cctccgctga agcctatcac ctctgcgccg gtctgtcgga    47040
gagatgggca agcattatta cggtcttcgc gcccgtacat gcattggacg attgcagggt    47100
caatggatct gagatcatcc agaggattgc cgcccttacc ttccgtttcg agttggagcc    47160
agcccctaaa tgagacgaca tagtcgactt gatgtgacaa tgccaagaga gagatttgct    47220
taacccgatt ttttgctca gcgtaagcc tattgaagct tgccggcatg acgtccgcgc     47280
cgaaagaata tcctacaagt aaaacattct gcacaccgaa atgcttggtg tagacatcga    47340
ttatgtgacc aagatcctta gcagtttcgc ttggggaccg ctccgaccag aaataccgaa    47400
gtgaactgac gccaatgaca ggaatcccct ccgtctgcag ataggtacca tcgatagatc    47460
tgctgcctcg cgcgtttcgg tgatgacggt gaaaacctct gacacatgca gctcccggag    47520
acggtcacag cttgtctgta agcggatgcc gggagcagac aagcccgtca gggcgcgtca    47580
gcgggtgttg gcgggtgtcg gggcgcagcc atgacccagt cacgtagcga tagcggagtg    47640
tatactggct taactatgcg gcatcagagc agattgtact gagagtgcac catatgcggt    47700
gtgaaatacc gcacagatgc gtaaggagaa aataccgcat caggcgctct tccgcttcct    47760
cgctcactga ctcgctgcgc tcggtcgttc ggctgcggcg agcggtatca gctcactcaa    47820
aggcggtaat acgttatcc acagaatcag gggataacgc aggaaagaac atgtgagcaa    47880
aaggccagca aaaggccagg aaccgtaaaa aggccgcgtt gctggcgttt ttccataggc    47940
tccgcccccc tgacgagcat cacaaaaatc gacgctcaag tcagaggtgg cgaaacccga    48000
caggactata aagataccag gcgtttcccc ctggaagctc cctcgtgcgc tctcctgttc    48060
cgaccctgcc gcttaccgga tacctgtccg ccttcctccc ttcgggaagc gtggcgcttt    48120
ctcatagctc acgctgtagg tatctcagtt cggtgtaggt cgttcgctcc aagctgggct    48180
gtgtgcacga accccccgtt cagcccgacc gctgcgcctt atccggtaac tatcgtcttg    48240
agtccaaccc ggtaagacac gacttatcgc cactggcagc agccactggt aacaggatta    48300
gcagagcgag gtatgtaggc ggtgctacag agttcttgaa gtggtggcct aactacggct    48360
acactagaag gacagtattt ggtatctgcg ctctgctgaa gccagttacc ttcggaaaaa    48420
gagttggtag ctcttgatcc ggcaaacaaa ccaccgctgg tagcggtggt ttttttgttt    48480
gcaagcagca gattacgcgc agaaaaaaag gatctcaaga agatcctttg atcttttcta    48540
cggggtctga cgctcagtgg aacgaaaact cacgttaagg gattttggtc atgagattat    48600
caaaaaggat cttcacctag atcctttta attaaaaatg aagttttaaa tcaatctaaa     48660
```

```
gtatatatga gtaaacttgg tctgacagtt accaatgctt aatcagtgag gcacctatct   48720
cagcgatctg tctatttcgt tcatccatag ttgcctgact ccccgtcgtg tagataacta   48780
cgatacggga gggcttacca tctggcccca gtgctgcaat gataccgcga gacccacgct   48840
caccggctcc agatttatca gcaataaacc agccagccgg aagggccgag cgcagaagtg   48900
gtcctgcaac tttatccgcc tccatccagt ctattaattg ttgccgggaa gctagagtaa   48960
gtagttcgcc agttaatagt ttgcgcaacg ttgttgccat tgctgcaggg ggggggggg    49020
gggggggactt ccattgttca ttccacggac aaaaacagag aaaggaaacg acagaggcca  49080
aaaagcctcg ctttcagcac ctgtcgtttc ctttctttc agagggtatt ttaaataaaa    49140
acattaagtt atgacgaaga agaacggaaa cgccttaaac cggaaaattt tcataaatag  49200
cgaaaacccg cgaggtcgcc gccccgtaac ctgtcggatc accggaaagg acccgtaaag  49260
tgataatgat tatcatctac atatcacaac gtgcgtggag gccatcaaac cacgtcaaat  49320
aatcaattat gacgcaggta tcgtattaat tgatctgcat caacttaacg taaaaacaac  49380
ttcagacaat acaaatcagc gacactgaat acggggcaac ctcatgtccc ccccccccc   49440
ccccctgcag gcatcgtggt gtcacgctcg tcgtttggta tggcttcatt cagctccggt  49500
tcccaacgat caaggcgagt tacatgatcc cccatgttgt gcaaaaaagc ggttagctcc  49560
ttcggtcctc cgatcgttgt cagaagtaag ttggccgcag tgttatcact catggttatg  49620
gcagcactgc ataattctct tactgtcatg ccatccgtaa gatgctttc tgtgactggt   49680
gagtactcaa ccaagtcatt ctgagaatag tgtatgcggc gaccgagttg ctcttgcccg  49740
gcgtcaacac gggataatac cgcgccacat agcagaactt taaaagtgct catcattgga  49800
aaacgttctt cggggcgaaa actctcaagg atcttaccgc tgttgagatc cagttcgatg  49860
taacccactc gtgcacccaa ctgatcttca gcatctttta ctttcaccag cgtttctggg  49920
tgagcaaaaa caggaaggca aaatgccgca aaaagggaa taaggcgac acggaaatgt    49980
tgaatactca tactcttcct ttttcaatat tattgaagca tttatcaggg ttattgtctc  50040
atgagcggat acatatttga atgtatttag aaaaataaac aaatagggt tccgcgcaca   50100
tttccccgaa aagtgccacc tgacgtctaa gaaaccatta ttatcatgac attaacctat  50160
aaaaataggc gtatcacgag gccctttcgt cttcaagaat tggtcgacga tcttgctgcg  50220
ttcggatatt ttcgtggagt tcccgccaca gacccggatt gaaggcgaga tccagcaact  50280
cgcgccagat catcctgtga cggaactttg gcgcgtgatg actggccagg acgtcggccg  50340
aaagagcgac aagcagatca cgcttttcga cagcgtcgga tttgcgatcg aggatttttc  50400
ggcgctgcgc tacgtccgcg accgcgttga gggatcaagc cacagcagcc cactcgacct  50460
tctagccgac ccgacgagc caagggatct ttttggaatg ctgctccgtc gtcaggcttt   50520
ccgacgtttg ggtggttgaa cagaagtcat tatcgtacgg aatgccaagc actcccgagg  50580
ggaaccctgt ggttggcatg cacatacaaa tggacgaacg gataaacctt ttcacgccct  50640
tttaaatatc cgttattcta ataaacgctc ttttctctta ggtttacccg ccaatatatc  50700
ctgtcaaaca ctgatagttt aaactgaagg cgggaaacga caatctgatc atgagcggag  50760
aattaaggga gtcacgttat gaccccgcc gatgacgcgg gacaagccgt tttacgtttg   50820
gaactgacag aaccgcaacg ttgaaggagc cactcagcaa gctggtacga ttgtaatacg  50880
actcactata gggcgaattg agcgctgttt aaacgctctt caactggaag agcggttact  50940
accggttaag tgactagggt c                                            50961
```

<210> SEQ ID NO 6
<211> LENGTH: 50751
<212> TYPE: DNA
<213> ORGANISM: artificial sequence
<220> FEATURE:
<223> OTHER INFORMATION: PHP34005 test vector

<400> SEQUENCE: 6

| | | | | | |
|---|---|---|---|---|---|
| acgtgaccct | agtcacttag | gttaccagag | ctggtcacct | tgtccacca | agatggaact | 60 |
| gcggccgctc | attaattaag | tcaggcgcgc | ctctagttga | agacacgttc | atgtcttcat | 120 |
| cgtaagaaga | cactcagtag | tcttcggcca | gaatggccat | ctggattcag | caggcctaga | 180 |
| aggccattta | atcctgagg | atctggtctt | cctaaggacc | cgggatatcg | ctatcaactt | 240 |
| tgtatagaaa | agttgggccg | aattcgagct | cggtacggcc | agaatggccc | ggaccgggtt | 300 |
| accgaattcg | agctcggtac | cactagtaag | cttgccgcaa | ttcgcaaaac | acacctagac | 360 |
| tagatttgtt | ttgctaaccc | aattgatatt | aattatatat | gattaatatt | tatatgtata | 420 |
| tggatttggt | taatgaaatg | catctggttc | atcaaagaat | tataaagaca | cgtgacattc | 480 |
| atttaggata | agaaatatgg | atgatctctt | tctcttttat | tcagataact | agtaattaca | 540 |
| cataacacac | aactttgatg | cccacattat | agtgattagc | atgtcactat | gtgtgcatcc | 600 |
| ttttatttca | tacattaatt | aagttggcca | atccagaaga | tggacaagtc | tggatcttca | 660 |
| ttgtttgcct | ccctgctgcg | gtttttcacc | gaagttcatg | ccagtccagc | gttttttgcag | 720 |
| cagaaaagcc | gccgacttcg | gtttgcggtc | gcgagtgaag | atccctttct | tgttaccgcc | 780 |
| aacgcgcaat | atgccttgcg | aggtcgcaaa | atcggcgaaa | ttccatacct | gttcaccgac | 840 |
| gacggcgctg | acgcgatcaa | agacgcggtg | atacatatcc | agccatgcac | actgatactc | 900 |
| ttcactccac | atgtcggtgt | acattgagtg | cagcccggct | aacgtatcca | cgccgtattc | 960 |
| ggtgatgata | atcggctgat | gcagtttctc | ctgccaggcc | agaagttctt | tttccagtac | 1020 |
| cttctctgcc | gtttccaaat | cgccgctttg | gacataccat | ccgtaataac | ggttcaggca | 1080 |
| cagcacatca | aagagatcgc | taatggtatc | ggtgtgagcg | tcgcagaaca | ttacattgac | 1140 |
| gcaggtgatc | ggacgcgtcg | ggtcgagttt | acgcgttgct | tccgccagtg | gcgcgaaata | 1200 |
| ttcccgtgca | ccttgcggac | gggtatccgg | ttcgttggca | atactccaca | tcaccacgct | 1260 |
| tgggtggttt | tgtcacgcg | ctatcagctc | tttaatcgcc | tgtaagtgcg | cttgctgagt | 1320 |
| ttccccgttg | actgcctctt | cgctgtacag | ttctttcggc | ttgttgcccg | cttcgaaacc | 1380 |
| aatccctaaa | gagaggttaa | agccgacagc | agcagtttca | tcaatcacca | cgatgccatg | 1440 |
| ttcatctgcc | cagtcgagca | tctcttcagc | gtaagggtaa | tgcgaggtac | ggtaggagtt | 1500 |
| ggccccaatc | cagtccatta | atgcgtggtc | gtgcaccatc | agcacgttat | cgaatccttt | 1560 |
| gccacgcaag | tccgcatctt | catgacgacc | aaagccagta | agtagaacg | gtttgtggtt | 1620 |
| aatcaggaac | tgttggccct | tcactgccac | tgaccggatg | ccgacgcgaa | gcgggtagat | 1680 |
| atcacactct | gtctggcttt | tggctgtgac | gcacagttca | tagagataac | cttcacccgg | 1740 |
| ttgccagagg | tgcggattca | ccacttgcaa | agtcccgcta | gtgccttgtc | cagttgcaac | 1800 |
| cacctgttga | tccgcatcac | gcagttcaac | gctgacatca | ccattggcca | ccacctgcca | 1860 |
| gtcaacagac | gcgtggttac | agtcttgcgc | gacatgcgtc | accacggtga | tatcgtccac | 1920 |
| ccaggtgttc | ggcgtggtgt | agagcattac | gctgcgatgg | attccggcat | agttaaagaa | 1980 |
| atcatgaaag | taagactgct | ttttcttgcc | gttttcgtcg | gtaatcacca | ttcccggcgg | 2040 |
| gatagtctgc | cagttcagtt | cgttgttcac | acaaacggtg | atacctgcac | atcaacaaat | 2100 |

```
tttggtcata tattagaaaa gttataaatt aaaatataca cacttataaa ctacagaaaa    2160
gcaattgcta tatactacat tcttttattt tgaaaaaaat atttgaaata ttatattact    2220
actaattaat gataattatt atatatatat caaaggtaga agcagaaact tacgtacact    2280
tttcccggca ataacatacg gcgtgacatc ggcttcaaat ggcgtatagc cgccctgatg    2340
ctccatcact tcctgattat tgacccacac tttgccgtaa tgagtgaccg catcgaaacg    2400
cagcacgata cgctggcctg cccaaccttt cggtataaag acttcgcgct gataccagac    2460
gttgcccgca taattacgaa tatctgcatc ggcgaactga tcgttaaaac tgcctggcac    2520
agcaattgcc cggcttttctt gtaacgcgct ttcccaccaa cgctgatcaa ttccacagtt    2580
ttcgcgatcc agactgaatg cccacaggcc gtcgagtttt ttgatttcac gggttggggt    2640
ttctacagga cggaccatgg tgtcgtgtgg atccaaattg tatgcaaggt gaatgacttt    2700
cttttcgtaa actagatagg agtactcctc caggatgctt aacccgtatt gacgtacaga    2760
ggtctatgat cctttttgttt ataaaggagc ttgtagttca gtcagtctta tacttcacga    2820
tgcccatgtt tctatatagg atattatctt ggctttgtaa gtacttcacg caggttatgt    2880
tctgtttcta ggatattatc ctcatacatg cgaagaacca attttccccc cattctcttc    2940
gggtactttt tcttgggtag gcatgctctc ttggaccaac tagcataaaa cataatcatt    3000
tttccctaca gccttgacca gctataatcg aaatcatgct cattttctta agaaagactg    3060
aatacagctc caatttaaac aatttaaatc ataaacttgt aactcaatta gagaaaagca    3120
gagcccttcg gctcctatct aaaggaatta ccccatgaaa gccataaaaa cgaaccttgc    3180
tctgatacca gacgggtcta cgctcgcgga actaggatct tgcgctctac tcgcacaaag    3240
tgaactcgca caaagtgtgt tcaagcaca gaagttttta tttctcaaat caggagtaaa    3300
ctcgcgttgt ggtgcgtgtt tgcaacctga atacaaggct ccttatatag agagttgtgg    3360
agctttctgg catcgttagg tggcatccac caataatgca gataagcatc atcacatgtc    3420
tctggcctaa caactttgcg taagaatcct gcaaagttac taaaggtcat cgtgcgtgac    3480
tagacaacgc acaccgacaa acttaaaata aagagacatt atactttgtc tcctctttac    3540
ataaagtgag tggtatccag ctcactccgc atcttatcag tcttcacacc ggttggtatc    3600
aacacgtggt aggggtccgc cacttccgct tcagtcatca ttactgatat ccagcagatc    3660
tagagcatct tcaataagat attcttgttc tgcacgcaga ttttcttgct ccctcagtaa    3720
ttcctcccac agtgagtctt ctgatatttc ttcaagtttc ttctcccatc tgatcttttc    3780
ctgcacaaac gagtcaattt ggtctttcca gacccaagta aaacaagtgt tagtttcaca    3840
ggagtaaaac tccctgtcag gatttctgga tgttctggag atcttcagtt ttgctggttt    3900
attgcatcca catttgaaaa ccggctcttc acttagtgtt agcacattga tttgatgcaa    3960
cctgtagcct ttgctcaacc agtcttcata tcttttttaca acatcattaa ctctctgttt    4020
tgcatcggtg tttcccttgt gaaataccctc ctccactgca ttgatcaaca caccttcaga    4080
ttgatgcttt tccggatgga gaataatctt taccagtctt gacagagtgt ctgctaaaac    4140
gttgtccttt ccgtcaatgt gttcaaactt aatctcaaga cctgtcccgg taatgtaatc    4200
tgtgaaggca agccatctga ctcttgatgg tttatgatca ctgcttttct tgtaaaagct    4260
cactattgct tgactgtcag ttctgattat gagctctttg taagcttggt cacccggtcc    4320
gggcctagaa ggccagcttc ggccgccccg ggcaacttta ttatacaaag ttgatagata    4380
tcggaccgat taaactttaa ttcggtccga agcttgcatg cctgcagtgc agcgtgaccc    4440
```

```
ggtcgtgccc ctctctagag ataatgagca ttgcatgtct aagttataaa aaattaccac    4500 atatttttt tgtcacactt gtttgaagtg cagtttatct atctttatac atatatttaa     4560
actttactct acgaataata taatctatag tactacaata atatcagtgt tttagagaat    4620
catataaatg aacagttaga catggtctaa aggacaattg agtattttga caacaggact    4680
ctacagtttt atcttttag tgtgcatgtg ttctcctttt tttttgcaaa tagcttcacc     4740
tatataatac ttcatccatt ttattagtac atccatttag gtttagggt taatggtttt     4800 tatagactaa ttttttagt acatctattt tattctattt tagcctctaa attaagaaaa     4860
ctaaaactct attttagttt ttttatttaa taatttagat ataaaataga ataaataaaa    4920
gtgactaaaa attaaacaaa taccctttaa gaaattaaaa aaactaagga aacattttc     4980 ttgtttcgag tagataatgc cagcctgtta aacgccgtcg acgagtctaa cggacaccaa    5040
ccagcgaacc agcagcgtcg cgtcgggcca agcgaagcag acggcacggc atctctgtcg    5100
ctgcctctgg accctctcg agagttccgc tccaccgttg gacttgctcc gctgtcggca    5160
tccagaaatt gcgtggcgga gcggcagacg tgagccggca cggcaggcgg cctcctcctc    5220
ctctcacggc accggcagct acggggggatt cctttcccac cgctccttcg ctttcccttc    5280
ctcgcccgcc gtaataaata gacccccct ccacaccctc tttccccaac ctcgtgttgt     5340
tcggagcgca cacacacaca accagatctc ccccaaatcc acccgtcggc acctccgctt    5400
caaggtacgc cgctcgtcct cccccccccc cctctctacc ttctctagat cggcgttccg    5460
gtccatgcat ggttagggcc cggtagttct acttctgttc atgtttgtgt tagatccgtg    5520
tttgtgttag atccgtgctg ctagcgttcg tacacggatg cgacctgtac gtcagacacg    5580
ttctgattgc taacttgcca gtgtttctct ttggggaatc ctgggatggc tctagccgtt    5640
ccgcagacgg gatcgatttc atgatttttt ttgtttcgtt gcatagggtt tggtttgccc    5700
ttttccttta tttcaatata tgccgtgcac ttgtttgtcg ggtcatcttt tcatgctttt    5760
ttttgtcttg gttgtgatga tgtggtctgg ttgggcggtc gttctagatc ggagtagaat    5820
tctgtttcaa actacctggt ggatttatta attttggatc tgtatgtgtg tgccatacat    5880
attcatagtt acgaattgaa gatgatggat ggaaatatcg atctaggata ggtatacatg    5940
ttgatgcggg ttttactgat gcatatacag agatgctttt tgttcgcttg gttgtgatga    6000
tgtggtgtgg ttgggcggtc gttcattcgt tctagatcgg agtagaatac tgtttcaaac    6060
tacctggtgt atttattaat tttggaactg tatgtgtgtg tcatacatct tcatagttac    6120
gagtttaaga tggatggaaa tatcgatcta ggataggtat acatgttgat gtgggtttta    6180
ctgatgcata tacatgatgg catatgcagc atctattcat atgctctaac cttgagtacc    6240
tatctattat aataaacaag tatgttttat aattatttg atcttgatat acttggatga    6300
tggcatatgc agcagctata tgtggatttt tttagccctg ccttcatacg ctatttattt    6360
gcttggtact gtttcttttg tcgatgctca ccctgttgtt tggtgttact tctgcaggtc    6420
gactttaact tagcctagga tccacacgac accatgtccc ccgagcgccg ccccgtcgag    6480
atccgcccgg ccaccgccgc cgacatggcc gccgtgtgcg acatcgtgaa ccactacatc    6540
gagacctcca ccgtgaactt ccgcaccgag ccgcagaccc gcaggagtg gatcgacgac    6600 ctggagcgcc tccaggaccg ctacccgtgg ctcgtggccg aggtggaggg cgtggtggcc    6660
ggcatcgcct acgccggccc gtggaaggcc cgcaacgcct acgactggac cgtggagtcc    6720
accgtgtacg tgtcccaccg ccaccagcgc ctcggcctcg gctccaccct ctacacccac    6780
ctcctcaaga gcatggaggc ccagggcttc aagtccgtgg tggccgtgat cggcctcccg    6840
```

```
aacgacccgt ccgtgcgcct ccacgaggcc ctcggctaca ccgcccgcgg caccctccgc   6900
gccgccggct acaagcacgg cggctggcac gacgtcggct tctggcagcg cgacttcgag   6960
ctgccggccc cgccgcgccc ggtgcgcccg gtgacgcaga tctgagtcga aacctagact   7020
tgtccatctt ctggattggc caacttaatt aatgtatgaa ataaaaggat gcacacatag   7080
tgacatgcta atcactataa tgtgggcatc aaagttgtgt gttatgtgta attactagtt   7140
atctgaataa aagagaaaga gatcatccat atttcttatc ctaaatgaat gtcacgtgtc   7200
tttataattc tttgatgaac cagatgcatt tcattaacca aatccatata catataaata   7260
ttaatcatat ataattaata tcaattgggt tagcaaaaca aatctagtct aggtgtgttt   7320
tgcgaatgcg gccgataagt gactagggtc acgtgaccct agtcacttag gtaccgagct   7380
cgaattcatt ccgattaatc gtggcctctt gctcttcagg atgaagagct atgtttaaac   7440
gtgcaagcgc tactagacaa ttcagtacat aaaaacgtc cgcaatgtgt tattaagttg   7500
tctaagcgtc aatttgttta caccacaata tatcctgcca ccagccagcc aacagctccc   7560
cgaccggcag ctcggcacaa aatcaccact cgatacaggc agcccatcag tccgggacgg   7620
cgtcagcggg agagccgttg taaggcggca gactttgctc atgttaccga tgctattcgg   7680
aagaacggca actaagctgc cgggtttgaa acacggatga tctcgcggag ggtagcatgt   7740
tgattgtaac gatgacagag cgttgctgcc tgtgatcaaa tatcatctcc ctcgcagaga   7800
tccgaattat cagccttctt attcatttct cgcttaaccg tgacaggctg tcgatcttga   7860
gaactatgcc gacataatag gaaatcgctg gataaagccg ctgaggaagc tgagtggcgc   7920
tatttcttta gaagtgaacg ttgacgatcg tcgaccgtac cccgatgaat taattcggac   7980
gtacgttctg aacacagctg gatacttact tgggcgattg tcatacatga catcaacaat   8040
gtacccgttt gtgtaaccgt ctcttggagg ttcgtatgac actagtggtt cccctcagct   8100
tgcgactaga tgttgaggcc taacattta ttagagagca ggctagttgc ttagatacat    8160
gatcttcagg ccgttatctg tcagggcaag cgaaaattgg ccatttatga cgaccaatgc   8220
cccgcagaag ctcccatctt tgccgccata gacgccgcgc cccccttttg gggtgtagaa   8280 catcctttg ccagatgtgg aaaagaagtt cgttgtccca ttgttggcaa tgacgtagta    8340
gccggcgaaa gtgcgagacc catttgcgct atatataagc ctacgatttc cgttgcgact   8400
attgtcgtaa ttggatgaac tattatcgta gttgctctca gagttgtcgt aatttgatgg   8460
actattgtcg taattgctta tggagttgtc gtagttgctt ggagaaatgt cgtagttgga   8520
tggggagtag tcatagggaa gacgagcttc atccactaaa acaattggca ggtcagcaag   8580
tgcctgcccc gatgccatcg caagtacgag gcttagaacc accttcaaca gatcgcgcat   8640
agtcttcccc agctctctaa cgcttgagtt aagccgcgcc gcgaagcggc gtcggcttga   8700
acgaattgtt agacattatt tgccgactac cttggtgatc tcgcctttca cgtagtgaac   8760
aaattcttcc aactgatctg cgcgcgaggc caagcgatct tcttgtccaa gataagcctg   8820
cctagcttca agtatgacgg gctgatactg gccggcagg cgctccattg cccagtcggc    8880
agcgacatcc ttcggcgcga ttttgccggt tactgcgctg taccaaatgc gggacaacgt   8940
aagcactaca tttcgctcat cgccagccca gtcgggcggc gagttccata gcgttaaggt   9000
ttcatttagc gcctcaaata gatcctgttc aggaaccgga tcaaagagtt cctccgccgc   9060
tggacctacc aaggcaacgc tatgttctct tgcttttgtc agcaagatag ccagatcaat   9120
gtcgatcgtg gctggctcga agatacctgc aagaatgtca ttgcgctgcc attctccaaa   9180
```

```
ttgcagttcg cgcttagctg gataacgcca cggaatgatg tcgtcgtgca caacaatggt    9240
gacttctaca gcgcggagaa tctcgctctc tccaggggaa gccgaagttt ccaaaaggtc    9300
gttgatcaaa gctcgccgcg ttgtttcatc aagccttaca gtcaccgtaa ccagcaaatc    9360
aatatcactg tgtggcttca ggccgccatc cactgcggag ccgtacaaat gtacggccag    9420
caacgtcggt tcgagatggc gctcgatgac gccaactacc tctgatagtt gagtcgatac    9480
ttcggcgatc accgcttccc tcatgatgtt taactcctga attaagccgc ccgcgaagc    9540
ggtgtcggct tgaatgaatt gttaggcgtc atcctgtgct cccgagaacc agtaccagta    9600
catcgctgtt tcgttcgaga cttgaggtct agttttatac gtgaacaggt caatgccgcc    9660
gagagtaaag ccacattttg cgtacaaatt gcaggcaggt acattgttcg tttgtgtctc    9720
taatcgtatg ccaaggagct gtctgcttag tgcccacttt ttcgcaaatt cgatgagact    9780
gtgcgcgact cctttgcctc ggtgcgtgtg cgacacaaca atgtgttcga tagaggctag    9840
atcgttccat gttgagttga gttcaatctt cccgacaagc tcttggtcga tgaatgcgcc    9900
atagcaagca gagtcttcat cagagtcatc atccgagatg taatccttcc ggtagggcgt    9960
cacacttctg gtagatagtt caaagccttg gtcggatagg tgcacatcga acacttcacg   10020
aacaatgaaa tggttctcag catccaatgt ttccgccacc tgctcaggga tcaccgaaat   10080
cttcatatga cgcctaacgc ctggcacagc ggatcgcaaa cctggcgcgg cttttggcac   10140
aaaaggcgtg acaggtttgc gaatccgttg ctgccacttg ttaacccttt tgccagattt   10200
ggtaactata atttatgtta gaggcgaagt cttgggtaaa aactggccta aaattgctgg   10260
ggatttcagg aaagtaaaca tcaccttccg gctcgatgtc tattgtagat atatgtagtg   10320
tatctacttg atcggggat ctgctgcctc gcgcgtttcg gtgatgacgg tgaaaacctc   10380
tgacacatgc agctcccgga gacggtcaca gcttgtctgt aagcggatgc cgggagcaga   10440
caagcccgtc agggcgcgtc agcgggtgtt ggcgggtgtc ggggcgcagc catgacccag   10500
tcacgtagcg atagcggagt gtatactggc ttaactatgc ggcatcagag cagattgtac   10560
tgagagtgca ccatatgcgg tgtgaaatac cgcacagatg cgtaaggaga aataccgca   10620
tcaggcgctc ttccgcttcc tcgctcactg actcgctgcg ctcggtcgtt cggctgcggc   10680
gagcggtatc agctcactca aaggcggtaa tacggttatc cacagaatca ggggataacg   10740
caggaaagaa catgtgagca aaaggccagc aaaaggccag gaaccgtaaa aaggccgcgt   10800
tgctggcgtt tttccatagg ctccgccccc ctgacgagca tcacaaaaat cgacgctcaa   10860
gtcagaggtg gcgaaacccg acaggactat aaagatacca ggcgtttccc cctggaagct   10920
ccctcgtgcg ctctcctgtt ccgaccctgc cgcttaccgg atacctgtcc gcctttctcc   10980
cttcgggaag cgtggcgctt tctcatagct cacgctgtag gtatctcagt tcggtgtagg   11040
tcgttcgctc caagctgggc tgtgtgcacg aaccccccgt tcagcccgac cgctgcgcct   11100
tatccggtaa ctatcgtctt gagtccaacc cggtaagaca cgacttatcg ccactggcag   11160
cagccactgg taacaggatt agcagagcga ggtatgtagg cggtgctaca gagttcttga   11220
agtggtggcc taactacggc tacactagaa ggacagtatt tggtatctgc gctctgctga   11280
agccagttac cttcggaaaa agagttggta gctcttgatc cggcaaacaa accaccgctg   11340
gtagcggtgg tttttttgtt tgcaagcagc agattacgcg cagaaaaaaa ggatctcaag   11400
aagatccttt gatcttttct acggggtctg acgctcagtg gaacgaaaac tcacgttaag   11460
ggattttggt catgagatta tcaaaaagga tcttcaccta gatcctttta aattaaaaat   11520
gaagttttaa atcaatctaa agtatatatg agtaaacttg gtctgacagt taccaatgct   11580
```

```
taatcagtga ggcacctatc tcagcgatct gtctatttcg ttcatccata gttgcctgac    11640
tccccgtcgt gtagataact acgatacggg agggcttacc atctggcccc agtgctgcaa    11700
tgataccgcg agacccacgc tcaccggctc cagatttatc agcaataaac cagccagccg    11760
gaagggccga gcgcagaagt ggtcctgcaa ctttatccgc ctccatccag tctattaatt    11820
gttgccggga agctagagta agtagttcgc cagttaatag tttgcgcaac gttgttgcca    11880
ttgctgcagg ggggggggggg gggggttcc attgttcatt ccacggacaa aaacagaaa    11940 aggaaacgac agaggccaaa aagctcgctt tcagcacctg tcgtttcctt tcttttcaga    12000
gggtatttta ataaaaaaca ttaagttatg acgaagaaga acggaaacgc cttaaaccgg    12060
aaaattttca taaatagcga aaacccgcga ggtcgccgcc ccgtaacctg tcggatcacc    12120
ggaaaggacc cgtaaagtga taatgattat catctacata tcacaacgtg cgtggaggcc    12180
atcaaaccac gtcaaataat caattatgac gcaggtatcg tattaattga tctgcatcaa    12240
cttaacgtaa aaacaacttc agacaataca aatcagcgac actgaatacg ggcaacctc     12300 atgtccccccc cccccccccc cctgcaggca tcgtggtgtc acgctcgtcg tttggtatgg    12360
cttcattcag ctccggttcc caacgatcaa ggcgagttac atgatccccc atgttgtgca    12420
aaaaagcggt tagctccttc ggtcctccga tcgttgtcag aagtaagttg gccgcagtgt    12480
tatcactcat ggttatggca gcactgcata attctcttac tgtcatgcca tccgtaagat    12540
gcttttctgt gactggtgag tactcaacca agtcattctg agaatagtgt atgcggcgac    12600
cgagttgctc ttgcccggcg tcaacacggg ataataccgc gccacatagc agaactttaa    12660
aagtgctcat cattggaaaa cgttcttcgg ggcgaaaact ctcaaggatc ttaccgctgt    12720
tgagatccag ttcgatgtaa cccactcgtg cacccaactg atcttcagca tcttttactt    12780
tcaccagcgt ttctgggtga gcaaaaacag gaaggcaaaa tgccgcaaaa aagggaataa    12840
gggcgacacg gaaatgttga atactcatac tcttcctttt tcaatattat tgaagcattt    12900
atcagggtta ttgtctcatg agcggataca tatttgaatg tatttagaaa aataaacaaa    12960 tagggggttcc gcgcacattt ccccgaaaag tgccacctga cgtctaagaa accattatta    13020
tcatgacatt aacctataaa aataggcgta tcacgaggcc ctttcgtctt caagaattcg    13080
gagcttttgc cattctcacc ggattcagtc gtcactcatg gtgatttctc acttgataac    13140
cttatttttg acgaggggaa attaataggt tgtattgatg ttggacgagt cggaatcgca    13200
gaccgatacc aggatcttgc catcctatgg aactgcctcg gtgagttttc tccttcatta    13260
cagaaacggc ttttttcaaaa atatggtatt gataatcctg atatgaataa attgcagttt    13320
catttgatgc tcgatgagtt tttctaatca gaattggtta attggttgta acactggcag    13380
agcattacgc tgacttgacg ggacggcggc tttgttgaat aaatcgaact tttgctgagt    13440
tgaaggatca gatcacgcat cttcccgaca acgcagaccg ttccgtggca aagcaaaagt    13500
tcaaaatcac caactggtcc acctacaaca aagctctcat caaccgtggc tccctcactt    13560
tctggctgga tgatggggcg attcaggcct ggtatgagtc agcaacacct tcttcacgag    13620
gcagacctca gcgccagaag gccgccagag aggccgagcg cggccgtgag gcttggacgc    13680
tagggcaggg catgaaaaag cccgtagcgg gctgctacgg gcgtctgacg cggtggaaag    13740
ggggagggga tgttgtctac atggctctgc tgtagtgagt gggttgcgct ccggcagcgg    13800
tcctgatcaa tcgtcaccct ttctcggtcc ttcaacgttc ctgacaacga gcctcctttt    13860
cgccaatcca tcgacaatca ccgcgagtcc ctgctcgaac gctgcgtccg gaccggcttc    13920
```

```
gtcgaaggcg tctatcgcgg cccgcaacag cggcgagagc ggagcctgtt caacggtgcc    13980
gccgcgctcg ccggcatcgc tgtcgccggc ctgctcctca agcacggccc caacagtgaa    14040
gtagctgatt gtcatcagcg cattgacggc gtccccggcc gaaaaacccg cctcgcagag    14100
gaagcgaagc tgcgcgtcgg ccgtttccat ctgcggtgcg cccggtcgcg tgccggcatg    14160
gatgcgcgcg ccatcgcggt aggcgagcag cgcctgcctg aagctgcggg cattcccgat    14220
cagaaatgag cgccagtcgt cgtcggctct cggcaccgaa tgcgtatgat tctccgccag    14280
catggcttcg gccagtgcgt cgagcagcgc ccgcttgttc ctgaagtgcc agtaaagcgc    14340
cggctgctga accccaacc gttccgccag tttgcgtgtc gtcagaccgt ctacgccgac    14400
ctcgttcaac aggtccaggg cggcacggat cactgtattc ggctgcaact tgtcatgct    14460 tgacactta tcactgataa acataatatg tccaccaact tatcagtgat aaagaatccg    14520
cgcgttcaat cggaccagcg gaggctggtc cggaggccag acgtgaaacc caacataccc    14580
ctgatcgtaa ttctgagcac tgtcgcgctc gacgctgtcg gcatcggcct gattatgccg    14640
gtgctgccgg gcctcctgcg cgatctggtt cactcgaacg acgtcaccgc ccactatggc    14700
attctgctgg cgctgtatgc gttggtgcaa tttgcctgcg cacctgtgct gggcgcgctg    14760
tcggatcgtt tcgggcggcg gccaatcttg ctcgtctcgc tggccggcgc cactgtcgac    14820
tacgccatca tggcgacagc gccttttcctt tgggttctct atatcgggcg gatcgtggcc    14880
ggcatcaccg gggcgactgg ggcggtagcc ggcgcttata ttgccgatat cactgatggc    14940
gatgagcgcg cgcggcactt cggcttcatg agcgcctgtt tcgggttcgg gatggtcgcg    15000
ggacctgtgc tcgtgtgggct gatgggcggt ttctcccccc acgctccgtt cttcgccgcg    15060
gcagccttga acggcctcaa tttcctgacg ggctgttttcc ttttgccgga gtcgcacaaa    15120
ggcgaacgcc ggccgttacg ccgggaggct ctcaacccgc tcgcttcgtt ccggtgggcc    15180
cggggcatga ccgtcgtcgc cgccctgatg gcggtcttct tcatcatgca acttgtcgga    15240
caggtgccgg ccgcgctttg ggtcatttc ggcgaggatc gctttcactg ggacgcgacc    15300
acgatcggca tttcgcttgc cgcatttggc attctgcatt cactcgccca ggcaatgatc    15360 accgccctg tagccgcccg gctcggcgaa aggcgggcac tcatgctcgg aatgattgcc    15420
gacggcacag gctacatcct gcttgccttc gcgacacggg gatggatggc gttcccgatc    15480
atggtcctgc ttgcttcggg tggcatcgga atgccggcgc tgcaagcaat gttgtccagg    15540
caggtggatg aggaacgtca ggggcagctg caaggctcac tggcggcgct caccagcctg    15600
acctcgatcg tcggaccccct cctcttcacg gcgatctatg cggcttctat aacaacgtgg    15660
aacgggtggg catggattgc aggcgctgcc ctctacttgc tctgcctgcc ggcgctgcgt    15720
cgcgggcttt ggagcggcgc agggcaacga gccgatcgct gatcgtggaa acgataggcc    15780
tatgccatgc gggtcaaggc gacttccggc aagctatacg cgccctagga gtgcggttgg    15840
aacgttggcc cagccagata ctcccgatca cgagcaggac gccgatgatt tgaagcgcac    15900
tcagcgtctg atccaagaac aaccatccta gcaacacggc ggtccccggg ctgagaaagc    15960
ccagtaagga aacaactgta ggttcgagtc gcgagatccc ccggaaccaa aggaagtagg    16020
ttaaacccgc tccgatcagg ccgagccacg ccaggccgag aacattggtt cctgtaggca    16080
tcgggattgg cggatcaaac actaaagcta ctggaacgag cagaagtcct ccggccgcca    16140
gttgccaggc ggtaaaggtg agcagaggca cgggaggttg ccacttgcgg gtcagcacgg    16200
ttccgaacgc catggaaacc gccccgccga ggcccgctgc gacgccgaca ggatctagcg    16260 ctgcgttgg tgtcaacacc aacagcgcca cgcccgcagt tccgcaaata gcccccagga    16320
```

```
ccgccatcaa tcgtatcggg ctacctagca gagcggcaga gatgaacacg accatcagcg   16380
gctgcacagc gcctaccgtc gccgcgaccc cgcccggcag gcggtagacc gaaataaaca   16440
acaagctcca gaatagcgaa atattaagtg cgccgaggat gaagatgcgc atccaccaga   16500
ttcccgttgg aatctgtcgg acgatcatca cgagcaataa acccgccggc aacgcccgca   16560
gcagcatacc ggcgacccct cggcctcgct gttcgggctc cacgaaaacg ccggacagat   16620
gcgccttgtg agcgtccttg gggccgtcct cctgtttgaa gaccgacagc ccaatgatct   16680
cgccgtcgat gtaggcgccg aatgccacgg catctcgcaa ccgttcagcg aacgcctcca   16740
tgggcttttt ctcctcgtgc tcgtaaacgg acccgaacat ctctggagct ttcttcaggg   16800
ccgacaatcg gatctcgcgg aaatcctgca cgtcggccgc tccaagccgt cgaatctgag   16860
ccttaatcac aattgtcaat tttaatcctc tgtttatcgg cagttcgtag agcgcgccgt   16920
gcgtcccgag cgatactgag cgaagcaagt gcgtcgagca gtgcccgctt gttcctgaaa   16980
tgccagtaaa gcgctggctg ctgaaccccc agcggaact gaccccacaa ggccctagcg   17040
tttgcaatgc accaggtcat cattgaccca ggcgtgttcc accaggccgc tgcctcgcaa   17100
ctcttcgcag gcttcgccga cctgctcgcg ccacttcttc acgcgggtgg aatccgatcc   17160
gcacatgagg cggaaggttt ccagcttgag cgggtacggc tcccggtgcg agctgaaata   17220
gtcgaacatc cgtcgggccg tcggcgacag cttgcggtac ttctcccata tgaatttcgt   17280
gtagtggtcg ccagcaaaca gcacgacgat ttcctcgtcg atcaggacct ggcaacggga   17340
cgttttcttg ccacggtcca ggacgcggaa gcggtgcagc agcgacaccg attccaggtg   17400
cccaacgcgg tcggacgtga agcccatcgc cgtcgcctgt aggcgcgaca ggcattcctc   17460
ggccttcgtg taataccggc cattgatcga ccagcccagg tcctggcaaa gctcgtagaa   17520
cgtgaaggtg atcggctcgc cgatagggt gcgcttcgcg tactccaaca cctgctgcca   17580
caccagttcg tcatcgtcgg cccgcagctc gacgccggtg taggtgatct tcacgtcctt   17640
gttgacgtgg aaaatgacct tgttttgcag cgcctcgcgc gggattttct tgttgcgcgt   17700
ggtgaacagg gcagagcggg ccgtgtcgtt tggcatcgct cgcatcgtgt ccggccacgg   17760
cgcaatatcg aacaaggaaa gctgcatttc cttgatctgc tgcttcgtgt gtttcagcaa   17820
cgcggcctgc ttggcctcgc tgacctgttt tgccaggtcc tcgccggcgg ttttcgctt    17880 cttggtcgtc atagttcctc gcgtgtcgat ggtcatcgac ttcgccaaac ctgccgcctc   17940
ctgttcgaga cgacgcgaac gctccacggc ggccgatggc gcgggcaggg caggggagc    18000 cagttgcacg ctgtcgcgct cgatcttggc cgtagcttgc tggaccatcg agccgacgga   18060
ctggaaggtt tcgcggggcg cacgcatgac ggtgcggctt gcgatggttt cggcatcctc   18120
ggcggaaaac cccgcgtcga tcagttcttg cctgtatgcc ttccggtcaa acgtccgatt   18180
cattcaccct ccttgcggga ttgccccgac tcacgccggg gcaatgtgcc cttattcctg   18240
atttgacccg cctggtgcct tggtgtccag ataatccacc ttatcggcaa tgaagtcggt   18300
cccgtagacc gtctggccgt ccttctcgta cttggtattc cgaatcttgc cctgcacgaa   18360
taccagcgac cccttgccca aatacttgcc gtgggcctcg gcctgagagc caaaacactt   18420
gatgcggaag aagtcggtgc gctcctgctt gtcgccggca tcgttgcgcc actcttcatt   18480
aaccgctata tcgaaaattg cttgcggctt gttagaattg ccatgacgta cctcggtgtc   18540
acgggtaaga ttaccgataa actgaactg attatggctc atatcgaaag tctccttgag   18600
aaaggagact ctagtttagc taaacattgg ttccgctgtc aagaacttta gcggctaaaa   18660
```

```
ttttgcgggc cgcgaccaaa ggtgcgaggg gcggcttccg ctgtgtacaa ccagatattt    18720
ttcaccaaca tccttcgtct gctcgatgag cggggcatga cgaaacatga gctgtcggag    18780
agggcagggg tttcaatttc gttttatca gacttaacca acggtaaggc caacccctcg     18840
ttgaaggtga tggaggccat tgccgacgcc ctggaaactc ccctacctct tctcctggag    18900
tccaccgacc ttgaccgcga ggcactcgcg gagattgcgg gtcatccttt caagagcagc    18960
gtgccgcccg gatacgaacg catcagtgtg gttttgccgt cacataaggc gtttatcgta    19020
aagaaatggg gcgacgacac ccgaaaaaag ctgcgtggaa ggctctgacg ccaagggtta    19080
gggcttgcac ttccttcttt agccgctaaa acggccccctt ctctgcgggc cgtcggctcg   19140
cgcatcatat cgacatcctc aacggaagcc gtgccgcgaa tggcatcggg cgggtgcgct    19200
ttgacagttg ttttctatca gaaccgctac gtcgtgcggt tcgattagct gtttgtcttg    19260
caggctaaac actttcggta tatcgtttgc ctgtgcgata atgttgctaa tgatttgttg    19320
cgtaggggtt actgaaaagt gagcgggaaa gaagagtttc agaccatcaa ggagcgggcc    19380
aagcgcaagc tggaacgcga catgggtgcg gacctgttgg ccgcgctcaa cgacccgaaa    19440
accgttgaag tcatgctcaa cgcggacggc aaggtgtggc acgaacgcct tggcgagccg    19500
atgcggtaca tctgcgacat gcggcccagc cagtcgcagg cgattataga aacggtggcc    19560
ggattccacg gcaaagaggt cacgcggcat tcgcccatcc tggaaggcga gttccccttg    19620
gatggcagcc gctttgccgg ccaattgccg ccggtcgtgg ccgcgccaac ctttgcgatc    19680
cgcaagcgcg cggtcgccat cttcacgctg gaacagtacg tcgaggcggg catcatgacc    19740
cgcgagcaat acgaggtcat taaaagcgcc gtcgcggcgc atcgaaacat cctcgtcatt    19800
ggcggtactg gctcgggcaa gaccacgctc gtcaacgcga tcatcaatga aatggtcgcc    19860
ttcaacccgt ctgagcgcgt cgtcatcatc gaggacaccg gcgaaatcca gtgcgccgca    19920
gagaacgccg tccaataccca caccagcatc gacgtctcga tgacgctgct gctcaagaca   19980
acgctgcgta tgcgccccga ccgcatcctg gtcggtgagg tacgtggccc cgaagccctt    20040
gatctgttga tggcctggaa caccgggcat gaaggaggtg ccgccaccct gcacgcaaac    20100
aaccccaaag cgggcctgag ccggctcgcc atgcttatca gcatgcaccc ggattcaccg    20160
aaacccattg agccgctgat tggcgaggcg gttcatgtgg tcgtccatat cgccaggacc    20220
cctagcggcc gtcgagtgca agaaattctc gaagttcttg gttacgagaa cggccagtac    20280
atcaccaaaa ccctgtaagg agtatttcca atgacaacgg ctgttccgtt ccgtctgacc    20340
atgaatcgcg gcattttgtt ctaccttgcc gtgttcttcg ttctcgctct cgcgttatcc    20400
gcgcatccgg cgatggcctc ggaaggcacc ggcggcagct tgccatatga gagctggctg    20460
acgaacctgc gcaactccgt aaccggcccg gtggccttcg cgctgtccat catcggcatc    20520
gtcgtcgccg gcggcgtgct gatcttcggc ggcgaactca acgccttctt ccgaaccctg    20580
atcttcctgg ttctggtgat ggcgctgctg gtcggcgcgc agaacgtgat gagcaccttc    20640
ttcggtcgtg gtgccgaaat cgcggccctc ggcaacgggg cgctgcacca ggtgcaagtc    20700
gcggcggcgg atgccgtgcg tgcggtagcg gctggacggc tcgcctaatc atggctctgc    20760
gcacgatccc catccgtcgc gcaggcaacc gagaaaacct gttcatgggt ggtgatcgtg    20820
aactggtgat gttctcgggc ctgatggcgt ttgcgctgat tttcagcgcc caagagctgc    20880
gggccaccgt ggtcggtctg atcctgtggt tcggggcgct ctatgcgttc cgaatcatgg    20940
cgaaggccga tccgaagatg cggttcgtgt acctgcgtca ccgccggtac aagccgtatt    21000
acccggcccg ctcgaccccg ttccgcgaga acaccaatag ccaagggaag caataccgat    21060
```

```
gatccaagca attgcgattg caatcgcggg cctcggcgcg cttctgttgt tcatcctctt   21120
tgcccgcatc cgcgcggtcg atgccgaact gaaactgaaa aagcatcgtt ccaaggacgc   21180
cggcctggcc gatctgctca actacgccgc tgtcgtcgat gacggcgtaa tcgtgggcaa   21240
gaacggcagc tttatggctg cctggctgta caagggcgat gacaacgcaa gcagcaccga   21300
ccagcagcgc gaagtagtgt ccgcccgcat caaccaggcc ctcgcgggcc tgggaagtgg   21360
gtggatgatc catgtggacg ccgtgcggcg tcctgctccg aactacgcgg agcggggcct   21420
gtcggcgttc cctgaccgtc tgacggcagc gattgaagaa gagcgctcgg tcttgccttg   21480
ctcgtcggtg atgtacttca ccagctccgc gaagtcgctc ttcttgatgg agcgcatggg   21540
gacgtgcttg gcaatcacgc gcacccccg gccgttttag cggctaaaaa agtcatggct   21600
ctgccctcgg gcgaccacg cccatcatga ccttgccaag ctcgtcctgc ttctcttcga   21660
tcttcgccag cagggcgagg atcgtggcat caccgaaccg cgccgtgcgc gggtcgtcgg   21720
tgagccagag tttcagcagg ccgcccaggc ggcccaggtc gccattgatg cgggccagct   21780
cgcggacgtg ctcatagtcc acgacgcccg tgattttgta gccctggccg acggccagca   21840
ggtaggccga caggctcatg ccggccgccg ccgcctttc ctcaatcgct cttcgttcgt   21900
ctggaaggca gtacaccttg ataggtgggc tgcccttcct ggttggcttg gtttcatcag   21960
ccatccgctt gccctcatct gttacgccgg cggtagccgg ccagcctcgc agagcaggat   22020
tcccgttgag caccgccagg tgcgaataag ggacagtgaa gaaggaacac ccgctcgcgg   22080
gtgggcctac ttcacctatc ctgcccggct gacgccgttg atacaccaa ggaaagtcta   22140 cacgaacct ttggcaaaat cctgtatatc gtgcgaaaaa ggatggatat accgaaaaaa   22200
tcgctataat gaccccgaag cagggttatg cagcggaaaa gcgctgcttc cctgctgttt   22260
tgtggaatat ctaccgactg gaaacaggca aatgcaggaa attactgaac tgaggggaca   22320
ggcgagagac gatgccaaag agctacaccg acgagctggc cgagtgggtt gaatcccgcg   22380
cggccaagaa gcgccggcgt gatgaggctg cggttgcgtt cctggcggtg agggcggatg   22440
tcgaggcggc gttagcgtcc ggctatgcgc tcgtcaccat ttgggagcac atgcgggaaa   22500
cggggaaggt caagttctcc tacgagacgt tccgctcgca cgccaggcgg cacatcaagg   22560
ccaagcccgc cgatgtgccc gcaccgcagg ccaaggctgc ggaacccgcg ccggcaccca   22620
agacgccgga gccacggcgg ccgaagcagg ggggcaaggc tgaaaagccg gccccgctg   22680 cggccccgac cggcttcacc ttcaacccaa caccggacaa aaaggatcta ctgtaatggc   22740
gaaaattcac atggttttgc agggcaaggg cggggtcggc aagtcggcca tcgccgcgat   22800
cattgcgcag tacaagatgg acaagggca gacacccttg tgcatcgaca ccgacccggt   22860
gaacgcgacg ttcgagggct acaaggccct gaacgtccgc cggctgaaca tcatggccgg   22920
cgacgaaatt aactcgcgca acttcgacac cctggtcgag ctgattgcgc cgaccaagga   22980
tgacgtggtg atcgacaacg gtgccagctc gttcgtgcct ctgtcgcatt acctcatcag   23040
caaccaggtg ccggctctgc tgcaagaaat ggggcatgag ctggtcatcc ataccgtcgt   23100
caccggcggc caggctctcc tggacacggt gagcggcttc gcccagctcg ccagccagtt   23160
cccggccgaa gcgcttttcg tggtctggct gaacccgtat tgggggccta tcgagcatga   23220
gggcaagagc tttgagcaga tgaaggcgta cacgccaac aaggcccgcg tgtcgtccat   23280
catccagatt ccgccctca aggaagaaac ctacggccgc gatttcagcg acatgctgca   23340
agagcggctg acgttcgacc aggcgctggc cgatgaatcg ctcacgatca tgacgcggca   23400
```

```
acgcctcaag atcgtgcggc gcggcctgtt tgaacagctc gacgcggcgg ccgtgctatg   23460
agcgaccaga ttgaagagct gatccgggag attgcggcca agcacggcat cgccgtcggc   23520
cgcgacgacc cggtgctgat cctgcatacc atcaacgccc ggctcatggc cgacagtgcg   23580
gccaagcaag aggaaatcct tgccgcgttc aaggaagagc tggaagggat cgcccatcgt   23640
tggggcgagg acgccaaggc caaagcggag cggatgctga acgcggccct ggcggccagc   23700
aaggacgcaa tggcgaaggt aatgaaggac agcgccgcgc aggcggccga agcgatccgc   23760
agggaaatcg acgacggcct tggccgccag ctcgcggcca aggtcgcgga cgcgcggcgc   23820
gtggcgatga tgaacatgat cgccggcggc atggtgttgt tcgcggccgc cctggtggtg   23880
tgggcctcgt tatgaatcgc agaggcgcag atgaaaaagc ccggcgttgc cgggctttgt   23940
ttttgcgtta gctgggcttg tttgacaggc ccaagctctg actgcgcccg cgctcgcgct   24000
cctgggcctg tttcttctcc tgctcctgct tgcgcatcag ggcctggtgc cgtcgggctg   24060
cttcacgcat cgaatcccag tcgccggcca gctcgggatg ctccgcgcgc atcttgcgcg   24120
tcgccagttc ctcgatcttg ggcgcgtgaa tgcccatgcc ttccttgatt tcgcgcacca   24180
tgtccagccg cgtgtgcagg gtctgcaagc gggcttgctg ttgggcctgc tgctgctgcc   24240
aggcggcctt tgtacgcggc agggacagca agccggggc attggactgt agctgctgca   24300
aacgcgcctg ctgacggtct acgagctgtt ctaggcggtc ctcgatgcgc tccacctggt   24360
catgctttgc ctgcacgtag agcgcaaggg tctgctggta ggtctgctcg atgggcgcgg   24420
attctaagag ggcctgctgt tccgtctcgg cctcctgggc cgcctgtagc aaatcctcgc   24480
cgctgttgcc gctggactgc tttactgccg gggactgctg ttgccctgct cgcgccgtcg   24540
tcgcagttcg gcttgccccc actcgattga ctgcttcatt tcgagccgca gcgatgcgat   24600
ctcggattgc gtcaacggac ggggcagcgc ggaggtgtcc ggcttctcct tgggtgagtc   24660
ggtcgatgcc atagccaaag gtttccttcc aaaatgcgtc cattgctgga ccgtgtttct   24720
cattgatgcc cgcaagcatc ttcggcttga ccgccaggtc aagcgcgcct tcatgggcgg   24780
tcatgacgga cgccgccatg accttgccgc cgttgttctc gatgtagccg cgtaatgagg   24840
caatggtgcc gcccatcgtc agcgtgtcat cgacaacgat gtacttctgg ccggggatca   24900
cctcccccctc gaaagtcggg ttgaacgcca ggcgatgatc tgaaccggct ccggttcggg   24960
cgaccttctc ccgctgcaca atgtccgttt cgacctcaag gccaaggcgg tcggccagaa   25020
cgaccgccat catggccgga atcttgttgt tccccgccgc ctcgacggcg aggactggaa   25080
cgatgcgggg cttgtcgtcg ccgatcagcg tcttgagctg gcaacagtg tcgtccgaaa   25140
tcaggcgctc gaccaaatta agcgccgctt ccgcgtcgcc ctgcttcgca gcctggtatt   25200
caggctcgtt ggtcaaagaa ccaaggtcgc cgttgcgaac caccttcggg aagtctcccc   25260
acggtgcgcg ctcggctctg ctgtagctgc tcaagacgcc tccctttta gccgctaaaa   25320
ctctaacgag tgcgcccgcg actcaacttg acgctttcgg cacttacctg tgccttgcca   25380
cttgcgtcat aggtgatgct tttcgcactc ccgatttcag gtactttatc gaaatctgac   25440
cgggcgtgca ttacaaagtt cttccccacc tgttggtaaa tgctgccgct atctgcgtgg   25500
acgatgctgc cgtcgtggcg ctgcgactta tcggccttt gggccatata gatgttgtaa   25560
atgccaggtt tcagggcccc ggctttatct accttctggt tcgtccatgc gccttggttc   25620
tcggtctgga caattctttg cccattcatg accaggaggc ggtgtttcat tgggtgactc   25680
ctgacggttg cctctggtgt taacgtgtc ctggtcgctt gccggctaaa aaaaagccga   25740
cctcggcagt tcgaggccgg cttttcccta gagccgggcgc gtcaaggttg ttccatctat   25800
```

```
tttagtgaac tgcgttcgat ttatcagtta ctttcctccc gctttgtgtt tcctcccact   25860
cgtttccgcg tctagccgac ccctcaacat agcggcctct tcttgggctg cctttgcctc   25920
ttgccgcgct tcgtcacgct cggcttgcac cgtcgtaaag cgctcggcct gcctggccgc   25980
ctcttgcgcc gccaacttcc tttgctcctg gtgggcctcg gcgtcggcct gcgccttcgc   26040
tttcaccgct gccaactccg tgcgcaaact ctccgcttcg cgcctggtgg cgtcgcgctc   26100
gccgcgaagc gcctgcattt cctggttggc cgcgtccagg gtcttgcggc tctcttcttt   26160
gaatgcgcgg gcgtcctggt gagcgtagtc cagctcggcg cgcagctcct gcgctcgacg   26220
ctccacctcg tcggcccgct gcgtcgccag cgcggcccgc tgctcggctc ctgccagggc   26280
ggtgcgtgct tcggccaggg cttgccgctg gcgtgcggcc agctcggccg cctcggcggc   26340
ctgctgctct agcaatgtaa cgcgcgcctg gcttcttcc agctcgcggg cctgcgcctc     26400
gaaggcgtcg gccagctccc cgcgcacggc ttccaactcg ttgcgctcac gatcccagcc   26460
ggcttgcgct gcctgcaacg attcattggc aagggcctgg gcggcttgcc agagggcggc   26520
cacggcctgg ttgccggcct gctgcaccgc gtccggcacc tggactgcca gcggggcggc   26580
ctgcgccgtg cgctggcgtc gccattcgcg catgccggcg ctggcgtcgt tcatgttgac   26640
gcgggcggcc ttacgcactg catccacggt cgggaagttc tcccggtcgc cttgctcgaa   26700
cagctcgtcc gcagccgcaa aaatgcggtc gcgcgtctct ttgttcagtt ccatgttggc   26760
tccggtaatt ggtaagaata ataatactct tacctacctt atcagcgcaa gagtttagct   26820
gaacagttct cgacttaacg gcaggttttt tagcggctga agggcaggca aaaaagccc    26880 cgcacggtcg gcgggggcaa agggtcagcg ggaagggat tagcgggcgt cgggcttctt    26940
catgcgtcgg ggccgcgctt cttgggatgg agcacgacga agcgcgcacg cgcatcgtcc   27000
tcggccctat cggcccgcgt cgcggtcagg aacttgtcgc gcgctaggtc ctccctggtg   27060
ggcaccaggg gcatgaactc ggcctgctcg atgtaggtcc actccatgac cgcatcgcag   27120
tcgaggccgc gttccttcac cgtctcttgc aggtcgcggt acgcccgctc gttgagcggc   27180
tggtaacggg ccaattggtc gtaaatggct gtcggccatg agcggccttt cctgttgagc   27240
cagcagccga cgacgaagcc ggcaatgcag gcccctggca caaccaggcc gacgccgggg   27300
gcaggggatg gcagcagctc gccaaccagg aaccccgccg cgatgatgcc gatgccggtc   27360
aaccagccct tgaaactatc cggccccgaa acacccctgc gcattgcctg gatgctgcgc   27420
cggatagctt gcaacatcag gagccgtttc ttttgttcgt cagtcatggt ccgccctcac   27480
cagttgttcg tatcggtgtc ggacgaactg aaatcgcaag agctgccggt atcggtccag   27540
ccgctgtccg tgtcgctgct gccgaagcac ggcgaggggt ccgcgaacgc gcagacggc    27600 gtatccggcc gcagcgcatc gcccagcatg gccccggtca gcgagccgcc ggccaggtag   27660
cccagcatgg tgctgttggt cgccccggcc accagggccg acgtgacgaa atcgccgtca   27720
ttccctctgg attgttcgct gctcggcggg gcagtgcgcc gcgccggcgg cgtcgtggat   27780
ggctcgggtt ggctggcctg cgacggccgg cgaaaggtgc gcagcagctc gttatcgacc   27840
ggctgcggcg tcggggccgc cgccttgcgc tgcggtcggt gttccttctt cggctcgcgc   27900
agcttgaaca gcatgatcgc ggaaaccagc agcaacgccg cgcctacgcc tcccgcgatg   27960
tagaacagca tcggattcat tcttcggtcc tccttgtagc ggaaccgttg tctgtgcggc   28020
gcgggtggcc cgcgccgctg tctttgggga tcagccctcg atgagcgcga ccagtttcac   28080
gtcggcaagg ttcgcctcga actcctggcc gtcgtcctcg tacttcaacc aggcatagcc   28140
```

```
ttccgccggc ggccgacggt tgaggataag gcgggcaggg cgctcgtcgt gctcgacctg    28200
gacgatggcc tttttcagct tgtccgggtc cggctccttc gcgcccttt ccttggcgtc    28260 cttaccgtcc tggtcgccgt cctcgccgtc ctggccgtcg ccggcctccg cgtcacgctc    28320
ggcatcagtc tggccgttga aggcatcgac ggtgttggga tcgcggccct tctcgtccag    28380
gaactcgcgc agcagcttga ccgtgccgcg cgtgatttcc tgggtgtcgt cgtcaagcca    28440
cgcctcgact tcctccgggc gcttcttgaa ggccgtcacc agctcgttca ccacggtcac    28500
gtcgcgcacg cggccggtgt tgaacgcatc ggcgatcttc tccggcaggt ccagcagcgt    28560
gacgtgctgg gtgatgaacg ccggcgactt gccgatttcc ttggcgatat cgcctttctt    28620
cttgcccttc gccagctcgc ggccaatgaa gtcggcaatt cgcgcgggg tcagctcgtt    28680 gcgttgcagg ttctcgataa cctggtcggc ttcgttgtag tcgttgtcga tgaacgccgg    28740
gatggacttc ttgccggccc acttcgagcc acggtagcgg cgggcgccgt gattgatgat    28800
atagcggccc ggctgctcct ggttctcgcg caccgaaatg ggtgacttca ccccgcgctc    28860
tttgatcgtg gcaccgattt ccgcgatgct ctccggggaa aagccggggt tgtcggccgt    28920
ccgcggctga tgcggatctt cgtcgatcag gtccaggtcc agctcgatag ggccggaacc    28980
gccctgagac gccgcaggag cgtccaggag gctcgacagg tcgccgatgc tatccaaccc    29040
caggccggac ggctgcgccg cgcctgcggc ttcctgagcg gccgcagcgg tgttttcctt    29100
ggtggtcttg gcttgagccg cagtcattgg gaaatctcca tcttcgtgaa cacgtaatca    29160
gccagggcgc gaacctcttt cgatgccttg cgcgcggccg ttttcttgat cttccagacc    29220
ggcacaccgg atgcgagggc atcggcgatg ctgctgcgca ggccaacggt ggccggaatc    29280
atcatcttgg ggtacgcggc cagcagctcg gcttggtggc gcgcgtggcg cggattccgc    29340
gcatcgacct tgctgggcac catgccaagg aattgcagct tggcgttctt ctggcgcacg    29400
ttcgcaatgg tcgtgaccat cttcttgatg ccctggatgc tgtacgcctc aagctcgatg    29460
ggggacagca catagtcggc cgcgaagagg cggccgccca ggccgacgcc aagggtcggg    29520
gccgtgtcga tcaggcacac gtcgaagcct tggttcgcca gggccttgat gttcgccccg    29580
aacagctcgc gggcgtcgtc cagcgacagc cgttcggcgt tcgccagtac cgggttggac    29640
tcgatgaggg cgaggcgcgc ggcctggccg tcgccggctg cgggtgcggt ttcggtccag    29700
ccgccggcag ggacagcgcc gaacagcttg cttgcatgca ggccggtagc aaagtccttg    29760
agcgtgtagg acgcattgcc ctgggggtcc aggtcgatca cggcaacccg caagccgcgc    29820
tcgaaaaagt cgaaggcaag atgcacaagg gtcgaagtct tgccgacgcc gccttttctgg   29880 ttggccgtga ccaaagttttt catcgtttgg tttcctgttt tttcttggcg tccgcttccc    29940
acttccggac gatgtacgcc tgatgttccg gcagaaccgc cgttacccgc gcgtacccct    30000
cgggcaagtt cttgtcctcg aacgcggccc acacgcgatg caccgcttgc gacactgcgc    30060
ccctggtcag tccagcgac gttgcgaacg tcgcctgtgg cttcccatcg actaagacgc    30120
cccgcgctat ctcgatggtc tgctgcccca cttccagccc ctggatcgcc tcctggaact    30180
ggctttcggt aagccgtttc ttcatggata cacccataa tttgctccgc gccttggttg    30240
aacatagcgc tgcagccgc cagcacatga gagaagttta gctaaacatt tctcgcacgt    30300
caacaccttt agccgctaaa actcgtcctt ggcgtaacaa aacaaaagcc cggaaaccgg    30360
gctttcgtct cttgccgctt atggctctgc accggctcc atcaccaaca ggtcgcgcac    30420
gcgcttcact cggttgcgga tcgacactgc cagcccaaca aagccggttg ccgccgcgc    30480 caggatcgcg ccgatgatgc cggccacacc ggccatcgcc caccaggtcg ccgccttccg    30540
```

```
gttccattcc tgctggtact gcttcgcaat gctggacctc ggctcaccat aggctgaccg    30600
ctcgatggcg tatgccgctt ctccccttgg cgtaaaaccc agcgccgcag gcggcattgc    30660
catgctgccc gccgctttcc cgaccacgac gcgcgcacca ggcttgcggt ccagaccttc    30720
ggccacggcg agctgcgcaa ggacataatc agccgccgac ttggctccac gcgcctcgat    30780
cagctcttgc actcgcgcga aatccttggc ctccacggcc gccatgaatc gcgcacgcgg    30840
cgaaggctcc gcagggccgg cgtcgtgatc gccgccgaga atgcccttca ccaagttcga    30900
cgacacgaaa atcatgctga cggctatcac catcatgcag acggatcgca cgaacccgct    30960
gaattgaaca cgagcacggc acccgcgacc actatgccaa gaatgcccaa ggtaaaaatt    31020
gccggccccg ccatgaagtc cgtgaatgcc ccgacggccg aagtgaaggg caggccgcca    31080
cccaggccgc cgccctcact gccggcacc tggtcgctga atgtcgatgc cagcacctgc    31140
ggcacgtcaa tgcttccggg cgtcgcgctc gggctgatcg cccatcccgt tactgccccg    31200
atcccggcaa tggcaaggac tgccagcgct gccattttg gggtgaggcc gttcgcggcc    31260
gaggggcgca gcccctgggg ggatgggagg cccgcgttag cgggccggga gggttcgaga    31320 aggggggca cccccttcg gcgtgcgcgg tcacgcgcac agggcgcagc cctggttaaa    31380
aacaaggttt ataaatattg gtttaaaagc aggttaaaag acaggttagc ggtggccgaa    31440
aaacgggcgg aaacccttgc aaatgctgga ttttctgcct gtggacagcc cctcaaatgt    31500
caataggtgc gcccctcatc tgtcagcact ctgcccctca agtgtcaagg atcgcgcccc    31560
tcatctgtca gtagtcgcgc ccctcaagtg tcaataccgc agggcactta tccccaggct    31620
tgtccacatc atctgtggga aactcgcgta aaatcaggcg ttttcgccga tttgcgaggc    31680
tggccagctc cacgtcgccg gccgaaatcg agcctgcccc tcatctgtca acgccgcgcc    31740
gggtgagtcg gcccctcaag tgtcaacgtc cgcccctcat ctgtcagtga gggccaagtt    31800
ttccgcgagg tatccacaac gccggcggcc gcggtgtctc gcacacggct tcgacggcgt    31860
ttctggcgcg tttgcagggc catagacggc cgccagccca gcggcgaggg caaccagccc    31920
ggtgagcgtc ggaaaggcgc tggaagcccc gtagcgacgc ggagaggggc gagacaagcc    31980
aagggcgcag gctcgatgcg cagcacgaca tagccggttc tcgcaaggac gagaatttcc    32040
ctgcggtgcc cctcaagtgt caatgaaagt ttccaacgcg agccattcgc gagagccttg    32100
agtccacgct agatgagagc tttgttgtag gtggaccagt tggtgatttt gaactttgc    32160 tttgccacgg aacggtctgc gttgtcggga agatgcgtga tctgatcctt caactcagca    32220
aaagttcgat ttattcaaca aagccacgtt gtgtctcaaa atctctgatg ttacattgca    32280
caagataaaa atatatcatc atgaacaata aaactgtctg cttacataaa cagtaataca    32340
aggggtgtta tgagccatat tcaacgggaa acgtcttgct cgactctaga gctcgttcct    32400
cgaggcctcg aggcctcgag gaacggtacc tgcgggaag cttacaataa tgtgtgttgt    32460
taagtcttgt tgcctgtcat cgtctgactg actttcgtca taaatcccgg cctccgtaac    32520
ccagctttgg gcaagctcac ggatttgatc cggcggaacg ggaatatcga gatgccgggc    32580
tgaacgctgc agttccagct ttcccttcg ggacaggtac tccagctgat tgattatctg    32640
ctgaagggtc ttggttccac ctcctggcac aatgcgaatg attacttgag cgcgatcggg    32700 catccaatt tctcccgtca ggtgcgtggt caagtgctac aaggcacctt tcagtaacga    32760
gcgaccgtcg atccgtcgcc gggatacgga caaaatggag cgcagtagtc catcgagggc    32820
ggcgaaagcc tcgccaaaag caatacgttc atctcgcaca gcctccagat ccgatcgagg    32880
```

```
gtcttcggcg taggcagata gaagcatgga tacattgctt gagagtattc cgatggactg   32940
aagtatggct tccatctttt ctcgtgtgtc tgcatctatt tcgagaaagc ccccgatgcg   33000
gcgcaccgca acgcgaattg ccatactatc cgaaagtccc agcaggcgcg cttgatagga   33060
aaaggtttca tactcggccg atcgcagacg ggcactcacg accttgaacc cttcaacttt   33120
cagggatcga tgctggttga tggtagtctc actcgacgtg gctctggtgt gttttgacat   33180
agcttcctcc aaagaaagcg gaaggtctgg atactccagc acgaaatgtg cccgggtaga   33240
cggatggaag tctagccctg ctcaatatga aatcaacagt acatttacag tcaatactga   33300
atatacttgc tacatttgca attgtcttat aacgaatgtg aaataaaaat agtgtaacaa   33360
cgcttttact catcgataat cacaaaaaca tttatacgaa caaaaataca aatgcactcc   33420
ggtttcacag gataggcggg atcagaatat gcaacttttg acgttttgtt ctttcaaagg   33480
gggtgctggc aaaaccaccg cactcatggg cctttgcgct gctttggcaa atgacggtaa   33540
acgagtggcc ctctttgatg ccgacgaaaa ccggcctctg acgcgatgga gagaaaacgc   33600
cttacaaagc agtactggga tcctcgctgt gaagtctatt ccgccgacga aatgcccctt   33660
cttgaagcag cctatgaaaa tgccgagctc gaaggatttg attatgcgtt ggccgatacg   33720
cgtggcggct cgagcgagct caacaacaca atcatcgcta gctcaaacct gcttctgatc   33780
cccaccatgc taacgccgct cgacatcgat gaggcactat ctacctaccg ctacgtcatc   33840
gagctgctgt tgagtgaaaa tttggcaatt cctacagctg ttttgcgcca acgcgtcccg   33900
gtcggccgat tgacaacatc gcaacgcagg atgtcagaga cgctagagag ccttccagtt   33960
gtaccgtctc ccatgcatga aagagatgca tttgccgcga tgaaagaacg cggcatgttg   34020
catcttacat tactaaacac gggaactgat ccgacgatgc gcctcataga gaggaatctt   34080
cggattgcga tggaggaagt cgtggtcatt tcgaaactga tcagcaaaat cttggaggct   34140
tgaagatggc aattcgcaag cccgcattgt cggtcggcga agcacggcgg cttgctggtg   34200
ctcgacccga gatccaccat cccaacccga cacttgttcc ccagaagctg gacctccagc   34260
acttgcctga aaaagccgac gagaaagacc agcaacgtga gcctctcgtc gccgatcaca   34320
tttacagtcc cgatcgacaa cttaagctaa ctgtggatgc ccttagtcca cctccgtccc   34380
cgaaaaagct ccaggttttt cttttcagcgc gaccgcccgc gcctcaagtg tcgaaaacat   34440
atgacaacct cgttcggcaa tacagtccct cgaagtcgct acaaatgatt ttaaggcgcg   34500
cgttggacga tttcgaaagc atgctggcag atggatcatt tcgcgtggcc ccgaaaagtt   34560
atccgatccc ttcaactaca gaaaaatccg ttctcgttca gacctcacgc atgttcccgg   34620
ttgcgttgct cgaggtcgct cgaagtcatt ttgatccgtt ggggttggag accgctcgag   34680 cttcggcca caagctggct accgccgcgc tcgcgtcatt cttgctgga gagaagccat   34740 cgagcaattg gtgaagaggg acctatcgga accccctcacc aaatattgag tgtaggtttg   34800
aggccgctgg ccgcgtcctc agtcacctttt gagccagat aattaagagc caaatgcaat   34860
tggctcaggc tgccatcgtc cccccgtgcg aaacctgcac gtccgcgtca aagaaataac   34920
cggcacctct tgctgttttt atcagttgag ggcttgacgg atccgcctca gtttgcggc   34980 gcagccgcaa aatgagaaca tctatactcc tgtcgtaaac ctcctcgtcg cgtactcgac   35040
tggcaatgag aagttgctcg cgcgatagaa cgtcgcgggg tttctctaaa aacgcgagga   35100
gaagattgaa ctcacctgcc gtaagtttca cctcaccgcc agcttcggac atcaagcgac   35160
gttgcctgag attaagtgtc cagtcagtaa aacaaaaaga ccgtcggtct ttggagcgga   35220
caacgttggg gcgcacgcgc aaggcaaccc gaatgcgtgc aagaaactct ctcgtactaa   35280
```

```
acggcttagc gataaaatca cttgctccta gctcgagtgc aacaacttta tccgtctcct   35340
caaggcggtc gccactgata attatgattg gaatatcaga ctttgccgcc agatttcgaa   35400
cgatctcaag cccatcttca cgacctaaat ttagatcaac aaccacgaca tcgaccgtcg   35460
cggaagagag tactctagtg aactgggtgc tgtcggctac cgcggtcact ttgaaggcgt   35520
ggatcgtaag gtattcgata ataagatgcc gcatagcgac atcgtcatcg ataagaagaa   35580
cgtgtttcaa cggctcacct ttcaatctaa aatctgaacc cttgttcaca gcgcttgaga   35640
aattttcacg tgaaggatgt acaatcatct ccagctaaat gggcagttcg tcagaattgc   35700
ggctgaccgc ggatgacgaa aatgcgaacc aagtatttca attttatgac aaaagttctc   35760
aatcgttgtt acaagtgaaa cgcttcgagg ttacagctac tattgattaa ggagatcgcc   35820
tatggtctcg ccccggcgtc gtgcgtccgc cgcgagccag atctcgccta cttcataaac   35880
gtcctcatag gcacggaatg gaatgatgac atcgatcgcc gtagagagca tgtcaatcag   35940
tgtgcgatct tccaagctag caccttgggc gctacttttg acaagggaaa acagtttctt   36000
gaatccttgg attggattcg cgccgtgtat tgttgaaatc gatcccggat gtcccgagac   36060
gacttcactc agataagccc atgctgcatc gtcgcgcatc tcgccaagca atatccggtc   36120
cggccgcata cgcagacttg cttggagcaa gtgctcggcg ctcacagcac ccagcccagc   36180
accgttcttg gagtagagta gtctaacatg attatcgtgt ggaatgacga gttcgagcgt   36240
atcttctatg gtgattagcc tttcctgggg ggggatggcg ctgatcaagg tcttgctcat   36300
tgttgtcttg ccgcttccgg tagggccaca tagcaacatc gtcagtcggc tgacgacgca   36360
tgcgtgcaga aacgcttcca aatccccgtt gtcaaaatgc tgaaggatag cttcatcatc   36420
ctgattttgg cgtttccttc gtgtctgcca ctggttccac ctcgaagcat cataacggga   36480
ggagacttct ttaagaccag aaacacgcga gcttggccgt cgaatggtca agctgacggt   36540
gcccgaggga acgtcggcg gcagacagat ttgtagtcgt tcaccaccag gaagttcagt   36600
ggcgcagagg gggttacgtg gtccgacatc ctgctttctc agcgcgcccg ctaaaatagc   36660
gatatcttca agatcatcat aagagacggg caaaggcatc ttggtaaaaa tgccggcttg   36720
gcgcacaaat gcctctccag gtcgattgat cgcaatttct tcagtcttcg ggtcatcgag   36780
ccattccaaa atcggcttca gaagaaagcg tagttgcgga tccacttcca tttacaatgt   36840
atcctatctc taagcggaaa tttgaattca ttaagagcgg cggttcctcc cccgcgtggc   36900
gccgccagtc aggcggagct ggtaaacacc aaagaaatcg aggtcccgtg ctacgaaaat   36960
ggaaacggtg tcaccctgat tcttcttcag ggttggcggt atgttgatgg ttgccttaag   37020
ggctgtctca gttgtctgct caccgttatt ttgaaagctg ttgaagctca tcccgccacc   37080
cgagctgccg gcgtaggtgc tagctgcctg gaaggcgcct tgaacaacac tcaagagcat   37140
agctccgcta aaacgctgcc agaagtggct gtcgaccgag cccggcaatc ctgagcgacc   37200
gagttcgtcc gcgcttggcg atgttaacga gatcatcgca tggtcaggtg tctcggcgcg   37260
atcccacaac acaaaaacgc gcccatctcc ctgttgcaag ccacgctgta tttcgccaac   37320
aacggtggtg ccacgatcaa gaagcacgat attgttcgtt gttccacgaa tatcctgagg   37380
caagacacac tttacatagc ctgccaaatt tgtgtcgatt gcggtttgca agatgcacgg   37440
aattattgtc ccttgcgtta ccataaaatc ggggtgcggc aagagcgtgg cgctgctggg   37500
ctgcagctcg gtgggtttca tacgtatcga caaatcgttc tcgccggaca cttcgccatt   37560
cggcaaggag ttgtcgtcac gcttgccttc ttgtcttcgg cccgtgtcgc cctgaatggc   37620
```

```
gcgtttgctg accccttgat cgccgctgct atatgcaaaa atcggtgttt cttccggccg    37680
tggctcatgc cgctccggtt cgcccctcgg cggtagagga gcagcaggct gaacagcctc    37740
ttgaaccgct ggaggatccg gcggcacctc aatcggagct ggatgaaatg gcttggtgtt    37800
tgttgcgatc aaagttgacg gcgatgcgtt ctcattcacc ttcttttggc gcccacctag    37860
ccaaatgagg cttaatgata acgcgagaac gacacctccg acgatcaatt tctgagaccc    37920
cgaaagacgc cggcgatgtt tgtcggagac cagggatcca gatgcatcaa cctcatgtgc    37980
cgcttgctga ctatcgttat tcatcccttc gccccttca ggacgcgttt cacatcgggc     38040
ctcaccgtgc ccgtttgcgg ccttttggcca acgggatcgt aagcggtgtt ccagatacat    38100
agtactgtgt ggccatccct cagacgccaa cctcgggaaa ccgaagaaat ctcgacatcg    38160
ctcccttta ctgaatagtt ggcaacagct tccttgccat caggattgat ggtgtagatg     38220
gagggtatgc gtacattgcc cggaaagtgg aataccgtcg taaatccatt gtcgaagact    38280
tcgagtggca acagcgaacg atcgccttgg gcgacgtagt gccaattact gtccgccgca    38340
ccaagggctg tgacaggctg atccaataaa ttctcagctt tccgttgata ttgtgcttcc    38400
gcgtgtagtc tgtccacaac agccttctgt tgtgcctccc ttcgccgagc cgccgcatcg    38460
tcggcggggt aggcgaattg gacgctgtaa tagagatcgg gctgctcttt atcgaggtgg    38520
gacagagtct tggaacttat actgaaaaca taacggcgca tcccggagtc gcttgcggtt    38580
agcacgatta ctggctgagg cgtgaggacc tggcttgcct tgaaaaatag ataatttccc    38640
cgcggtaggg ctgctagatc tttgctattt gaaacggcaa ccgctgtcac cgtttcgttc    38700
gtggcgaatg ttacgaccaa agtagctcca accgccgtcg agaggcgcac cacttgatcg    38760
ggattgtaag ccaaataacg catgcgcgga tctagcttgc ccgccattgg agtgtcttca    38820
gcctccgcac cagtcgcagc ggcaaataaa catgctaaaa tgaaaagtgc ttttctgatc    38880
atggttcgct gtggcctacg tttgaaacgg tatcttccga tgtctgatag gaggtgacaa    38940
ccagacctgc cgggttggtt agtctcaatc tgccgggcaa gctggtcacc ttttcgtagc    39000
gaactgtcgc ggtccacgta ctcaccacag gcattttgcc gtcaacgacg agggtccttt    39060
tatagcgaat ttgctgcgtg cttggagtta catcatttga agcgatgtgc tcgacctcca    39120
ccctgccgcg tttgccaaga atgacttgag gcgaactggg attgggatag ttgaagaatt    39180
gctggtaatc ctgcgcact gttggggcac tgaagttcga taccaggtcg taggcgtact    39240
gagcggtgtc ggcatcataa ctctcgcgca ggcgaacgta ctcccacaat gaggcgttaa    39300
cgacggcctc ctcttgagtt gcaggcaatc gcgagacaga cacctcgctg tcaacggtgc    39360
cgtccggccg tatccataga tatacgggca caagcctgct caacggcacc attgtggcta    39420
tagcgaacgc ttgagcaaca tttcccaaaa tcgcgatagc tgcgacagct gcaatgagtt    39480
tggagagacg tcgcgccgat ttcgctcgcg cggtttgaaa ggcttctact tccttatagt    39540
gctcggcaag gctttcgcgc gccactagca tggcatattc aggccccgtc atagcgtcca    39600
cccgaattgc cgagctgaag atctgacgga gtaggctgcc atcgcccac attcagcggg     39660
aagatcgggc ctttgcagct cgctaatgtg tcgtttgtct ggcagccgct caaagcgaca    39720
actaggcaca gcaggcaata cttcatagaa ttctccattg aggcgaattt ttgcgcgacc    39780
tagcctcgct caacctgagc gaagcgacgg tacaagctgc tggcagattg ggttgcgccg    39840
ctccagtaac tgcctccaat gttgccggcg atcgccggca aagcgacaat gagcgcatcc    39900
cctgtcagaa aaaacatatc gagttcgtaa agaccaatga tcttggccgc ggtcgtaccg    39960
gcgaaggtga ttacaccaag cataagggtg agcgcagtcg cttcggttag gatgacgatc    40020
```

```
gttgccacga ggtttaagag gagaagcaag agaccgtagg tgataagttg cccgatccac   40080
ttagctgcga tgtcccgcgt gcgatcaaaa atatatccga cgaggatcag aggcccgatc   40140
gcgagaagca ctttcgtgag aattccaacg gcgtcgtaaa ctccgaaggc agaccagagc   40200
gtgccgtaaa ggacccactg tgccccttgg aaagcaagga tgtcctggtc gttcatcgga   40260
ccgatttcgg atgcgatttt ctgaaaaacg gcctgggtca cggcgaacat tgtatccaac   40320
tgtgccggaa cagtctgcag aggcaagccg gttacactaa actgctgaac aaagtttggg   40380
accgtctttt cgaagatgga aaccacatag tcttggtagt tagcctgccc aacaattaga   40440
gcaacaacga tggtgaccgt gatcacccga gtgataccgc tacgggtatc gacttcgccg   40500
cgtatgacta aaatacccctg aacaataatc aaagagtga cacaggcgat caatggcgca   40560
ctcaccgcct cctggatagt ctcaagcatc gagtccaagc ctgtcgtgaa ggctacatcg   40620
aagatcgtat gaatggccgt aaacggcgcc ggaatcgtga aattcatcga ttggacctga   40680
acttgactgg tttgtcgcat aatgttggat aaaatgagct cgcattcggc gaggatgcgc   40740
gcggatgaac aaatcgccca gccttagggg agggcaccaa agatgacagc ggtctttga   40800 tgctccttgc gttgagcggc cgcctcttcc gcctcgtgaa ggccggcctg cgcggtagtc   40860
atcgttaata ggcttgtcgc ctgtacattt tgaatcattg cgtcatggat ctgcttgaga   40920
agcaaaccat tggtcacggt tgcctgcatg atattgcgag atcgggaaag ctgagcagac   40980
gtatcagcat tcgccgtcaa gcgtttgtcc atcgtttcca gattgtcagc cgcaatgcca   41040
gcgctgtttg cggaaccggt gatctgcgat cgcaacaggt ccgcttcagc atcactaccc   41100
acgactgcac gatctgtatc gctggtgatc gcacgtgccg tggtcgacat tggcattcgc   41160
ggcgaaaaca tttcattgtc taggtccttc gtcgaaggat actgattttt ctggttgagc   41220
gaagtcagta gtccagtaac gccgtaggcc gacgtcaaca tcgtaaccat cgctatagtc   41280
tgagtgagat tctccgcagt cgcgagcgca gtcgcgagcg tctcagcctc cgttgccggg   41340
tcgctaacaa caaactgcgc ccgcgcgggc tgaatatata gaaagctgca ggtcaaaact   41400
gttgcaataa gttgcgtcgt cttcatcgtt tcctacctta tcaatcttct gcctcgtggt   41460
gacgggccat gaattcgctg agccagccag atgagttgcc ttcttgtgcc tcgcgtagtc   41520
gagttgcaaa gcgcaccgtg ttggcacgcc ccgaaagcac ggcgacatat tcacgcatat   41580
cccgcagatc aaattcgcag atgacgcttc cactttctcg tttaagaaga aacttacggc   41640
tgccgaccgt catgtcttca cggatcgcct gaaattcctt ttcggtacat ttcagtccat   41700
cgacataagc cgatcgatct gcggttggtg atggatagaa aatcttcgtc atacattgcg   41760
caaccaagct ggctcctagc ggcgattcca aacatgctc tggttgctgc gttgccagta   41820
ttagcatccc gttgtttttt cgaacggtca ggaggaattt gtcgacgaca gtcgaaaatt   41880
tagggtttaa caaataggcg cgaaaactcat cgcagctcat cacaaaacgg cggccgtcga   41940
tcatggctcc aatccgatgc aggagatatg ctgcagcggg agcgcatact tcctcgtatt   42000
cgagaagatg cgtcatgtcg aagccggtaa tcgacggatc taactttact tcgtcaactt   42060
cgccgtcaaa tgcccagcca agcgcatggc cccggcacca gcgttggagc gcgcgctcctg   42120 cgccttcggc gggcccatgc aacaaaaatt cacgtaaccc cgcgattgaa cgcatttgtg   42180
gatcaaacga gagctgacga tggataccac ggaccagacg gcggttctct tccggagaaa   42240 tcccacccccg accatcactc tcgatgagag ccacgatcca ttcgcgcaga aaatcgtgtg   42300
aggctgctgt gttttctagg ccacgcaacg gcgccaaccc gctgggtgtg cctctgtgaa   42360
```

```
gtgccaaata tgttcctcct gtggcgcgaa ccagcaattc gccaccccgg tccttgtcaa   42420
agaacacgac cgtacctgca cggtcgacca tgctctgttc gagcatggct agaacaaaca   42480
tcatgagcgt cgtcttaccc ctcccgatag gcccgaatat tgccgtcatg ccaacatcgt   42540
gctcatgcgg gatatagtcg aaaggcgttc cgccattggt acgaaatcgg gcaatcgcgt   42600
tgccccagtg gcctgagctg gcgccctctg gaaagttttc gaaagagaca aaccctgcga   42660
aattgcgtga agtgattgcg ccagggcgtg tgcgccactt aaaattcccc ggcaattggg   42720
accaataggc cgcttccata ccaatacctt cttggacaac cacggcacct gcatccgcca   42780
ttcgtgtccg agcccgcgcg cccctgtccc caagactatt gagatcgtct gcatagacgc   42840
aaaggctcaa atgatgtgag cccataacga attcgttgct cgcaagtgcg tcctcagcct   42900
cggataattt gccgatttga gtcacggctt tatcgccgga actcagcatc tggctcgatt   42960
tgaggctaag tttcgcgtgc gcttgcgggc gagtcaggaa cgaaaaactc tgcgtgagaa   43020
caagtggaaa atcgagggat agcagcgcgt tgagcatgcc cggccgtgtt tttgcagggt   43080
attcgcgaaa cgaatagatg gatccaacgt aactgtcttt tggcgttctg atctcgagtc   43140
ctcgcttgcc gcaaatgact ctgtcggtat aaatcgaagc gccgagtgag ccgctgacga   43200
ccggaaccgg tgtgaaccga ccagtcatga tcaaccgtag cgcttcgcca atttcggtga   43260
agagcacacc ctgcttctcg cggatgccaa gacgatgcag gccatacgct ttaagagagc   43320
cagcgacaac atgccaaaga tcttccatgt tcctgatctg gcccgtgaga tcgttttccc   43380
tttttccgct tagcttggtg aacctcctct ttaccttccc taaagccgcc tgtgggtaga   43440
caatcaacgt aaggaagtgt tcattgcgga ggagttggcc ggagagcacg cgctgttcaa   43500
aagcttcgtt caggctagcg gcgaaaacac tacggaagtg tcgcggcgcc gatgatggca   43560
cgtcggcatg acgtacgagg tgagcatata ttgacacatg atcatcagcg atattgcgca   43620
acagcgtgtt gaacgcacga caacgcgcat tgcgcatttc agtttcctca agctcgaatg   43680
caacgccatc aattctcgca atggtcatga tcgatccgtc ttcaagaagg acgatatggt   43740
cgctgaggtg gccaatataa gggagataga tctcaccgga tctttcggtc gttccactcg   43800
cgccgagcat cacaccattc ctctccctcg tgggggaacc ctaattggat ttgggctaac   43860
agtagcgccc ccccaaactg cactatcaat gcttcttccc gcggtccgca aaaatagcag   43920
gacgacgctc gccgcattgt agtctcgctc cacgatgagc cgggctgcaa accataacgg   43980
cacgagaacg acttcgtaga gcgggttctg aacgataacg atgacaaagc cggcgaacat   44040
catgaataac cctgccaatg tcagtggcac cccaagaaac aatgcgggcc gtgtggctgc   44100
gaggtaaagg gtcgattctt ccaaacgatc agccatcaac taccgccagt gagcgtttgg   44160
ccgaggaagc tcgcccccaaa catgataaca atgccgccga cgacgccggc aaccagccca   44220
agcgaagccc gcccgaacat ccaggagatc ccgatagcga caatgccgag aacagcgagt   44280
gactggccga acgaccaag gataaacgtg catatattgt taaccattgt ggcgggtca   44340 gtgccgccac ccgcagattg cgctgcggcg ggtccggatg aggaaatgct ccatgcaatt   44400
gcaccgcaca agcttggggc gcagctcgat atcacgcgca tcatcgcatt cgagagcgag   44460
aggcgattta gatgtaaacg gtatctctca aagcatcgca tcaatgcgca cctccttagt   44520
ataagtcgaa taagacttga ttgtcgtctg cggatttgcc gttgtcctgg tgtggcggtg   44580
gcggagcgat taaaccgcca gcgccatcct cctgcgagcg gcgctgatat gaccccccaaa   44640 catcccacgt ctcttcggat tttagcgcct cgtgatcgtc ttttggaggc tcgattaacg   44700
cgggcaccag cgattgagca gctgtttcaa cttttcgcac gtagccgttt gcaaaaccgc   44760
```

```
cgatgaaatt accggtgttg taagcggaga tcgcccgacg aagcgcaaat tgcttctcgt    44820
caatcgtttc gccgcctgca taacgacttt tcagcatgtt tgcagcggca gataatgatg    44880
tgcacgcctg gagcgcaccg tcaggtgtca gaccgagcat agaaaaattt cgagagttta    44940
tttgcatgag gccaacatcc agcgaatgcc gtgcatcgag acggtgcctg acgacttggg    45000
ttgcttggct gtgatcttgc cagtgaagcg tttcgccggt cgtgttgtca tgaatcgcta    45060
aaggatcaaa gcgactctcc accttagcta tcgccgcaag cgtagatgtc gcaactgatg    45120
gggcacactt gcgagcaaca tggtcaaact cagcagatga gagtggcgtg gcaaggctcg    45180
acgaacagaa ggagaccatc aaggcaagag aaagcgaccc cgatctctta agcatacctt    45240
atctccttag ctcgcaacta acaccgcctc tcccgttgga agaagtgcgt tgttttatgt    45300
tgaagattat cgggagggtc ggttactcga aaattttcaa ttgcttcttt atgatttcaa    45360
ttgaagcgag aaacctcgcc cggcgtcttg aacgcaaca tggaccgaga accgcgcatc    45420
catgactaag caaccggatc gacctattca ggccgcagtt ggtcaggtca ggctcagaac    45480
gaaaatgctc ggcgaggtta cgctgtctgt aaacccattc gatgaacggg aagcttcctt    45540
ccgattgctc ttggcaggaa tattggccca tgcctgcttg cgctttgcaa atgctcttat    45600
cgcgttggta tcatatgcct tgtccgccag cagaaacgca ctctaagcga ttatttgtaa    45660
aaatgtttcg gtcatgcggc ggtcatgggc ttgacccgct gtcagcgcaa gacggatcgg    45720
tcaaccgtcg gcatcgacaa cagcgtgaat cttggtggtc aaaccgccac gggaacgtcc    45780
catacagcca tcgtcttgat cccgctgttt cccgtcgccg catgttggtg gacgcggaca    45840
caggaactgt caatcatgac gacattctat cgaaagcctt ggaaatcaca ctcagaatat    45900
gatcccagac gtctgcctca cgccatcgta caaagcgatt gtagcaggtt gtacaggaac    45960
cgtatcgatc aggaacgtct gcccagggcg ggcccgtccg gaagcgccac aagatgacat    46020
tgatcacccg cgtcaacgcg cggcacgcga cgcggcttat ttgggaacaa aggactgaac    46080
aacagtccat tcgaaatcgg tgacatcaaa gcggggacgg gttatcagtg gcctccaagt    46140
caagcctcaa tgaatcaaaa tcagaccgat ttgcaaacct gatttatgag tgtgcggcct    46200
aaatgatgaa atcgtccttc tagatcgcct ccgtggtgta gcaacacctc gcagtatcgc    46260
cgtgctgacc ttggccaggg aattgactgg caagggtgct ttcacatgac cgctcttttg    46320
gccgcgatag atgatttcgt tgctgctttg ggcacgtaga aggagagaag tcatatcgga    46380
gaaattcctc ctggcgcgag agcctgctct atcgcgacgg catcccactg tcgggaacag    46440
accggatcat tcacgaggcg aaagtcgtca acacatgcgt tataggcatc ttcccttgaa    46500
ggatgatctt gttgctgcca atctggaggt gcggcagccg caggcagatg cgatctcagc    46560
gcaacttgcg gcaaaacatc tcactcacct gaaaaccact agcgagtctc gcgatcagac    46620
gaaggccttt tacttaacga cacaatatcc gatgtctgca tcacaggcgt cgctatccca    46680
gtcaatacta aagcggtgca ggaactaaag attactgatg acttaggcgt gccacgaggc    46740
ctgagacgac gcgcgtagac agttttttga aatcattatc aaagtgatgg cctccgctga    46800
agcctatcac ctctgcgccg gtctgtcgga gagatgggca agcattatta cggtcttcgc    46860
gcccgtacat gcattggacg attgcagggt caatggatct gagatcatcc agaggattgc    46920
cgcccttacc ttccgtttcg agttggagcc agcccctaaa tgagacgaca tagtcgactt    46980
gatgtgacaa tgccaagaga gagatttgct taacccgatt tttttgctca agcgtaagcc    47040
tattgaagct tgccggcatg acgtccgcgc cgaaagaata tcctacaagt aaaacattct    47100
```

| | | | | | |
|---|---|---|---|---|---|
| gcacaccgaa | atgcttggtg | tagacatcga | ttatgtgacc | aagatcctta | gcagtttcgc | 47160 |
| ttggggaccg | ctccgaccag | aaataccgaa | gtgaactgac | gccaatgaca | ggaatccctt | 47220 |
| ccgtctgcag | ataggtacca | tcgatagatc | tgctgcctcg | cgcgtttcgg | tgatgacggt | 47280 |
| gaaaacctct | gacacatgca | gctcccggag | acggtcacag | cttgtctgta | agcggatgcc | 47340 |
| gggagcagac | aagcccgtca | gggcgcgtca | gcgggtgttg | gcgggtgtcg | ggcgcagcc | 47400 |
| atgacccagt | cacgtagcga | tagcggagtg | tatactggct | taactatgcg | gcatcagagc | 47460 |
| agattgtact | gagagtgcac | catatgcggt | gtgaaatacc | gcacagatgc | gtaaggagaa | 47520 |
| aataccgcat | caggcgctct | tccgcttcct | cgctcactga | ctcgctgcgc | tcggtcgttc | 47580 |
| ggctgcggcg | agcggtatca | gctcactcaa | aggcggtaat | acggttatcc | acagaatcag | 47640 |
| gggataacgc | aggaaagaac | atgtgagcaa | aaggccagca | aaaggccagg | aaccgtaaaa | 47700 |
| aggccgcgtt | gctggcgttt | ttccataggc | tccgcccccc | tgacgagcat | cacaaaaatc | 47760 |
| gacgctcaag | tcagaggtgg | cgaaacccga | caggactata | aagataccag | gcgtttcccc | 47820 |
| ctggaagctc | cctcgtgcgc | tctcctgttc | cgaccctgcc | gcttaccgga | tacctgtccg | 47880 |
| cctttctccc | ttcgggaagc | gtggcgcttt | ctcatagctc | acgctgtagg | tatctcagtt | 47940 |
| cggtgtaggt | cgttcgctcc | aagctgggct | gtgtgcacga | accccccgtt | cagcccgacc | 48000 |
| gctgcgcctt | atccggtaac | tatcgtcttg | agtccaaccc | ggtaagacac | gacttatcgc | 48060 |
| cactggcagc | agccactggt | aacaggatta | gcagagcgag | gtatgtaggc | ggtgctacag | 48120 |
| agttcttgaa | gtggtggcct | aactacggct | acactagaag | gacagtattt | ggtatctgcg | 48180 |
| ctctgctgaa | gccagttacc | ttcggaaaaa | gagttggtag | ctcttgatcc | ggcaaacaaa | 48240 |
| ccaccgctgg | tagcggtggt | ttttttgttt | gcaagcagca | gattacgcgc | agaaaaaaag | 48300 |
| gatctcaaga | agatcctttg | atcttttcta | cggggtctga | cgctcagtgg | aacgaaaact | 48360 |
| cacgttaagg | gattttggtc | atgagattat | caaaaaggat | cttcacctag | atccttttaa | 48420 |
| attaaaaatg | aagttttaaa | tcaatctaaa | gtatatatga | gtaaacttgg | tctgacagtt | 48480 |
| accaatgctt | aatcagtgag | gcacctatct | cagcgatctg | tctatttcgt | tcatccatag | 48540 |
| ttgcctgact | ccccgtcgtg | tagataacta | cgatacggga | gggcttacca | tctggcccca | 48600 |
| gtgctgcaat | gataccgcga | gacccacgct | caccggctcc | agatttatca | gcaataaacc | 48660 |
| agccagccgg | aagggccgag | cgcagaagtg | gtcctgcaac | tttatccgcc | tccatccagt | 48720 |
| ctattaattg | ttgccgggaa | gctagagtaa | gtagttcgcc | agttaatagt | ttgcgcaacg | 48780 |
| ttgttgccat | tgctgcaggg | gggggggggg | gggggacttc | ccattgttca | ttccacggac | 48840 |
| aaaaacagag | aaaggaaacg | acagaggcca | aaaagcctcg | ctttcagcac | ctgtcgtttc | 48900 |
| ctttcttttc | agagggtatt | ttaaataaaa | acattaagtt | atgacgaaga | agaacgaaaa | 48960 |
| cgccttaaac | cggaaaattt | tcataaatag | cgaaaacccg | cgaggtcgcc | gccccgtaac | 49020 |
| ctgtcggatc | accggaaagg | acccgtaaag | tgataatgat | tatcatctac | atatcacaac | 49080 |
| gtgcgtggag | gccatcaaac | cacgtcaaat | aatcaattat | gacgcaggta | tcgtattaat | 49140 |
| tgatctgcat | caacttaacg | taaaaacaac | ttcagacaat | acaaatcagc | gacactgaat | 49200 |
| acggggcaac | ctcatgtccc | cccccccccc | cccctgcag | gcatcgtggt | gtcacgctcg | 49260 |
| tcgtttggta | tggcttcatt | cagctccggt | tcccaacgat | caaggcgagt | tacatgatcc | 49320 |
| cccatgttgt | gcaaaaaagc | ggttagctcc | ttcggtcctc | cgatcgttgt | cagaagtaag | 49380 |
| ttggccgcag | tgttatcact | catggttatg | gcagcactgc | ataattctct | tactgtcatg | 49440 |
| ccatccgtaa | gatgcttttc | tgtgactggt | gagtactcaa | ccaagtcatt | ctgagaatag | 49500 |

```
tgtatgcggc gaccgagttg ctcttgcccg gcgtcaacac gggataatac cgcgccacat    49560
agcagaactt taaaagtgct catcattgga aaacgttctt cggggcgaaa actctcaagg    49620
atcttaccgc tgttgagatc cagttcgatg taacccactc gtgcacccaa ctgatcttca    49680 gcatcttta ctttcaccag cgtttctggg tgagcaaaaa caggaaggca aaatgccgca     49740
aaaaagggaa taagggcgac acggaaatgt tgaatactca tactcttcct ttttcaatat    49800
tattgaagca tttatcaggg ttattgtctc atgagcggat acatatttga atgtatttag    49860
aaaaataaac aaatagggt tccgcgcaca tttccccgaa aagtgccacc tgacgtctaa     49920
gaaaccatta ttatcatgac attaacctat aaaaataggc gtatcacgag gccctttcgt    49980
cttcaagaat tggtcgacga tcttgctgcg ttcggatatt ttcgtggagt tcccgccaca    50040
gacccggatt gaaggcgaga tccagcaact cgcgccagat catcctgtga cggaactttg    50100
gcgcgtgatg actggccagg acgtcggccg aaagagcgac aagcagatca cgcttttcga    50160
cagcgtcgga tttgcgatcg aggatttttc ggcgctgcgc tacgtccgcg accgcgttga    50220
gggatcaagc cacagcagcc cactcgacct tctagccgac ccagacgagc caagggatct    50280
ttttggaatg ctgctccgtc gtcaggcttt ccgacgtttg ggtggttgaa cagaagtcat    50340
tatcgtacgg aatgccaagc actcccgagg ggaaccctgt ggttggcatg cacatacaaa    50400
tggacgaacg gataaacctt ttcacgcct tttaaatatc cgttattcta ataaacgctc     50460
ttttctctta ggtttacccg ccaatatatc ctgtcaaaca ctgatagttt aaactgaagg    50520
cgggaaacga caatctgatc atgagcgag aattaaggga gtcacgttat gacccccgcc     50580
gatgacgcgg gacaagccgt tttacgtttg gaactgacag aaccgcaacg ttgaaggagc    50640
cactcagcaa gctggtacga ttgtaatacg actcactata gggcgaattg agcgctgttt    50700
aaacgctctt caactggaag agcggttact accggttaag tgactagggt c            50751
```

<210> SEQ ID NO 7
<211> LENGTH: 20
<212> TYPE: DNA
<213> ORGANISM: Artificial Sequence
<220> FEATURE:
<223> OTHER INFORMATION: Forward primer for GUS expression

<400> SEQUENCE: 7
cggaagcaac gcgtaaactc                                               20

<210> SEQ ID NO 8
<211> LENGTH: 21
<212> TYPE: DNA
<213> ORGANISM: Artificial Sequence
<220> FEATURE:
<223> OTHER INFORMATION: reverse primer for GUS expression

<400> SEQUENCE: 8
tgtgagcgtc gcagaacatt a                                             21

<210> SEQ ID NO 9
<211> LENGTH: 20
<212> TYPE: DNA
<213> ORGANISM: Artificial Sequence
<220> FEATURE:
<223> OTHER INFORMATION: Probe sequence for GUS expression

<400> SEQUENCE: 9
cgcgtccgat cacctgcgtc                                               20

```
<210> SEQ ID NO 10
<211> LENGTH: 23
<212> TYPE: DNA
<213> ORGANISM: Artificial Sequence
<220> FEATURE:
<223> OTHER INFORMATION: TERM F primer

<400> SEQUENCE: 10
ctgtcagttc caaacgtaaa acg                                          23

<210> SEQ ID NO 11
<211> LENGTH: 25
<212> TYPE: DNA
<213> ORGANISM: Artificial Sequence
<220> FEATURE:
<223> OTHER INFORMATION: TERM R primer

<400> SEQUENCE: 11
aatctgatca tgagcggaga attaa                                        25

<210> SEQ ID NO 12
<211> LENGTH: 20
<212> TYPE: DNA
<213> ORGANISM: Artificial Sequence
<220> FEATURE:
<223> OTHER INFORMATION: TERM F primer

<400> SEQUENCE: 12
tcccgggtcc ttaggaagac                                              20

<210> SEQ ID NO 13
<211> LENGTH: 21
<212> TYPE: DNA
<213> ORGANISM: Artificial Sequence
<220> FEATURE:
<223> OTHER INFORMATION: TERM R primer

<400> SEQUENCE: 13
tggattcagc aggcctagaa g                                            21

<210> SEQ ID NO 14
<211> LENGTH: 18
<212> TYPE: DNA
<213> ORGANISM: Artificial Sequence
<220> FEATURE:
<223> OTHER INFORMATION: TERM P-probe

<400> SEQUENCE: 14
tcctcaggat ttaaatgg                                                18

<210> SEQ ID NO 15
<211> LENGTH: 20
<212> TYPE: DNA
<213> ORGANISM: Artificial Sequence
<220> FEATURE:
<223> OTHER INFORMATION: Actin Fwd primer

<400> SEQUENCE: 15
cttcgaatgc ccagcaatgt                                              20

<210> SEQ ID NO 16
<211> LENGTH: 21
<212> TYPE: DNA
<213> ORGANISM: Artificial Sequence
<220> FEATURE:
<223> OTHER INFORMATION: Actin rev primer
```

<400> SEQUENCE: 16
gttcgcccac tagcgtacaa c                                              21

<210> SEQ ID NO 17
<211> LENGTH: 15
<212> TYPE: DNA
<213> ORGANISM: Artificial Sequence
<220> FEATURE:
<223> OTHER INFORMATION: Actin probe

<400> SEQUENCE: 17
tcgaggctgt tcttt                                                     15

<210> SEQ ID NO 18
<211> LENGTH: 584
<212> TYPE: DNA
<213> ORGANISM: Sorghum bicolor

<400> SEQUENCE: 18
gccgtgggtc gtttaagctg ccgctgtacc tgtgtcgtct ggtgccttct ggtgtacctg     60
ggaggttgtc gtctatcaag tatctgtggt tggtgtcatg agtcagtgag tcccaatact    120
gttcgtgtcc tgtgtgcatt atacccaaaa ctgttatggg caaatcatga ataagcttga    180
tgttcgaact taaaagtctc tgctcaatat ggtattatgg ttgttttttgt tcgtctccta    240 atatttgcct gggatcaaat tttattggct ggtgttcatt tgacctccat gttcttgcta    300
ggctccattt tttactctac agccataata tgtttgattg tttggtttgt tctttgttgt    360
acacctggtt ctgtcgagct tagttttcga cactggctta cagcttaaca tgttgctatt    420
ttattgggtt ctgattgcta ttttattggg ttctgattgc tagttttgc tgaatccaaa     480 aaccatgtta tttatttaag cgatccaggt tattattatg atggtggcta agttttttt     540 tttccaaggg taaattttct ggattctcca gtgtttctgt ggcc                     584

<210> SEQ ID NO 19
<211> LENGTH: 3056
<212> TYPE: DNA
<213> ORGANISM: Sorghum bicolor

<400> SEQUENCE: 19
cctgctctgc tcctctccac accacacggc acgaaaccgt tacggcaccg gcagcaccca     60
gcacgggaga ggggattcct ttcccaccgt tccttccctt ccgccccgc cgctataaat     120 agccagcccc atcccagct tttttcccca atctcatctc ctctctcctg ttgttcggag     180
cacacgcaca atccgatcga tccccaaatc cccttcgtct ctcctcgcga gcctcgtgga    240
tcccagcttc aaggtacggc gatcgatcat cccccctcct tctctctacc ttcttttctc    300
tagactacat cggatggcga tccatggtta gggcctgcta gtttcccttc ctgttttgtc    360
gatggctgcg aggcacaata gatctgatgg cgttatgacg gctaacttgt catgttgttg    420
cgatttatag tcccttttagg agatcagttt aatttctcgg atggttcgag atcggtggtc    480
catggttagt accctaagat ccgcgctgtt agggttcgta gatggaggcg acctgttctg    540
attgttaact tgtcagtacc tgggaaatcc tgggatggtt ctagctcgtc cgcagatgag    600
atcgatttca tgatcctctg tatcttgttt cgttgcctag gttccgtcta atctatccgt    660
ggtatgatgt agatgttttg atcgtgctaa ctacgtcttg taaagttaat tgtcaggtca    720 taattttttag catgccttttt tttttgtttg gttttgtcta attgggctgt cgttctagat    780

```
cagagtagaa gactgttcca aactacctgc tggatttatt gaacttggat ctgtatgtgt    840
gtcacatatc ttcataaatt catgattaag atggattgaa atatctttta tcttttggt     900
atggatagtt ctatatgttg gtgtggcttt gttagatgta tacatgctta gatacatgaa    960
gcaacgtgct gctactgttt agtaattgct gttcatttgt ctaataaaca gataaggata   1020
ggtatttatg ttgctgttgg ttttgctggt actttgttgg atacaaatgc ttcaatacag   1080
aaaacagcat gctgctacga tttaccattt atctaatctt atcatatgtc taatctaata   1140
aacaaacatg cttttaaatt atcttcatat gcttggatga tggcatacac agcggctatg   1200
tgtggttttt taaatacccca gcatcatggg catgcatgac actgctttaa tatgcttttt   1260
atttgcttga gactgtttct tttgtttata ctgaccctt agttcggtga ctcttctgca    1320
gatgcagatc tttgtgaaga ccctcactgg caagactatc ccctcgagg tggagtcttc     1380
tgacaccatc gacaacgtca aggccaagat ccaggacaag gaaggcatcc ccccggacca   1440
gcagcggctc atctttgccg gcaagcagct gaggatggg cgcacgcttg ctgactacaa     1500
catccagaag gagagcaccc tccaccttgt gctccgcctc aggggaggca tgcagatctt    1560
cgtgaagacc ctaactggca agacgatcac ccttgaggtg gagtcctcag acaccatcga   1620
caatgtcaag gcaaagatcc aggacaagga gggcatccca ccagaccagc agcgtctgat   1680
cttttgccggc aaacagctgg aggatggccg caccccttgcg gattacaaca tccagaagga  1740
gagcacccctc cacttggtgc tgcgtctcag gggaggcatg caaatcttcg tgaagaccct   1800
tactggcaag acgatcaccc ttgaggtgga gtcctcggac accatcgaca acgtcaaggc   1860
caagatccag gacaaggagg catcccacc ggaccagcag cgtctgatct tgctggcaa      1920
gcagctggag gatggccgca cccttgcgga ttacaacatc cagaaagaga gtaccctcca   1980
cctggtgctc cgcctgaggg gtggcatgca gatctttgtg aagacattga ctggcaagac   2040
catcacgttg gaggttgaga gctctgacac tattgacaat gtgaaggcca agatccagga   2100
caaggagggc attcccccag accagcagcg tctgatcttt gccggcaagc agctggagga   2160
tggccgtacc ctcgctgact acaacatcca gaaggagagc accctccacc tggtgctccg   2220
cctgagggt ggtatgcaga tctttgtgaa gaccttgact ggcaagacca ttaccttgga    2280
ggttgagagc tctgacacca tcgacaatgt gaaagctaag atccaggaca aggagggat    2340
cccccccggac cagcagcgtc tgatcttcgc cggcaagcag ctggaggatg gccgcaccct   2400
tgcagactac aatatccaga aggagagcac cctccatctg gtgctccgtc tccgcggtgg   2460
tcagtaagcc gtgggtcgtt taagctgccg ctgtacctgt gtcgtctggt gccttctggt    2520
gtacctggga ggttgtcgtc tatcaagtat ctgtggttgg tgtcatgagt cagtgagtcc    2580
caatactgtt cgtgtcctgt gtgcattata cccaaaactg ttatgggcaa atcatgaata    2640
agcttgatgt tcgaacttaa aagtctctgc tcaatatggt attatggttg ttttttgttcg    2700
tctcctaata tttgcctggg atcaaatttt attggctggt gttcatttga cctccatgtt   2760
cttgctaggc tccattttt actctacagc cataatatgt ttgattgttt ggtttgttct     2820
ttgttgtaca cctggttctg tcgagcttag ttttcgacac tggcttacag cttaacatgt    2880
tgctatttta ttgggttctg attgctattt tattgggttc tgattgctag ttttttgctga   2940
atccaaaaac catgttattt atttaagcga tccaggttat tattatgatg gtggctaagt    3000
tttttttttt ccaagggtaa attttctgga ttctccagtg tttctgtggc caaaat         3056
```

SB-UBI TERMINATOR SEQUENCE FOR GENE EXPRESSION IN PLANTS

This application claims the benefit of U.S. Provisional Application No. 61/765,900, filed Feb. 18, 2013, the entire content of which is herein incorporated by reference.

FIELD OF INVENTION

The present invention relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have protein coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) EMBO J 18:241-248; Mette et al (2000) EMBO J 19:5194-5201; Mourrain et al (2007) Planta 225:365-379, U.S. Pat. No. 7,632,982, U.S. Pat. No. 7,491,813, U.S. Pat. No. 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

Regulatory sequences located downstream of coding regions contain signals required for transcription termination and 3' mRNA processing, and are called terminator sequences. The terminator sequences play a key role in mRNA processing, localization, stability and translation (Proudfoot, N. (2004) *Curr. Op. Cell Biol* 16:272-278; Gilmartin, 2005). The 3' regulatory sequences contained in terminator sequences can affect the level of expression of a gene. Optimal expression of a chimeric gene in plant cells has been found to be dependent on the presence of appropriate 3' sequences (Ingelbrecht, I. L. W. et al (1989) *Plant Cell* 1:671-680). Read through transcription through leaky terminator of a gene can cause unwanted transcription of one transgene from promoter of another one. Also, bidirectional, convergent transcription of transgenes in transgenic plants can occur due to leaky transcription termination of separate convergent genes or from genomic promoters. Convergent, overlapping transcription can decrease transgene expression, or generate antisense RNA (Bieri, S. et al (2002) *Molecular Breeding* 10:107-117). This underlines the importance of discovering novel and efficient transcriptional terminators.

SUMMARY

The present invention relates to regulatory sequences for modulating gene expression in plants. Specifically, the present invention relates to terminator sequences. Recombinant DNA constructs comprising terminator sequences are provided.

An embodiment of this invention is an isolated polynucleotide sequence comprising: (a) the sequence set forth in SEQ ID NO: 1; (b) a sequence with at least 95% sequence identity SEQ ID NO: 1; or (c) a sequence comprising a functional fragment of (a) or (b), wherein the isolated polynucleotide sequence functions as a terminator in a plant cell. Another embodiment of this invention is a recombinant construct comprising an isolated polynucleotide sequence comprising: (a) the sequence set forth in SEQ ID NO: 1; (b) a sequence with at least 95% sequence identity to SEQ ID NO: 1; or (c) a sequence comprising a functional fragment of (a) or (b), wherein the isolated polynucleotide sequence functions as a terminator in a plant cell. This recombinant construct may further comprise a promoter and a heterologous polynucleotide, wherein the promoter and the heterologous polynucleotide are operably linked to the isolated polynucleotide sequence and are heterologous to the isolated polynucleotide of interest.

Another embodiment of this invention is a method of expressing a heterologous polynucleotide in a plant, comprising the steps of (a) introducing into a regenerable plant cell the recombinant DNA construct described above; (b) regenerating a transgenic plant from the regenerable plant cell of (a); and (c) obtaining a progeny plant from the transgenic plant of step (b), wherein the transgenic plant and the progeny plant comprises the recombinant DNA construct and exhibits expression of the heterologous polynucleotide.

In a fourth embodiment, this invention concerns a vector, cell, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present invention is a monocotyledonous plant. In another embodiment, the plant comprising the terminator sequences described in the present invention is a maize plant.

BRIEF DESCRIPTION OF DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 4A shows GUS reporter gene expression assayed at protein level, and FIG. 4B shows GUS reporter gene expression assayed with qRT-PCR.

Figure 6:
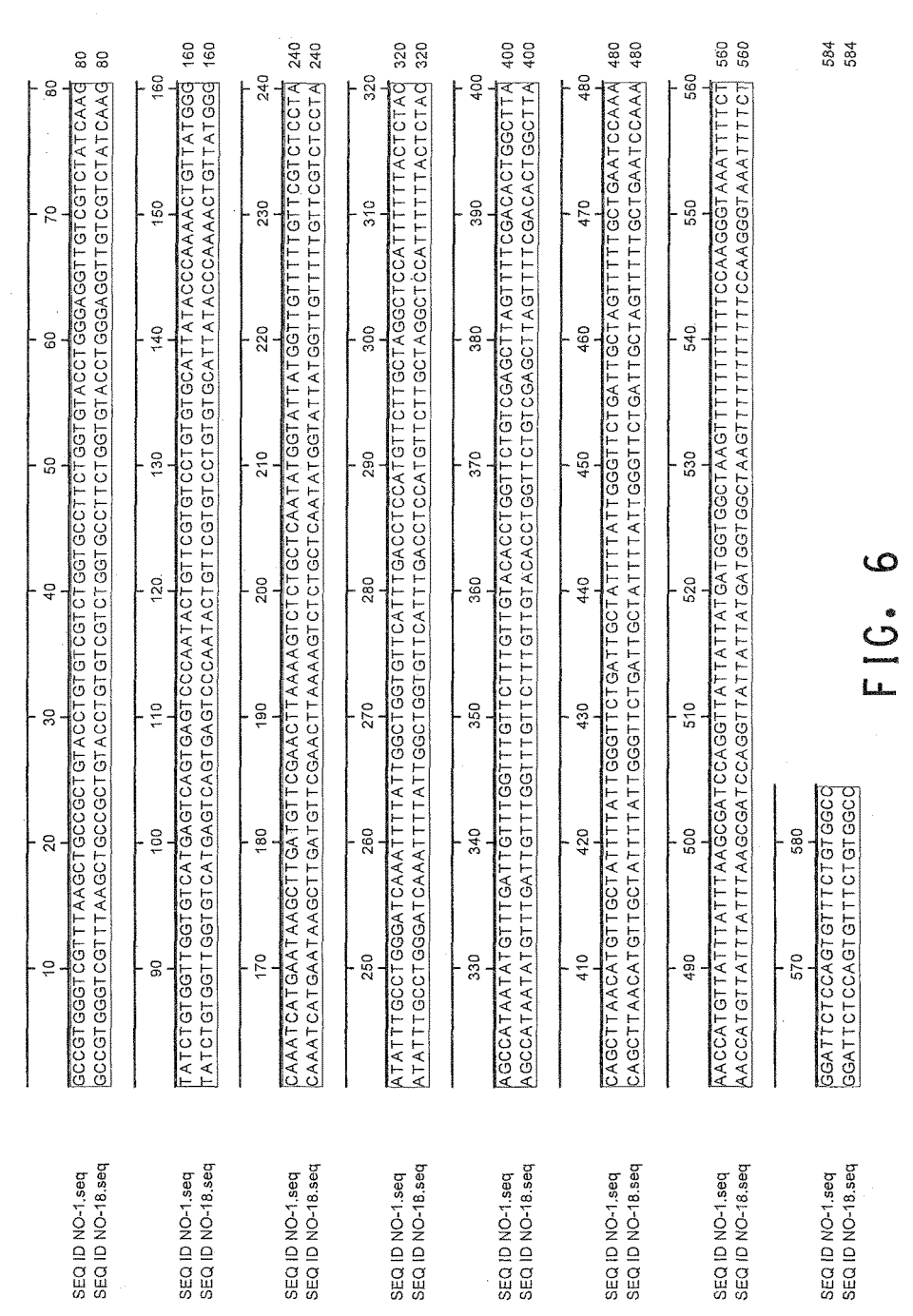

FIG. 6 shows the alignment between the cloned SB-UBI terminator (SEQ ID NO: 1) and the nucleotides 1 to 584 bp 1 of SEQ ID NO: 18 (3'UTR plus downstream genomic sequence).

Figure 1:
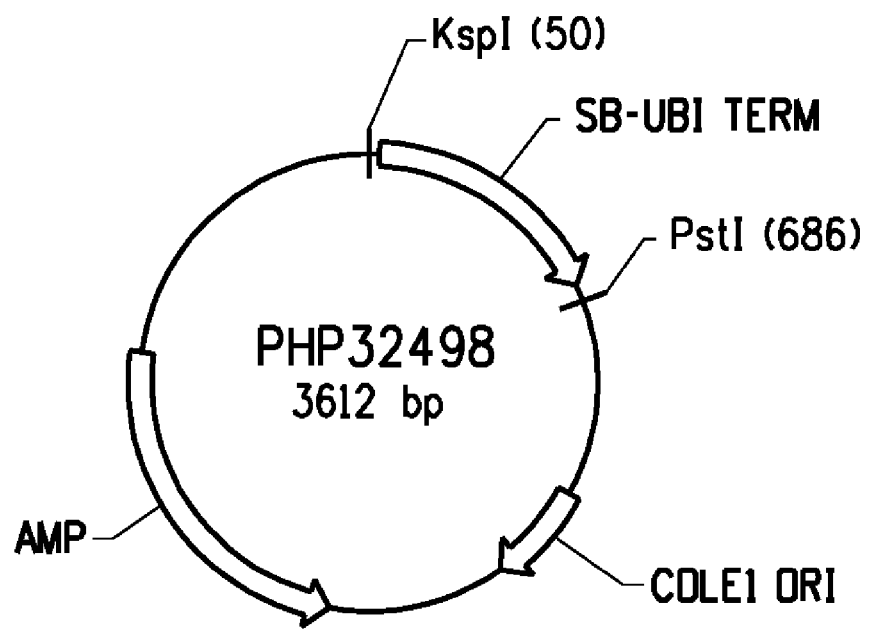
FIG. 1 shows the map of PHP32498, the vector used for cloning the SB-UBI (0.584 kb) terminator after amplification.

SEQ ID NO: 1 is the nucleotide sequence of the 584 bp SB-UBI terminator.

SEQ ID NO: 2 is the nucleotide sequences of the forward primer TMS2118 used to amplify SB-UBI terminator.

SEQ ID NO: 3 is the nucleotide sequences of the reverse primer TMS2119 used to amplify SB-UBI terminator.

SEQ ID NO: 4 is the nucleotide sequence of PHP32498, the vector used for cloning the 1.0 kb SB-UBI terminator after PCR amplification.

SEQ ID NO: 5 is the nucleotide sequence of PHP34006, the vector used for testing the SB-UBI terminator.

SEQ ID NO: 6 is the nucleotide sequence of PHP34005, the test vector used as a control with PINII terminator.

SEQ ID NOS: 7-9 are the sequences of the forward primer, reverse primer and probe used for assessing GUS expression by qRT-PCR in transgenic maize plants, as described in Table 2.

SEQ ID NOS: 10-17 are the sequences of the primers used for quantitating read through transcription through SB-UBI and PINII terminators, by qRT-PCR in transgenic maize plants, as described in Table 3.

SEQ ID NO: 18 corresponds to nucleotides 2468-3051 of Sb04g004260.1 (SEQ ID NO: 19) (3'UTR plus downstream genomic sequence)

SEQ ID NO: 19 is the nucleotide sequence from Phytozome: Sb04g004260.1 genomic sequence (ubiquitin and ubiquitin like proteins) plus 347 bp of downstream genomic sequence of *Sorghum bicolor*.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not found together in nature. Accordingly, a recombinant DNA construct may comprise regulatory sequences and coding sequences that are derived from different sources, or regulatory sequences and coding sequences derived from the same source, but arranged in a manner different than that found in nature. In one embodiment, the recombinant construct comprises an isolated polynucleotide sequence comprising: (a) a nucleotide sequence comprising the sequence set forth in SEQ ID NO:1; (b) a nucleotide sequence comprising a sequence with at least 95% identity to the sequence set forth in SEQ ID NO: 1; or (c) a nucleotide sequence comprising a functional fragment of either (a) or (b); wherein the isolated polynucleotide sequence functions as a transcriptional terminator in a plant cell, wherein said isolated polynucleotide is operably linked to a heterologous sequence that is heterologous to said isolated polynucleotide.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"Transcription terminator", "termination sequences", or "terminator" refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

As used herein, "SB-UBI terminator" or "SB-UBI" or "*Sorghum bicolor*—ubiquitin terminator" refers to the nucleotide sequence from a *Sorghum bicolor* UBI gene that functions as a terminator. The sequence of the SB-UBI terminator is given in SEQ ID NO: 1, which comprises a sequence encoding the 3' untranslated region (239 bp) (3' UTR) of the *Sorghum Bicolor* UBI gene and about 345 bp of sequence downstream from the 3' UTR. The SB-UBI terminator can also be any functional fragment of SEQ ID NO:1, or a derivative of SEQ ID NO:1 obtained by deletion, substitution or addition of one or more nucleotides, wherein the fragment contains terminator activity.

The *Sorghum bicolor* UBI gene encodes a 381 amino acid peptide which is compromised of 5 repeats of a 76 amino acid peptide. This protein is expressed at high levels throughout the plant and involved in many cellular processes.

A "functional fragment" of the terminator is defined as any subset of contiguous nucleotides of the terminator sequence disclosed herein, that can perform the same, or substantially similar function as the full length terminator sequence disclosed herein. A "functional fragment" with substantially similar function to the full length terminator disclosed herein refers to a functional fragment that retains the ability to terminate transcription largely at the same level as the full-length terminator sequence. A recombinant construct comprising a heterologous polynucleotide operably linked to a "functional fragment" of the terminator sequence disclosed herein exhibits levels of heterologous polynucleotide expression substantially similar to a corresponding recombinant construct comprising a heterologous polynucleotide operably linked to the full length terminator sequence.

A "variant", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

As will be evident to one of skill in the art, any heterologous polynucleotide of interest can be operably linked to the terminator sequences described in the current invention. Examples of polynucleotides of interest that can be operably linked to the terminator sequences described in this invention include, but are not limited to, polynucleotides comprising regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the terminator sequences described in the current invention can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

Regulatory Sequences:

A recombinant DNA construct (including a suppression DNA construct) of the present invention may comprise at least one regulatory sequence. In an embodiment of the present invention, the regulatory sequences disclosed herein can be operably linked to any other regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

The terms "real-time PCR", "quantitative PCR", "quantitative real-time PCR" and "QPCR" are used interchangeably herein, and represent a variation of the standard polymerase chain reaction (PCR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the PCR process. Quantification of amplified product is obtained using fluorescent hydrolysis probes that measure increasing fluorescence for each subsequent PCR cycle. The Ct (cycle threshold) is defined as the number of cycles required for the fluorescent signal to cross the threshold (i.e., exceeds background level). DNA/RNA from genes with higher copy numbers will appear after fewer PCR cycles; so the lower a Ct value, the more copies are present in the specific sample. To quantify RNA, QPCR or real-time PCR is preceded by the step of reverse transcribing mRNA into cDNA. This is referred to herein as "real-time RT-PCR" or "quantitative RT-PCR" or "qRT-PCR".

The Taqman method of PCR product quantification uses a fluorescent reporter probe. This is more accurate since the probe is designed to be sequence-specific and will only bind to the specific PCR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a "housekeeping" gene that is relatively abundant in all cell types, is also performed to allow for comparisons between samples. The amount of DNA/RNA is determined by comparing the results to a standard curve produced by serial dilutions of a known concentration of DNA/RNA.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NO:2, SEQ ID NO:1 or SEQ ID NO: 19; or (ii) a nucleic acid sequence of at least 90%, 91%, 92%, 93%, 94%, 95%, 96%, 97%, 98%, 99% or 100% sequence identity, based on the Clustal V method of alignment, when compared to a functional fragment of SEQ ID NO:1; or (iii) a full complement of the nucleic acid sequence of (i) or (ii), wherein the polynucleotide acts as a terminator in a plant cell.

Embodiments of the invention include:

The present invention relates to terminator sequences. Recombinant DNA constructs comprising terminator sequences are provided.

An embodiment of this invention is an isolated polynucleotide sequence comprising (a) the sequence set forth in SEQ ID NO:1; (b) a sequence with at least 95% sequence identity to SEQ ID NO:1; or (c) a sequence comprising a functional fragment of (a) or (b), wherein the isolated polynucleotide sequence functions as a terminator in a plant cell. In another aspect, this invention concerns a recombinant DNA construct comprising a promoter, at least one heterologous nucleic acid fragment, and any terminator, or combination of terminator elements, of the present invention, wherein the promoter, at least one heterologous nucleic acid fragment, and terminator(s) are operably linked.

Recombinant DNA constructs can be constructed by operably linking the nucleic acid fragment of the invention, the terminator sequences set forth SEQ ID NO:1 or a functional fragment of the nucleotide sequence set forth in SEQ ID NO:1 to a heterologous nucleic acid fragment.

Another embodiment of this invention is a method of expressing a heterologous polynucleotide in a plant, comprising the steps of introducing into a regenerable plant cell the recombinant DNA construct described above and regenerating a transgenic plant from the transformed regenerable plant cell, wherein the transgenic plant comprises the recombinant DNA construct and exhibits expression of the heterologous polynucleotide.

Another embodiment of this invention is a method of expressing a heterologous polynucleotide in a plant, comprising the steps of introducing into a regenerable plant cell the recombinant DNA construct described above; regenerating a transgenic plant from the regenerable plant cell described above; and obtaining a progeny plant from the transgenic plant, wherein the transgenic plant and the progeny plant comprises the recombinant DNA construct and exhibits expression of the heterologous polynucleotide.

In another embodiment, this invention concerns a vector, cell, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present invention is a monocotyledenous plant. In another embodiment, the plant comprising the terminator sequences described in the present invention is a maize plant.

Non-limiting examples of compositions and methods disclosed herein are as follows:

1. A recombinant construct comprising an isolated polynucleotide sequence comprising:
   (a) a nucleotide sequence comprising the sequence set forth in SEQ ID NO:1;
   (b) a nucleotide sequence comprising a sequence with at least 95% identity to the sequence set forth in SEQ ID NO: 1; or
   (c) a nucleotide sequence comprising a functional fragment of either (a) or (b);
   wherein the isolated polynucleotide sequence functions as a transcriptional terminator in a plant cell.

2. The recombinant construct of embodiment 1 wherein the isolated polynucleotide is operably linked to a promoter and a heterologous polynucleotide sequence.

3. A plant comprising the recombinant construct of embodiment 1 or 2.

4. The plant of embodiment 3 wherein the plant is a monocot.

5. The plant of embodiment 3 wherein the plant is a maize plant.

6. A seed comprising the recombinant construct of embodiment 1 or 2.

7. The seed of embodiment 3 wherein the seed is from a monocot plant.

8. The seed of embodiment 3 wherein the seed is from a maize plant.

9. A method of expressing a heterologous polynucleotide in a plant, comprising the steps of:
   (a) introducing into a regenerable plant cell the recombinant DNA construct of embodiment 2;
   (b) regenerating a transgenic plant from the regenerable plant cell of step (a), wherein the transgenic plant comprises the recombinant construct of embodiment 2; and
   (c) obtaining a progeny plant from the transgenic plant of step (b), wherein the progeny plant comprises the recombinant DNA construct of embodiment 2 and exhibits expression of the heterologous polynucleotide.

10. The method of embodiment 9, wherein the plant is a monocot plant.

11. The method of embodiment 9, wherein the plant is a maize plant.

12. A transgenic seed produced by the method of embodiment 9.

13. A recombinant construct comprising an isolated polynucleotide sequence comprising:
   (a) a nucleotide sequence comprising the sequence set forth in SEQ ID NO:1;
   (b) a nucleotide sequence comprising a sequence with at least 95% identity to the sequence set forth in SEQ ID NO: 1; or
   (c) a nucleotide sequence comprising a functional fragment of either (a) or (b);

14. A recombinant construct comprising an isolated polynucleotide sequence comprising:
   (a) a nucleotide sequence comprising the sequence set forth in SEQ ID NO:1;
   (b) a nucleotide sequence comprising a sequence with at least 95% identity to the sequence set forth in SEQ ID NO: 1; or (c) a nucleotide sequence comprising a functional fragment of either (a) or (b);
wherein the isolated polynucleotide sequence functions as a transcriptional terminator in a plant cell, wherein said isolated polynucleotide is operably linked to a heterologous sequence that is heterologous to said isolated polynucleotide.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Amplification and Cloning of a *Sorghum bicolor* UBI Terminator Sequence

Primers (SEQ ID NOS: 2 and 3) were designed for amplifying the terminator of UBI gene from *Sorghum bicolor* (SB-UBI) based on the *Sorghum bicolor* genomic sequence database.

The primer sequences are given below, the underlined region is not homologous with genomic template:

```
TMS2118 (forward primer; SEQ ID NO: 2):
ACTAGTGCCGTGGGTCGTTTAAGCTGCC

TMS2119 (reverse primer; SEQ ID NO: 3):
GAATTCGGCCACAGAAACACTGGAGA
```

A 596 bp product comprising the 0.584 kb of SEQ ID NO: 1 was amplified by PCR using these primers. The product was cloned into pGEMTeasy (Promega) (PHP32498; FIG. 1; SEQ ID NO: 4) and the sequence was confirmed. The cloned SB-UBI terminator (SEQ ID NO: 1) included 239 bp of the predicted 3' UTR of the SB-UBI gene along with 345 bp of a downstream sequence corresponding to the nucleotide sequence from Phytozome: Sb04g004260.1 genomic sequence Goodstein et al, Phytozome: a comparative platform for green plant genomics. Nucleic Acids Res., 2012 January; 40(D1): D1178-D1186.) (SEQ ID NO: 19).

Figure 2:
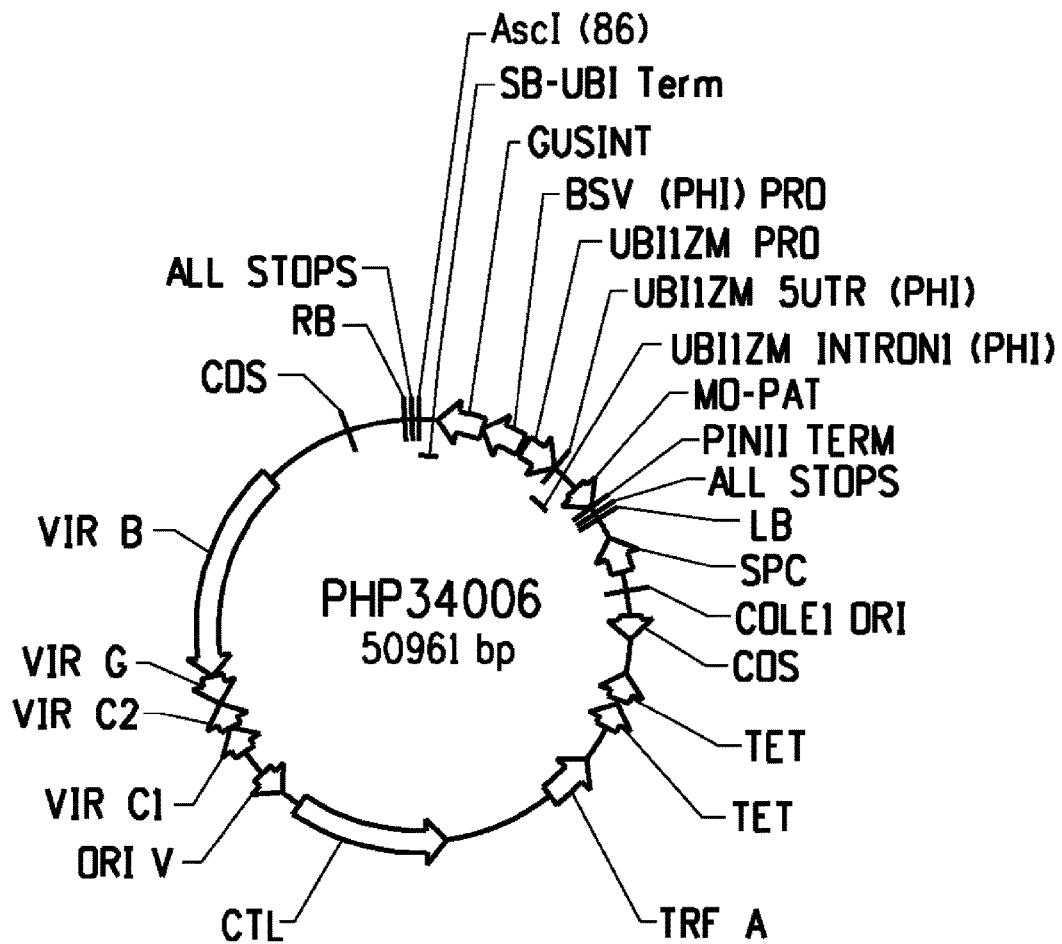
FIG. 2 shows the map of PHP34006 the vector used for testing the 0.584 kb SB-UBI terminator (SB-UBI TERM).

The amplified sequence of the SB-UBI terminator (SEQ ID NO: 1) was then cloned into an *Agrobacterium* transformation vector (PHP34006; FIG. 2; SEQ ID NO: 5), which had the following expression cassettes in divergent orientation: SB-UBI TERMINATOR: GUSINT: BSV PRO and UBI-PRO:UBI INTRON:MOPAT:PINII TERM. BSV PRO is Banana Streak Virus promoter, which is a strong constitutive promoter. A construct with a potato PINII terminator (Keil et al. 1986 Nucleic Acids Res. 14:5641-5650) in place of the SB-UBI terminator was used as a control (PHP34005; SEQ ID NO: 6).

Example 2

Transient Transformation to Test Efficacy of a SB-UBI Terminator

Figure 3:
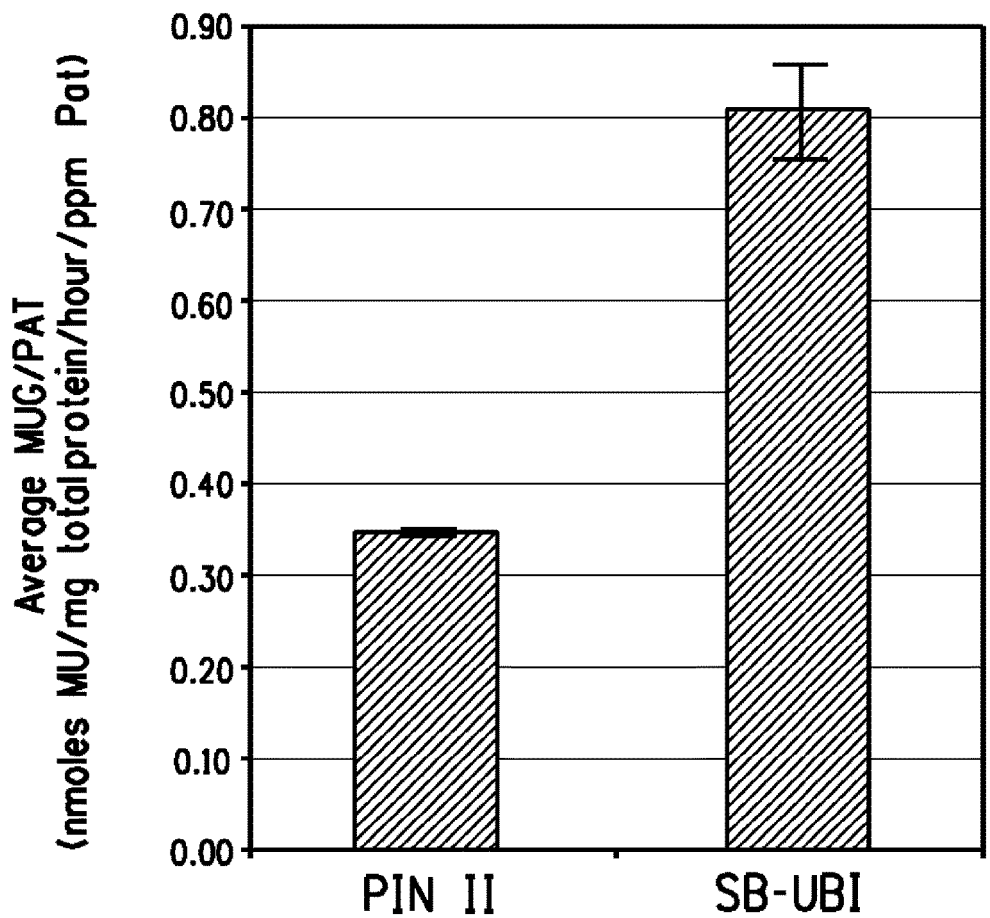
FIG. 3 shows the results of testing the 0.584 kb SB-UBI terminator compared to PINII terminator in transient assays. It shows quantitative analysis of GUS reporter gene expression in BMS cells transformed with PHP34006 (0.584 kb SB-UBI terminator) and PHP34005 (PINII terminator).

The isolated SB-UBI terminator sequences (SEQ ID NO: 1) was tested for its ability to act efficiently as a terminator in a recombinant construct. Its efficacy as a terminator was tested by its ability to stop transcription and by its ability to increase expression of a protein. Since improper termination can lead to improper processing of the 3' end of mRNA, and hence affect RNA stability, terminators have been found to affect protein expression levels. It has been shown that different terminators can cause up to 100 fold variation in the efficiency of transgene expression (Bieri et al, (2002) *Molecular Breeding* 10: 107-117; An et al (1989) *Plant Cell* 1: 115-122; Ingelbrecht et al (1989), *Plant Cell,* 1:671-680; Ali and Taylor (2001) *Plant Mol. Bio.,* 46:251-261). The SB-UBI sequence (SEQ ID NO: 1) was tested for its ability to increase expression of a protein compared to the well-known PINII terminator. The *Agrobacterium* transformation vectors PHP34006 (SEQ ID NO: 5) and PHP34005 (SEQ ID NO: 6) described in example 1 were used for transient transformation of BMS (Black Mexican Sweet) cells. The cells were harvested 5 days after transformation and sent for a quantification of the GUS activity (MUG assay). The SB-UBI terminator (PHP34006; SEQ ID NO: 5) had ~138% more expression than that of the PINII construct (PHP34005, SEQ ID NO: 6) when the GUS expression was normalized to the MOPAT expression (FIG. 3; Table 1). This information was indicative of the ability of the isolated SB-UBI sequence (SEQ ID NO: 1) to act efficiently as a terminator, by allowing protein expression equal to or above that of the PINII terminator.

TABLE 1

| Construct | Sequence Tested | Average MUG/PAT* | Standard Deviation |
|---|---|---|---|
| BSV PRO:GUSINT:PINII TERM | PIN II TERM | 0.34 | 0.00 |
| BSV PRO:GUSINT:SB-UBI TERM | SB-UBI TERM | 0.81 | 0.04 |

*Measured as: nmoles MU/mg total protein/hour/ppm PAT

Example 3

Stable Transformation Assays to Test SB-UBI Terminator Activity

The *Agrobacterium* transformation vectors PHP34006 (SEQ ID NO: 5) and PHP 34005 (SEQ ID NO: 6) described in Example 1, that were used for transient transformation assays as described in Example 2, were also used in Gaspe-Flint derived maize lines for stable transformation to generate transgenic maize plants.

Quantitative Reverse Transcriptase-PCR (qRT-PCR) and GUS assays were done from stably transformed plant tissues to test the ability of isolated SB-UBI terminator sequence (SEQ ID NO:1) to stop transcription (that is prevent transcription read-through transcription) and to compare GUS expression as compared to that with PINII terminator.

GUS Expression Analysis:

The expression of the GUS gene in the transgenic plants was assessed at the protein as well as transcript levels. To assess the expression at the protein level, MUG assay was performed on seedling leaf material. To assess the expression at the transcript level, qRT-PCR was done using primers shown in Table 2.

TABLE 2

| Primer/<br>Probe | Type | Sequence | Fluor | qPCR<br>Assay |
|---|---|---|---|---|
| GUS-<br>1482F | Forward | CGGAAGCAACGCGTAAACTC<br>(SEQ ID NO: 7) | - | Taqman |

TABLE 2-continued

| Primer/<br>Probe | Type | Sequence | Fluor | qPCR<br>Assay |
|---|---|---|---|---|
| GUS-<br>1553R | Reverse | TGTGAGCGTCGCAGAACATTA<br>(SEQ ID NO: 8) | - | Taqman |
| GUS-<br>1509P | Probe | CGCGTCCGATCACCTGCGTC<br>(SEQ ID NO: 9) | FAM | Taqman |

Figure 4A:
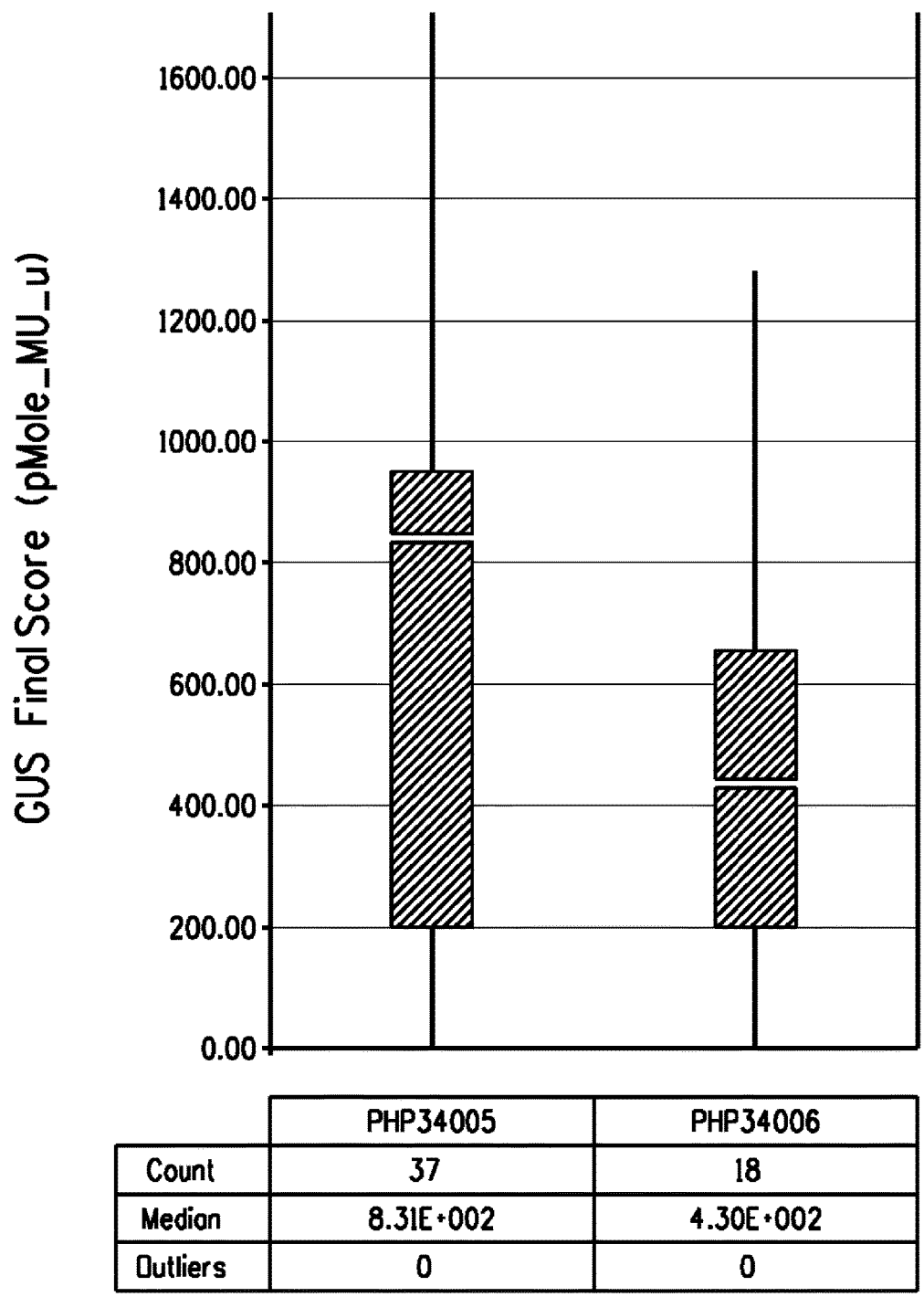
FIG. 4A and FIG. 4B show quantitative analysis of GUS reporter gene expression in Gaspe Flint derived maize lines stably transformed with SB-UBI (PHP34006) and PINII (PHP34005) terminator constructs.
Figure 4B:
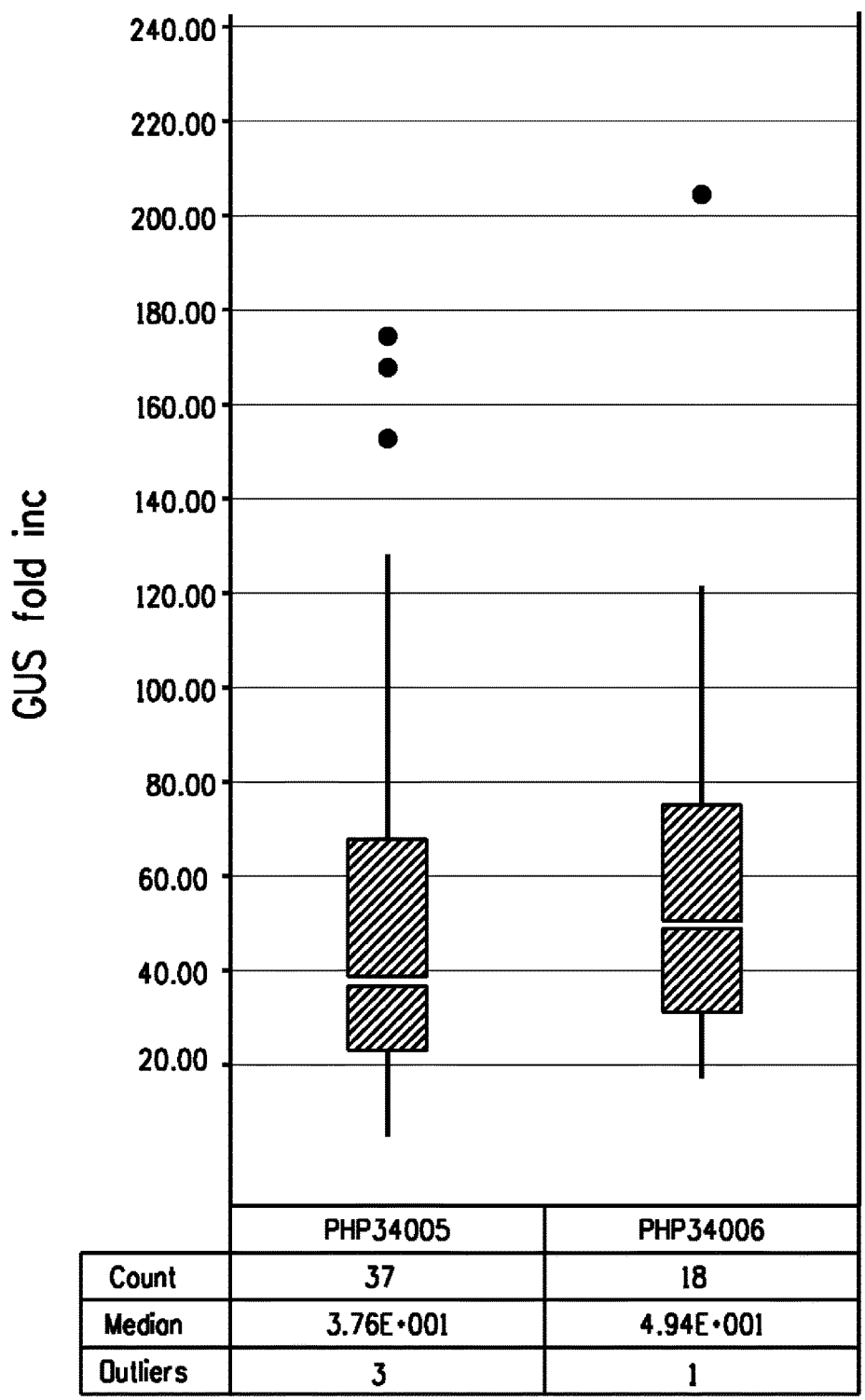

Plants were grown in the greenhouse and leaves were sampled at the R1 stage of development for expression analysis. Multiple plants were tested for each construct. Each plant was analyzed for expression of the GUS gene. GUS gene with the SB-UBI terminator had GUS expression in the same range as that of PINII terminator at both the protein (FIG. 4A) and transcript (FIG. 4B) level.

Quantitative Reverse Transcriptase PCR (qRT-PCR) to Determine Read-Throuqh Transcription Through the SB-UBI Terminator:

qRT-PCR assays were performed with leaf tissue from the stable transformants generated using PHP34006 and PHP34005. Each plant was tested for the presence of read-through transcript that had passed through the PINII terminator and the SB-UBI terminator (SEQ ID NO: 1). To assess presence of products that would indicate that transcription was continuing past the terminator, amplification was targeted downstream of the terminator being tested. Two primer sets were designed downstream of the tested terminator.

Primer set Term1 ~100 nt from the terminator

Primer set Term2.1 ~500 nt from the terminator

Multiple plants were tested for each construct. The primers are shown in Table 3.

TABLE 3

| Primer/<br>Probe | Name | Type | Sequence | Fluor | qPCR<br>Assay |
|---|---|---|---|---|---|
| Term2.1[1] | Term2.1F | fwd | CTGTCAGTTCCAAACGTAAAACG<br>(SEQ ID NO: 10) | - | SYBR |
| Term2.1[1] | Term2.1R | rev | AATCTGATCATGAGCGGAGAATTAA<br>(SEQ ID NO: 11) | - | SYBR |
| Term1[1] | Term 1F | fwd | TCCCGGGTCCTTAGGAAGAC<br>(SEQ ID NO: 12) | - | Taqman |
| Term1[1] | Term 1R | rev | TGGATTCAGCAGGCCTAGAAG<br>(SEQ ID NO: 13) | - | Taqman |
| Term1[1] | Term_1P | probe | TCCTCAGGATTTAAATGG<br>(SEQ ID NO: 14) | FAM | Taqman |
| Actin[2] | Actin_MGB_F | fwd | CTTCGAATGCCCAGCAATGT<br>(SEQ ID NO: 15) | - | Taqman |
| Actin[2] | Actin_MGB_R | rev | GTTCGCCCACTAGCGTACAAC<br>(SEQ ID NO: 16) | - | Taqman |
| Actin[2] | Actin_VIC_P | probe | TCGAGGCTGTTCTTT<br>(SEQ ID NO: 17) | VIC | Taqman |

[1]Post-Terminator Primer Set
[2]Reference Gene

The test plants were classified into 3 categories depending on the qRT-PCR results:

1. Plants showing complete termination: where all GUS transcripts are completely terminated before they reached the specific primer set location;
2. Plants showing a high degree of termination: where a large portion of the GUS transcripts are terminated before they reached the specific primer set location, also defined as:
   Primer set Term1-ΔCT>13
   Primer set Term2.1-ΔCT>9; and
3. Plants showing poor termination.

Figure 5A:
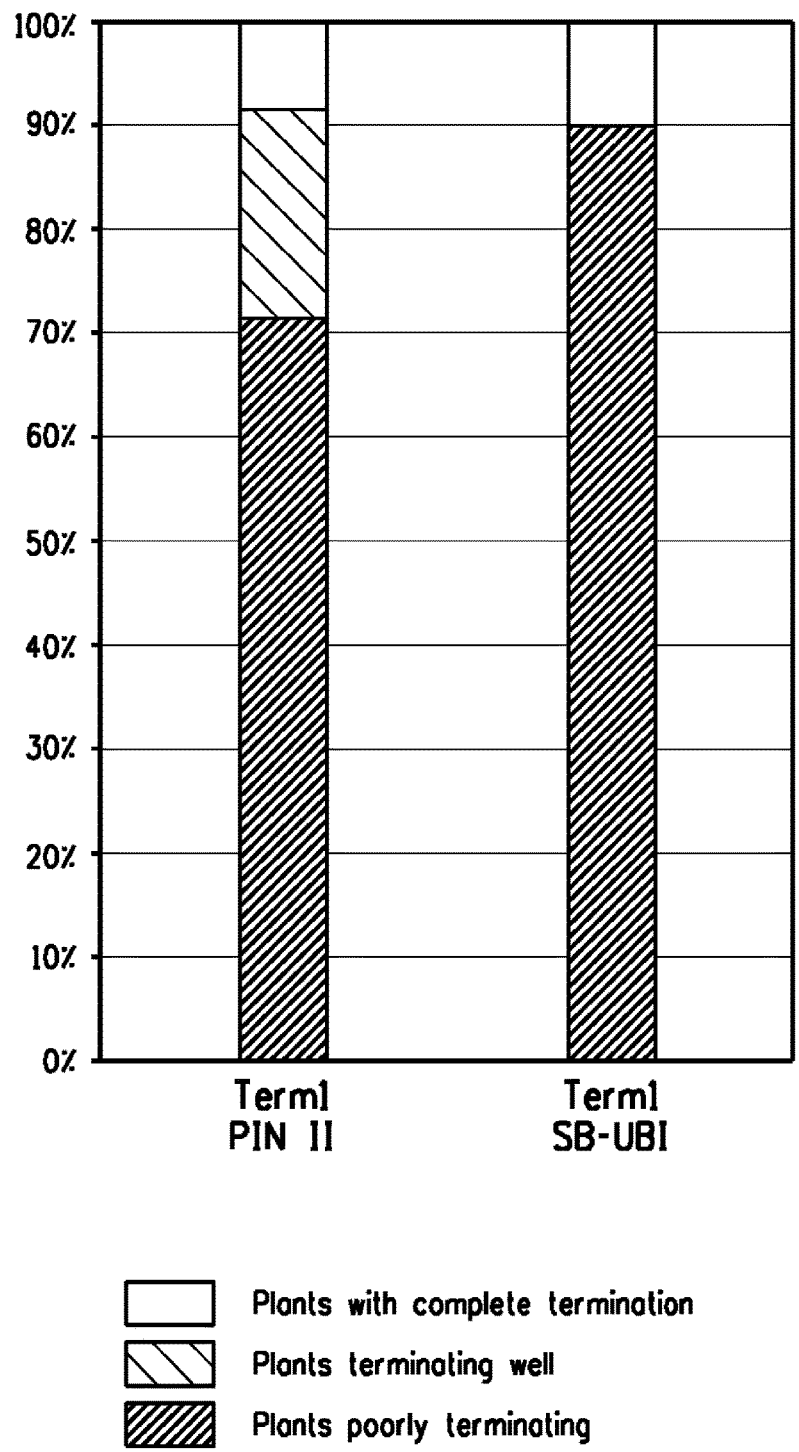
FIGS. 5A and 5B show the results of qRT-PCR assays with stably transformed Gaspe Flint derived maize lines, using two sets of primers (set 1 in 5A and set 2 in 5B) downstream of the SB-UBI terminator and the PINII terminator.
Figure 5B:
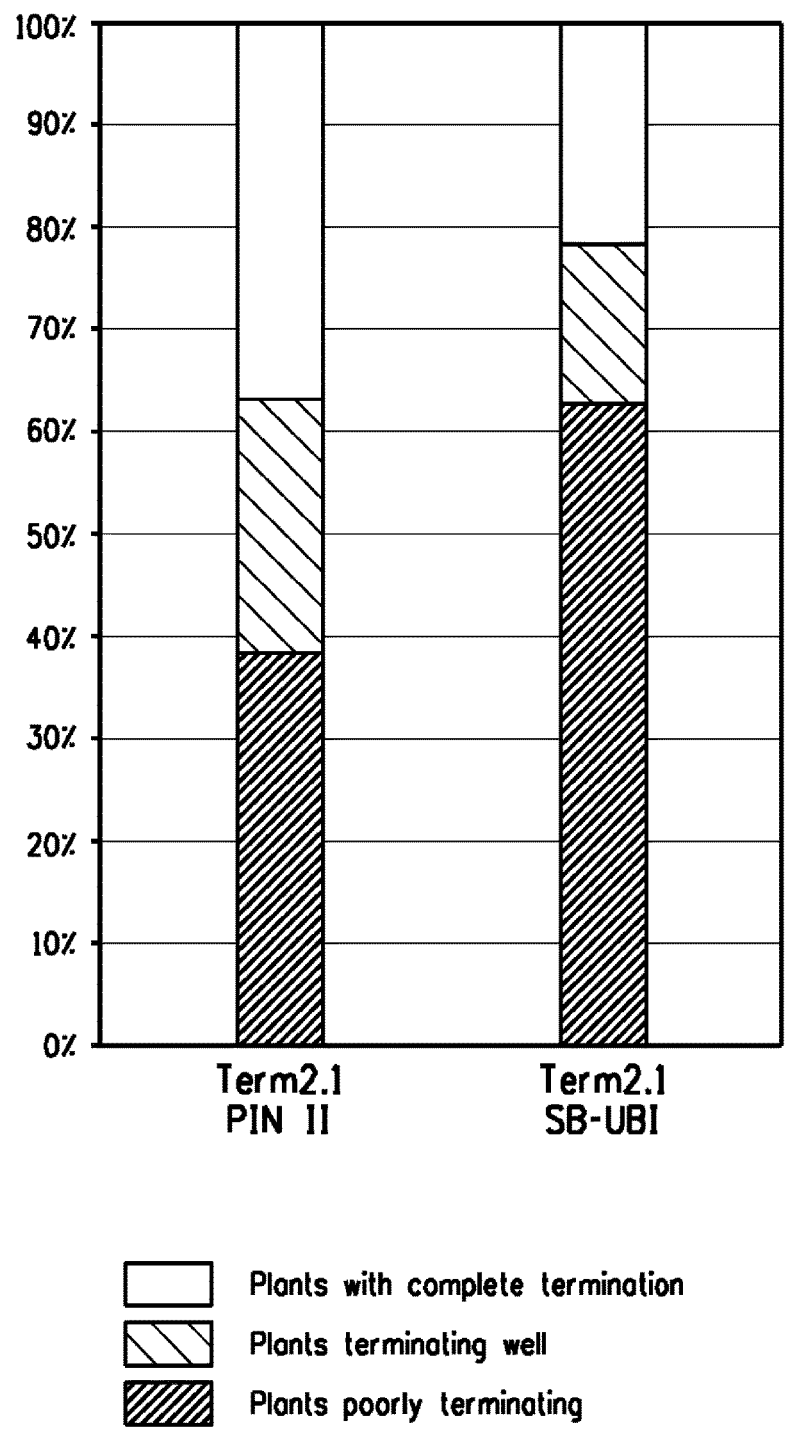

As can be seen from FIG. 5, the 0.5 kb SB-UBI terminator proved to have similar "poorly terminating" plants than the PINII terminator (FIG. 5). Thus the qRT-PCR score for presence of transcripts that had proceeded through the terminator was similar than the SB-UBI terminator than that for the PINII terminator.

What is claimed is:

1. A recombinant DNA construct comprising an isolated polynucleotide sequence and a terminator sequence set forth in SEQ ID NO:1, wherein said terminator sequence functions as a transcriptional terminator in a plant cell, and wherein said polynucleotide sequence is heterologous to said terminator sequence.

2. A plant comprising the recombinant DNA construct of claim 1.

3. The plant of claim 2 wherein the plant is a monocot.

4. The plant of claim 2 wherein the plant is a maize plant.

5. A seed comprising the recombinant DNA construct of claim 1.

6. The seed of claim 5 wherein the seed is from a monocot plant.

7. The seed of claim 5 wherein the seed is from a maize plant.

8. A method of expressing a polynucleotide sequence in a plant, comprising the steps of:

(a) introducing into a regenerable plant cell the recombinant DNA construct of claim 1, wherein said polynucleotide sequence is heterologous to said terminator sequence;

(b) regenerating a transgenic plant from the regenerable plant cell of step (a), wherein the transgenic plant comprises the recombinant DNA construct of claim 1; and (c) obtaining a progeny plant or seed from the transgenic plant of step (b), wherein the progeny plant or seed comprises the recombinant DNA construct of claim 1 and exhibits expression of the heterologous polynucleotide.

9. The method of claim 8, wherein the plant is a monocot plant.

10. The method of claim 8, wherein the plant is a maize plant.

11. A transgenic seed produced by the method of claim 8, wherein said seed comprises the recombinant DNA construct.

* * * * *